(12) United States Patent
Plaetinck et al.

(10) Patent No.: US 7,005,423 B1
(45) Date of Patent: Feb. 28, 2006

(54) CHARACTERIZATION OF GENE FUNCTION USING DOUBLE STRANDED RNA INHIBITION

(75) Inventors: Geert Plaetinck, Zwynaarde (BE); Christ Platteeuw, Zwynaarde (BE); Katherine Mortier, Zwynaarde (BE); Thierry Bogart, Zwynaarde (BE)

(73) Assignee: Devgen NV, Ghent-Zwijnaarde (BE)

( * ) Notice: Subject to any disclaimer, the term of this patent is extended or adjusted under 35 U.S.C. 154(b) by 0 days.

(21) Appl. No.: 09/347,311

(22) Filed: Jul. 2, 1999

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl. ............... 514/44; 536/23.1; 536/24.5; 435/6; 435/325

(58) Field of Classification Search ............... 536/23.1, 536/24.5; 514/44; 435/6, 325, 455; 800/84
See application file for complete search history.

(56) References Cited

U.S. PATENT DOCUMENTS 6,506,559 B1 * 1/2003 Fire et al. ............... 435/6

FOREIGN PATENT DOCUMENTS

| CA | 2 088 379 A1 | 7/1994 |
|---|---|---|
| WO | WO 90/14090 | 11/1990 |
| WO | WO 91/15111 | 10/1991 |
| WO | WO 95/34680 | 12/1995 |
| WO | WO 96/38553 | 12/1996 |
| WO | WO 96/38555 | 12/1996 |
| WO | WO 99/32619 | 7/1999 |
| WO | WO 99/53050 | 10/1999 |
| WO | WO 99/61631 | 12/1999 |

OTHER PUBLICATIONS

Fire et al., Potent and specific genetic interference by double-starded RNA in *Caenorhabditis elegans,* Feb. 19, 1998, Nature, vol. 391, pp. 806-811.*
Deonarain et al., Ligand-targeted receptor-mediated vectors for gene delivery, 1998, Exp. Opin., Ther. Patents, vol. 8, No. 1 pp. 53-69.*
Verma et al., Gene therapy-promises,problems and prospects, Sep. 18, 1997, Nature, vol. 389, pp. 239-242.*
Crystal, Transfer of Genes to Humans: Early Lessons and Obstacles to Success, 1995, Science, pp. 404-410.*
http://genomics.phrma.org/lexicon/p.html#phenotype.*
Vennema et al., *Gene* 108(2):201-209 (1991).
Gast, F., *Nucleic Acids Res.* 17(23):10109 (1989).
Fire et al., *Nature* 391:806-811 (1998).
Bogeart et al., Database Geneseq Acc. No. T71322 (1997) & abstract WO96 38555 (1996).
Chien et al., *Proc Natl Acad Sci USA* 88:9578-9582 (1991).
James et al., Database Medline Acc. No. 97132579.
James et al., Database EMBL Acc. No. U70025 (1996).
Timmons and Fire, *Nature* 395:854 (1998).
Timmons and Fire, *East Coast Worm Meeting Abstract 180* (Jun. 27, 2002).

* cited by examiner

*Primary Examiner*—Joseph Woitach
(74) *Attorney, Agent, or Firm*—Wolf, Greenfield & Sacks, P.C.

(57) ABSTRACT

There is provided a method of identifying DNA responsible for conferring a particular phenotype in a cell which method comprises a) constructing a cDNA or genomic library of the DNA of the cell in a suitable vector in an orientation relative to a promoter(s) capable of initiating transcription of the cDNA or DNA to double stranded (ds) RNA upon binding of an appropriate transcription factor to the promoter(s), b) introducing said library into one or more of the cells comprising the transcription factor, and c) identifying and isolating a particular phenotype of the cell comprising the library and identifying the DNA or cDNA fragment from the library responsible for conferring the phenotype. Using this technique it is also possible to assign a function to a known DNA sequence by a) identifying a homologue(s) of the DNA sequence in a cell, b) isolating the relevant DNA homologues(s) or a fragment thereof from the cell, c) cloning the homologue or fragment thereof into an appropriate vector in an orientation relative to a suitable promoter(s) capable of initiating transcription of dsRNA from the DNA homologue or fragment upon binding of an appropriate transcription factor to the promoter(s), and d) introducing the vector into the cell from step a) comprising the transcription factor.

37 Claims, 19 Drawing Sheets pGN1
gagtgcaccatatgcggtgtgaaataccgcacagatgcgtaaggagaaaataccgcatcaggcgaaattgtaaacgtta
atattttgttaaaattcgcgttaaatatttgttaaatcagctcatttttaaccaataggccgaaatcggcaaaatcccttataaat
caaaagaatagaccgagatagggttgagtgttgttccagtttggaacaagagtccactattaaagaacgtggactccaac
gtcaaagggcgaaaaaccgtctatcagggcgatggcccactacgtgaaccatcacccaaatcaagtttttgcggtcgag
gtgccgtaaagctctaaatcggaacccaaagggagccccgatttagagcttgacggggaaagccggcgaacgtggc
gagaaaggaagggaagaaagcgaaaggagcgggcgctagggcgctggcaagtgtagcggtcacgctgcgcgtaac
caccacacccgccgcgcttaatgcgccgctacagggcgcgtccattcgccattcaggctgcgcaactgttgggaagggc
gatcggtgcgggcctcttcgctattacgccagctggcgaaaggggggatgtgctgcaaggcgattaagttgggtaacgcca
gggttttcccagtcacgacgttgtaaaacgacggccagtgaattgtaatacgactcactatagggcgaattcgagctcggta
cccggggatcctctagagtcgaaagcttctcgccctatagtgagtcgtattacagcttgagtattctatagtgtcacctaaata
gcttggcgtaatcatggtcatagctgtttcctgtgtgaaattgttatccgctcacaattccacacaacatacgagccggaagc
ataaagtgtaaagcctggggtgcctaatgagtgagctaactcacattaattgcgttgcgctcactgcccgctttccagtcggg
aaacctgtcgtgccagctgcattaatgaatcggccaacgcgcggggagaggcggtttgcgtattgggcgctcttccgcttcc
tcgctcactgactcgctgcgctcggtcgttcggctgcggcgagcggtatcagctcactcaaaggcggtaatacggttatcca
cagaatcaggggataacgcaggaaagaacatgtgagcaaaaggccagcaaaaggccaggaaccgtaaaaaggcc
gcgttgctggcgtttttcgataggctccgcccccctgacgagcatcacaaaaatcgacgctcaagtcagaggtggcgaaa
cccgacaggactataaagataccaggcgtttccccctggaagctccctcgtgcgctctcctgttccgaccctgccgcttacc
ggatacctgtccgcctttctcccttcgggaagcgtggcgctttctcatagctcacgctgtaggtatctcagttcggtgtaggtcgt
tcgctccaagctgggctgtgtgcacgaaccccccgttcagcccgaccgctgcgccttatccggtaactatcgtcttgagtcc
aacccggtaagacacgacttatcgccactggcagcagccactggtaacaggattagcagagcgaggtatgtaggcggt
gctacagagttcttgaagtggtggcctaactacggctacactagaaggacagtatttggtatctgcgctctgctgaagccagt
taccttcggaaaaagagttggtagctcttgatccggcaaacaaaccaccgctggtagcggtggtttttttgtttgcaagcagc
agattacgcgcagaaaaaaaggatctcaagaagatcctttgatcttttctacggggtctgacgctcagtggaacgaaaact
cacgttaagggattttggtcatgagattatcaaaaaggatcttcacctagatcctttaaattaaaaatgaagttttaaatcaatc
taaagtatatatgagtaaacttggtctgacagttaccaatgcttaatcagtgaggcacctatctcagcgatctgtctatttcgttc
atccatagttgcctgactccccgtcgtgtagataactacgatacgggagggcttaccatctggccccagtgctgcaatgata
ccgcgagacccacgctcaccggctccagatttatcagcaataaaccagccagccggaagggccgagcgcagaagtg
gtcctgcaactttatccgcctccatccagtctattaattgttgccgggaagctagagtaagtagttcgccagttaatagtttgcg
caacgttgttggcattgctacaggcatcgtggtgtcacgctcgtcgtttggtatggcttcattcagctccggttcccaacgatca
aggcgagttacatgatccccatgttgtgcaaaaaagcggttagctccttcggtcctccgatcgttgtcagaagtaagttggc
cgcagtgttatcactcatggttatggcagcactgcataattctcttactgtcatgccatccgtaagatgcttttctgtgactggtga
gtactcaaccaagtcattctgagaataccgcgcccggcgaccgagttgctcttgcccggcgtcaatacgggataatagtgt
atgacatagcagaactttaaaagtgctcatcattggaaaacgttcttcggggcgaaaactctcaaggatcttaccgctgttga
gatccagttcgatgtaacccactcgtgcacccaactgatcttcagcatcttttactttcaccagcgtttctgggtgagcaaaaa
caggaaggcaaaatgccgcaaaaaagggaataagggcgacacgaaatgttgaatactcatactcttccttttcaatatt
attgaagcatttatcaggggttattgtctcatgagcggatacatatttgaatgtatttagaaaaataaacaaataggggttccgc
gcacatttccccgaaaagtgccacctgacgtctaagaaaccattattatcatgacattaacctataaaaataggcgtatcac
gaggccctttcgtctcgcgcgtttcggtgatgacggtgaaaacctctgacacatgcagctcccggagacggtcacagcttgt
ctgtaagcggatgccgggagcagacaagcccgtcagggcgcgtcagcgggtgttggcgggtgtcggggctggcttaact
atgcggcatcagagcagattgtactga

FIG. 1 pGN100
ctagcatgaacacgattaacatcgctaagaacgacttctctgacatcgaactggctgctatcccgttcaacactctggctga
ccattacggtgagcgtttagctcgcgaacagttggcccttgagcatgagtcttacgagatgggtgaagcacgcttccgcaa
gatgtttgagcgtcaacttaaagctggtgaggttgcggataacgctgccgccaagcctctcatcactaccctactccctaag
atgattgcacgcatcaacgactggtttgaggaagtgaaagctaagcgcggcaagcgcccgacagccttccagttcctgca
agaaatcaagccggaagccgtagcgtacatcaccattaagaccactctggcttgcctaaccagtgctgacaatacaacc
gttcaggctgtagcaagcgcaatcggtcgggccattgaggacgaggctcgcttcggtcgtatccgtgaccttgaagctaag
cacttcaagaaaaacgttgaggaacaactcaacaagcgcgtagggcacgtctacaagaaagcatttatgcaagttgtcg
aggctgacatgctctctaagggtctactcggtggcgaggcgtggtcttcgtggcataaggaagactctattcatgtaggagt
acgctgcatcgagatgctcattgagtcaaccggaatggttagcttacaccgccaaaatgctggcgtagtaggtcaagactc
tgagactatcgaactcgcacctgaatacgctgaggctatcgcaacccgtgcaggtgcgctggctggcatctctccgatgttc
caaccttgcgtagttcctcctaagccgtggactggcattactggtggtggctattgggctaacggtcgtcgtcctctggcgctg
gtgcgtactcacagtaagaaagcactgatgcgctacgaagacgtttacatgcctgaggtgtacaaagcgattaacattgcg
caaaacaccgcatggaaaatcaacaagaaagtcctagcggtcgccaacgtaatcaccaagtggaagcattgtccggtc
gaggacatccctgcgattgagcgtgaagaactcccgatgaaaccggaagacatcgacatgaatcctgaggctctcaccg
cgtggaaacgtgctgccgctgctgtgtaccgcaaggacagggctcgcaagtctcgccgtatcagccttgagttcatgcttga
gcaagccaataagtttgctaaccataaggccatctggttcccttacaacatggactggcgcggtcgtgtttacgccgtgtcaa
tgttcaacccgcaaggtaacgatatgaccaaaggactgcttacgctggcgaaaggtaaaccaatcggtaaggaaggtta
ctactggctgaaaatccacggtgcaaactgtgcgggtgtcgataaggttccgttccctgagcgcatcaagttcattgaggaa
aaccacgagaacatcatggcttgcgctaagtctccactggagaacacttggtgggctgagcaagattctccgttctgcttcct
tgcgttctgctttgagtacgctggggtacagcaccacggcctgagctataactgctccttccgctggcgtttgacgggtcttg
ctctggcatccagcacttctccgcgatgctccgagatgaggtaggtggtcgcgcggttaacttcttcctagtgagaccgttc
aggacatctacgggattgttgctaagaaagtcaacgagattctacaagcagacgcaatcaatgggaccgataacgaagt
agttaccgtgaccgatgagaacactggtgaaatctctgagaaagtcaagctgggcactaaggcactggctggtcaatggc
tggctcacggtgttactcgcagtgtgactaagcgttcagtcatgacgctggcttacgggtccaaagagttcggcttccgtcaa
caagtgctggaagataccattcagccagctattgattccggcaagggtccgatgttcactcagccgaatcaggctgctgga
tacatggctaagctgatttgggaatctgtgagcgtgacggtggtagctgcggttgaagcaatgaactggcttaagtctgctgc
taagctgctggctgctgaggtcaaagataagaagactggagagattcttcgcaagcgttgcgctgtgcattgggtaactcct
gatggtttccctgtgtggcaggaatacaagaagcctattcagacgcgcttgaacctgatgttcctcggtcagttccgcttaca
gcctaccattaacaccaacaaagatagcgagattgatgcacacaaacaggagtctggtatcgctcctaactttgtacaca
gccaagacggtagccaccttcgtaagactgtagtgtgggcacacgagaagtacggaatcgaatcttttgcactgattcacg
actccttcggtaccattccggctgacgctgcgaacctgttcaaagcagtgcgcgaaactatggttgacacatatgagtcttgt
gatgtactggctgatttctacgaccagttcgctgaccagttgcacgagtctcaattggacaaaatgccagcacttccggctaa
aggtaacttgaacctccgtgacatcttagagtcggacttcgcgttcgcgtaaccatggtattgatatctgagctccgcatcggc
cgctgtcatcagatcgccatctcgcgcccgtgcctctgacttctaagtccaattactcttcaacatccctacatgctctttctccct
gtgctccaccccctattttgttattatcaaaaaaacttcttcttaatttctttgttttttagcttcttttaagtcacctctaacaatgaa
attgtgtagattcaaaaatagaattaattcgtaataaaaagtcgaaaaaaattgtgctccctcccccattaataataattctat
cccaaaatctacacaatgttctgtgtacacttcttatgtttttttttacttctgataaatttttttgaaacatcatagaaaaaaccgca
cacaaaatccttatcatatgttacgtttcagtttatgaccgcaattttatttcttcgcacgtctgggcctctcatgacgtcaaatc
atgctcatcgtgaaaaagttttggagtattttggaattttcaatcaagtgaaagtttatgaaattaattttcctgcttttgcttttgg
gggtttcccctattgtttgtcaagagtttcgaggacggcgttttcttgctaaaatcacaagtattgatgagcacgatgc
```

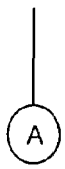

*FIG. 2A*

| Fig. 2A |
| Fig. 2B |

(A)

(B)

aagaaagatcggaagaaggtttgggtttgaggctcagtggaaggtgagtagaagttgataatttgaaagtggagtagtgtc
tatggggttttgccttaaatgacagaatacattcccaatataccaaacataactgtttcctactagtcggccgtacgggcccttt
tcgtctcgcgcgtttcggtgatgacggtgaaaacctctgacacatgcagctcccggagacggtcacagcttgtctgtaagcg
gatgccgggagcagacaagcccgtcagggcgcgtcagcggtgttggcgggtgtcggggctggcttaactatgcggcat
cagagcagattgtactgagagtgcaccatatgcggtgtgaaataccgcacagatgcgtaaggagaaaataccgcatca
ggcggccttaagggcctcgtgatacgcctattttataggttaatgtcatgataataatggtttcttagacgtcaggtggcactttt
cggggaaatgtgcgcggaaccccctatttgtttattttctaaatacattcaaatatgtatccgctcatgagacaataaccctgat
aaatgcttcaataatattgaaaaaggaagagtatgagtattcaacatttccgtgtcgcccttattccctttttgcggcattttgcct
tcctgttttgctcacccagaaacgctggtgaaagtaaaagatgctgaagatcagttgggtgcacgagtgggttacatcgaa
ctggatctcaacagcggtaagatccttgagagttttcgccccgaagaacgttttccaatgatgagcacttttaaagttctgctat
gtggcgcggtattatcccgtattgacgccgggcaagagcaactcggtcgccgcatacactattctcagaatgacttggttga
gtactcaccagtcacagaaaagcatcttacggatggcatgacagtaagagaattatgcagtgctgccataaccatgagtg
ataacactgcggccaacttacttctgacaacgatcggaggaccgaaggagctaaccgcttttttgcacaacatgggggat
catgtaactcgccttgatcgttgggaaccggagctgaatgaagccataccaaacgacgagcgtgacaccacgatgcctgt
agcaatggcaacaacgttgcgcaaactattaactggcgaactacttactctagcttcccggcaacaattaatagactggat
ggaggcggataaagttgcaggaccacttctgcgctcggcccttccggctggctggtttattgctgataaatctggagccggt
gagcgtgggtctcgcggtatcattgcagcactggggccagatggtaagccctcccgtatcgtagttatctacacgacgggg
agtcaggcaactatggatgaacgaaatagacagatcgctgagataggtgcctcactgattaagcattggtaactgtcaga
ccaagtttactcatatatactttagattgatttaaaacttcattttaatttaaaaggatctaggtgaagatccttttgataatctcat
gaccaaaatcccttaacgtgagttttcgttccactgagcgtcagaccccgtagaaaagatcaaaggatcttcttgagatcctt
ttttctgcgcgtaatctgctgcttgcaaacaaaaaaaccaccgctaccagcggtggtttgtttgccggatcaagagctacca
actcttttccgaaggtaactggcttcagcagagcgcagataccaaatactgtccttctagtgtagccgtagttaggccacca
cttcaagaactctgtagcaccgcctacatacctcgctctgctaatcctgttaccagtggctgctgccagtggcgataagtcgt
gtcttaccgggttggactcaagacgatagttaccggataaggcgcagcggtcgggctgaacggggggttcgtgcacaca
gcccagcttggagcgaacgacctacaccgaactgagatacctacagcgtgagcattgagaaagcgccacgcttcccga
agggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcagggggggcg
gagcctatggaaaaacgccagcaacgcggccttttacggttcctggccttttgctggccttttgctcacatgttctttcctgcgtt
atcccctgattctgtggataaccgtattaccgcctttgagtgagctgataccgctcgccgcagccgaacgaccgagcgcag
cgagtcagtgagcgaggaagcggaagagcgcccaatacgcaaaccgcctctccccgcgcgttggccgattcattaatg
cagctggcacgacaggtttcccgactggaaagcgggcagtgagcgcaacgcaattaatgtgagttagctcactcattagg
cacccccaggctttacactttatgcttccggctcgtatgttgtgtggaattgtgagcggataacaatttcacacaggaaacagct
atgaccatgattacgccaagcttgcatgcctgcaggtcgactctagaggatcaagagcatttgaatcagaatatggagaac
ggagcatgagcattttcgaagttttttagatgcactagaacaaagcgtgttggcttcctctgagcccgctttccttatataccccg
cattctgcagccttacagaatgttctagaaggtcctagatgcattcgtttgaaaatactcccggtgggtgcaaagagacgca
gacggaaaatgtatctgggtctctttattgtgtacactacttttccatgtaccgaatgtgagtcgccctccttttgcaacaagcag
ctcgaatgttctagaaaaaggtggaaaatagtataaataccgttgaaaataaataccgaacaacatttgctctaattgtgaa
attagaaatcttcaaactataatcatctcactggatccccgggattggccaaaggacccaaaggtatgtttcgaatgatacta
acataacatagaacattttcaggaggacccttgg

*FIG. 2B*

Enhanced Vector for RNAi, producing sup35 dsRNA and dsRNA of the library, gene of interest or PCR product

CHARACTERIZATION OF GENE FUNCTION USING DOUBLE STRANDED RNA INHIBITION

The present invention is concerned with characterization or identification of gene function using double stranded RNA inhibition (dsRNAi) and methods of identifying DNA responsible for inducing a specific phenotype in a cell and a method of assigning function to known gene sequences.

It has recently been described in Nature Vol 391, pp. 806–811, February 98, that introducing double stranded RNA into a cell results in potent and specific interference with expression of endogenous genes in the cell and which interference is substantially more effective than providing either RNA strand individually as proposed in antisense technology. This specific reduction of the activity of the gene was also found to occur in the nematode worm *Caenorhabditis elegans* (*C. elegans*) when the RNA was introduced into the genome or body cavity of the worm.

The present inventors have utilized this technique and applied it further to devise novel and inventive methods of assigning functions to genes or DNA fragments, which have been sequenced in various projects, such as, for example, the human genome project and which have yet to be accorded a particular function and for use in identifying DNA responsible for conferring a particular phenotype.

Therefore, according to a first aspect of the present invention there is provided a method of identifying DNA responsible for conferring a phenotype in a cell which method comprises a) constructing a cDNA or genomic library of the DNA of said cell in an orientation relative to a promoter(s) capable of promoting transcription of said cDNA or DNA to double stranded (ds) RNA upon binding of an appropriate transcription factor to said promoter(s), b) introducing said library into one or more of said cells comprising said transcription factor, and c) identifying and isolating a desired phenotype of said cell comprising said library and identifying the DNA or cDNA fragment from said library responsible for conferring said phenotype.

In a preferred embodiment of the invention the library may be organised into hierarchical pools as described in more detail in the examples provided, prior to step b) such as to include, for example, gene families.

According to a further aspect of the invention there is also provided a method of assigning function to a known DNA sequence which method comprises a) identifying a homologue (s) of said DNA in a cell, b) isolating the relevant DNA homologue(s) or a fragment thereof from said cell, c) cloning said homologue or fragment into an appropriate vector in an orientation relative to a promoter(s) capable of promoting transcription of dsRNA upon binding of an appropriate transcription factor to said promoters, d) introducing said vector into said cell from step a) comprising said transcription factor, and e) identifying the phenotype of said cell compared to wild type.

In each aspect of the invention, the nucleotide or DNA sequence may either be provided in a sense and an antisense orientation relative to a single promoter which has the properties defined above, or alternatively it may be provided between two identical promoters. In both embodiments dsRNA is provided from the transcription initiated from the promoter following binding of its appropriate transcription factor.

The cell according to the invention may be derived from or contained in an organism. Where the cell is contained within an organism, the organism may be adapted to express the appropriate transcription factor. The organism may be any of a plant, animal, fungus or yeast but preferably may be the nematode worm *C. elegans*, which may be any of a wild type, a nuc-1 or pha-ts mutant of *C. elegans* or a combination of said mutations. In an alternative embodiment the DNA or cDNA library or the DNA homologue or fragment thereof may, advantageously, be transfected or transformed into a microorganism, such as a bacterial or yeast cell, which may be fed to the organism, which is preferably the nematode worm *C. elegans*. In this embodiment of the invention the microorganism may be adapted to express the appropriate transcription factor. Preferably, the microorganism is *E. coli*.

In each aspect of the invention, the DNA library, DNA homologue or DNA fragment may be constructed in a suitable DNA vector which comprises a sequence of nucleotides which encode said transcription factor. Alternatively, said transcription factor is encoded by a further vector. In an even further alternative, the cell or organism may express or be adapted to express said transcription factor. Preferably, any of the vectors used in the method according to the invention comprises a selectable marker which may be, for example, a nucleotide sequence encoding sup-35 or a fragment thereof. The nucleotide sequence may be orientated relative to a promoter such that binding of a transcription factor to the promoter initiates transcription of the DNA into double stranded RNA. FIG. 10 illustrates the vectors and the orientation of the DNA sequence which enable double stranded RNA production in *C. elegans*. Thus in one embodiment the DNA is located between two promoters on a vector capable of expressing dsRNA upon binding of an appropriate transcription factor to said promoters. Alternatively, the vector comprises two copies of the DNA sequence organised in a sense and antisense orientation relative to the promoter and which marker is selectable when contained in a pha-1 mutant *C. elegans*. Preferably, the promoters are any of T7, T3 or SP6 promoters and the transcription factor comprises the appropriate polymerase.

Preferably, the selectable marker comprises a nucleotide sequence capable of inhibiting or preventing expression of a gene in said cell and which gene is responsible for conferring a known phenotype. This nucleotide sequence may be part of or identical to said gene conferring said phenotype, and which nucleotide sequence is itself oriented relative to a suitable promoter(s) capable of initiating transcription of double stranded RNA upon binding of an appropriate transcription factor to said promoter(s). Alternatively, the nucleotide sequence may be a part of or identical to said gene sequence conferring said phenotype, and which nucleotide sequence is such as to permit integration of said suitable or further vector by homologous recombination in the genome of said cell and following said integration said nucleotide sequence is capable of inhibiting expression of said gene sequence conferring said phenotype. In this embodiment said nucleotide sequence comprises stop codons sufficient to prevent translation of said nucleotide sequence following its integration into said genome.

Compounds can, advantageously, in said method be added to said cell or organism for the purposes of screening for desired phenotypes, such as for example, resistance or sensitivity to the compound when compared to wild type. The promoters are preferably inducible. The transcription factor may in some embodiments be phage derived, such as for example, a T7 polymerase driven by a phage promoter. However, when *C. elegans* is utilised a worm specific or tissue specific promoter can be used, such as for example, let858, SERCA, UL6, myo-2 or myo-3. Preferably, the *E. coli* strain is an RNAaseIII and even more preferably an Rnase negative strain.

A further aspect of the present invention provides a method of generating a transgenic non-human organism comprising an exogenous transcription factor and a transgene comprising a promoter operably linked to DNA fragment which is expressed upon binding of said transcription factor thereto, the method comprising a) providing a first transgenic organism comprising a first construct incorporating DNA encoding an exogenous transcription factor and a second transgenic organism comprising a second construct including at least one promoter operably linked to a desired DNA sequence which is expressed upon binding of the transcription factor of said first transgenic organism thereto b) crossing said first and second transgenic organisms and selecting offspring expressing said desired DNA sequence. In one embodiment said first and second transgenic organisms are generated by transforming said first and second constructs into respective microorganisms for subsequent feeding to the respective organism. Preferably, said second construct comprises said desired DNA sequence in an orientation relative to said promoter so as to be capable of initiating transcription of said DNA to dsRNA upon binding of said transcription factor thereto. In this embodiment said second construct comprises two promoters flanking said desired DNA sequence which promoters can initiate transcription of said DNA sequence to dsRNA upon binding of said transcription factor to said promoters. Alternatively, said DNA sequence is provided in a sense and an antisense orientation relative to said promoter so as to produce dsRNA upon binding of the transcription factor to the promoters. In each of these embodiments the first and/or second constructs may preferably be provided with a reporter gene operably linked to a promoter which is capable of initiating transcription of said reporter upon binding of said transcription factor thereto. Preferably, the reporter gene encodes any of Luciferase, Green Fluorescent protein, β galactosidase or β-lactamase.

The present invention also includes a method of validating clones identified in yeast two hybrid vector experiments which experiments are well known to those skilled in the art and which experiments were first proposed by Chien et al. (1991) to detect protein—protein interactions. The method according to the invention comprises providing a construct including the DNA encoding a protein identified in a two hybrid vector experiment, which construct is such that said DNA is provided in an orientation relative to one or more promoters capable of promoting transcription of said DNA to double stranded RNA upon binding of an appropriate transcription factor to said promoters, transforming a cell, such as a bacterial cell or alternatively transforming an organism comprising said transcription factor with said constructs and identifying a phenotypic change in said cell or organism, which may be *C. elegans* or the like, compared to wild type. Preferably, the transcription factor is inducible in the cell or organism. Once again the DNA sequence may be located between two promoters or in both a sense and antisense orientation relative to a single promoter, as described above. Preferably, the promoter is a phage polymerase promoter and said transcription factor is a RNA polymerase, and preferably T7 polymerases. Also encompassed with the scope of the present invention are vectors used to transform said cells or organisms and the cells or organisms themselves.

In a further aspect of the present invention there is provided a method of alleviating pest infestation of plants, which method comprises a) identifying a DNA sequence from said pest which is critical either for its survival, growth, proliferation or reproduction, b) cloning said sequence from step a) or a fragment thereof in a suitable vector relative to one or more promoters capable of transcribing said sequence to RNA or dsRNA upon binding of an appropriate transcription factor to said promoters, and c) introducing said vector into the plant.

Thus, advantageously, the method according to the invention provides a particularly selective mechanism for alleviating pest infestation, and in some cases parasitic infestation of plants, such that when the pest feeds on the plant it will digest the expressed dsRNA in the plant thus inhibiting the expression of the DNA within the pest which is critical for its growth, survival, proliferation or reproduction. In a preferred embodiment, the pest may be any of *Tylenchulus* ssp. *Radopholus* ssp., *Rhadinaphelenchus* ssp., *Heterodera* ssp., *Rotylenchulus* ssp., *Pratylenchus* ssp., *Belonolaimus* ssp., *Canjanus* ssp., *Meloidogyne* ssp., *Globodera* ssp., *Nacobbus* ssp., *Ditylenchus* ssp., *Aphelenchoides* ssp., *Hirschmenniella* ssp., *Anguina* ssp., *Hoplolaimus* ssp., *Heliotylenchus* ssp., *Criconemella* ssp., *Xiphinema* ssp., *Longidorus* ssp., *Trichodorus* ssp., *Paratrichodorus* ssp., *Aphelenchs* ssp. The DNA sequence or fragment thereof according to this aspect of the invention may be cloned between two tissue specific promoters, such as two root specific promoters.

A further aspect of the invention concerns the vector used in each of the methods of the invention for constructing said library, which vector comprises two identical promoters oriented such that they are capable of initiating transcription of DNA sequence located between said promoters to dsRNA upon binding is of an appropriate transcription factor to said promoters. The DNA sequence may, for example, include a multiple cloning site. Preferably, the expression vector comprises a nucleotide sequence encoding a selectable marker. In one embodiment the nucleotide sequence encoding said selectable marker is located between two identical promoters oriented such that they are capable of initiating transcription of DNA located between said promoters to double stranded RNA upon binding of an appropriate transcription factor to said promoters. Preferably, the selectable marker comprises a nucleotide sequence encoding sup-35, for introduction into *C. elegans* having a pha-1 mutation.

Preferably, the transcription factor comprises either a phage polymerase which binds to its corresponding promoter or a *C. elegans* specific promoter and even more preferably T7 polymerase. Preferably, the vector includes a multiple cloning site between said identical promoters.

In a further aspect of the invention there is provided an expression vector for expressing an appropriate transcription factor for use in a method according to the invention which vector comprises a sequence of nucleotides encoding said transcription factor operably linked to suitable expression control sequences. Preferably, the expression control sequences include promoters which are inducible, constitutive, general or tissue specific promoters, or combinations thereof. Preferably, the transcription factor comprises a phage polymerase, and preferably T7, T3 or SP6, RNA polymerase.

A further aspect of the invention provides a selection system for identifying transformation of a cell or organism with a vector according to the invention which system comprises a vector according to the invention wherein said selectable marker comprises a nucleotide sequence capable of inhibiting or preventing expression of a gene in said cell or organism which gene is responsible for conferring a known phenotype. Preferably said nucleotide sequence corresponds to a part of or is identical to said gene conferring said known phenotype, and which nucleotide sequence is itself located between two identical promoters capable of initiating transcription of double stranded RNA upon binding of an appropriate transcription factor thereto. Alternatively, the nucleotide sequence comprises a nucleotide sequence which is a part of or identical to said gene sequence which confers a known phenotype on said cell or organism, and which is such that following integration of said vector by homologous recombination in the chromosome of said cell or organism said sequence inhibits expression of said gene sequence conferring said known phenotype. Preferably, according to this embodiment the nucleotide sequence comprises stop codons sufficient to prevent translation of the nucleotide sequence following integration into said chromosome. Preferably, the known gene sequence comprises a sup-35 gene or a fragment thereof which is selectable by identifying offspring growing at a temperature above 25° C. following introduction in a pha-1 et123ts mutant *C. elegans* worm.

In a further aspect of the invention provides said known gene sequence comprises a sup-35 gene or a fragment thereof which is selectable by identifying offspring growing at a temperature above 25° C. following introduction of said vector in a pha-1 et123ts mutant *C. elegans* worm. An even further aspect comprises a method of assigning function to a DNA sequence of a multicellular organism which method comprises a) providing i) a construct comprising said DNA fragment cloned between two promoters capable of promoting transcription in said multicellular organism, in a multicellular organism capable of initiating transcription from said promoter; b) identifying the phenotype of said multicellular organism compared to wild type.

The present invention may be more clearly understood by the following examples which are purely exemplary with reference to the accompanying figures, wherein:

FIG. 1 is a nucleotide sequence of plasmid PGN1 in SEQ ID NO: 1 accordance with the present invention.

FIG. 2 is a nucleotide sequence of plasmid PGN100 SEQ ID NO: 2 in accordance with the present invention.

EXAMPLE A

Figure 3:
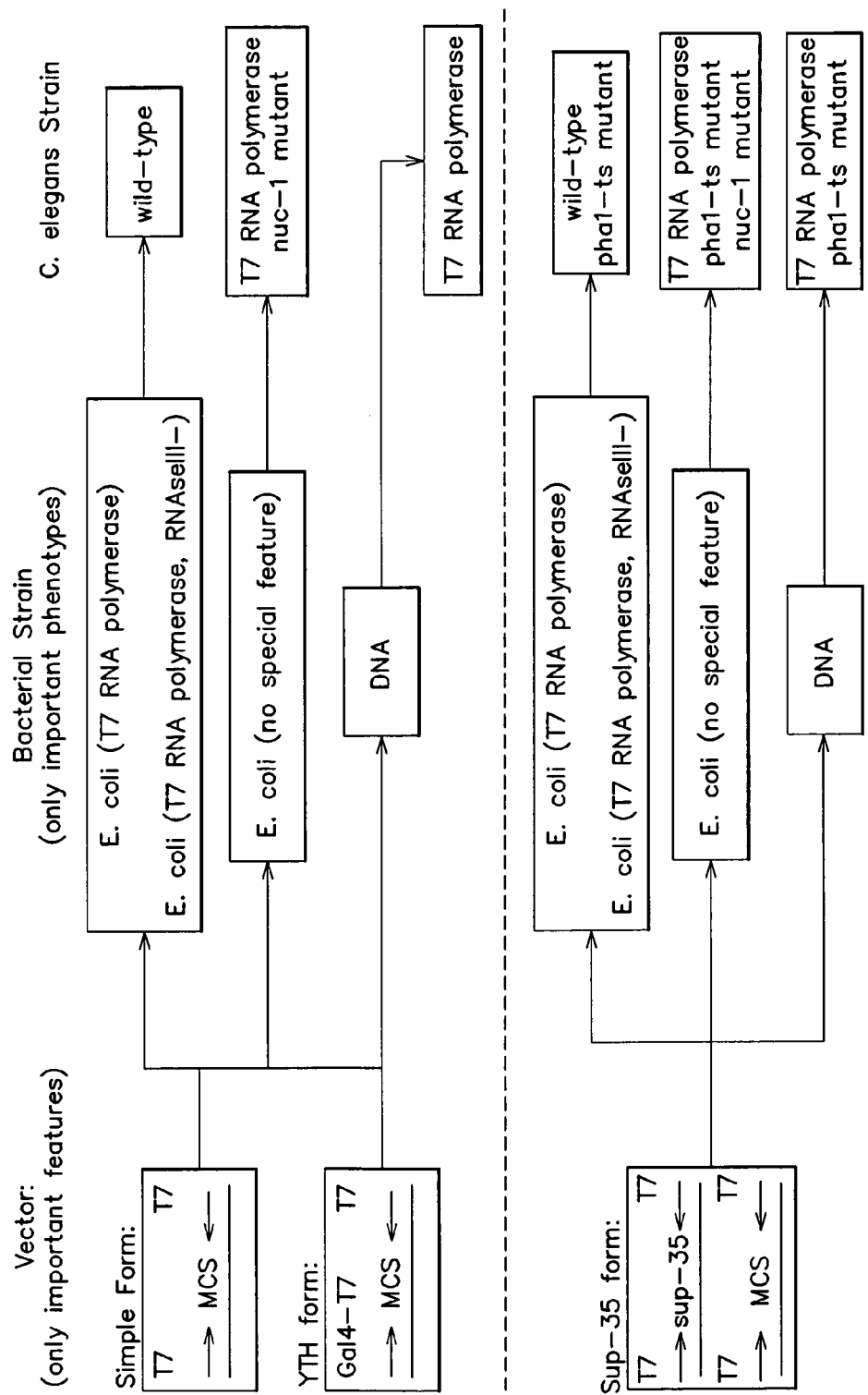
FIG. 3 is a schematic representation of the vectors used and the transformation regime used in the methods according to the present invention.
Figure 4:
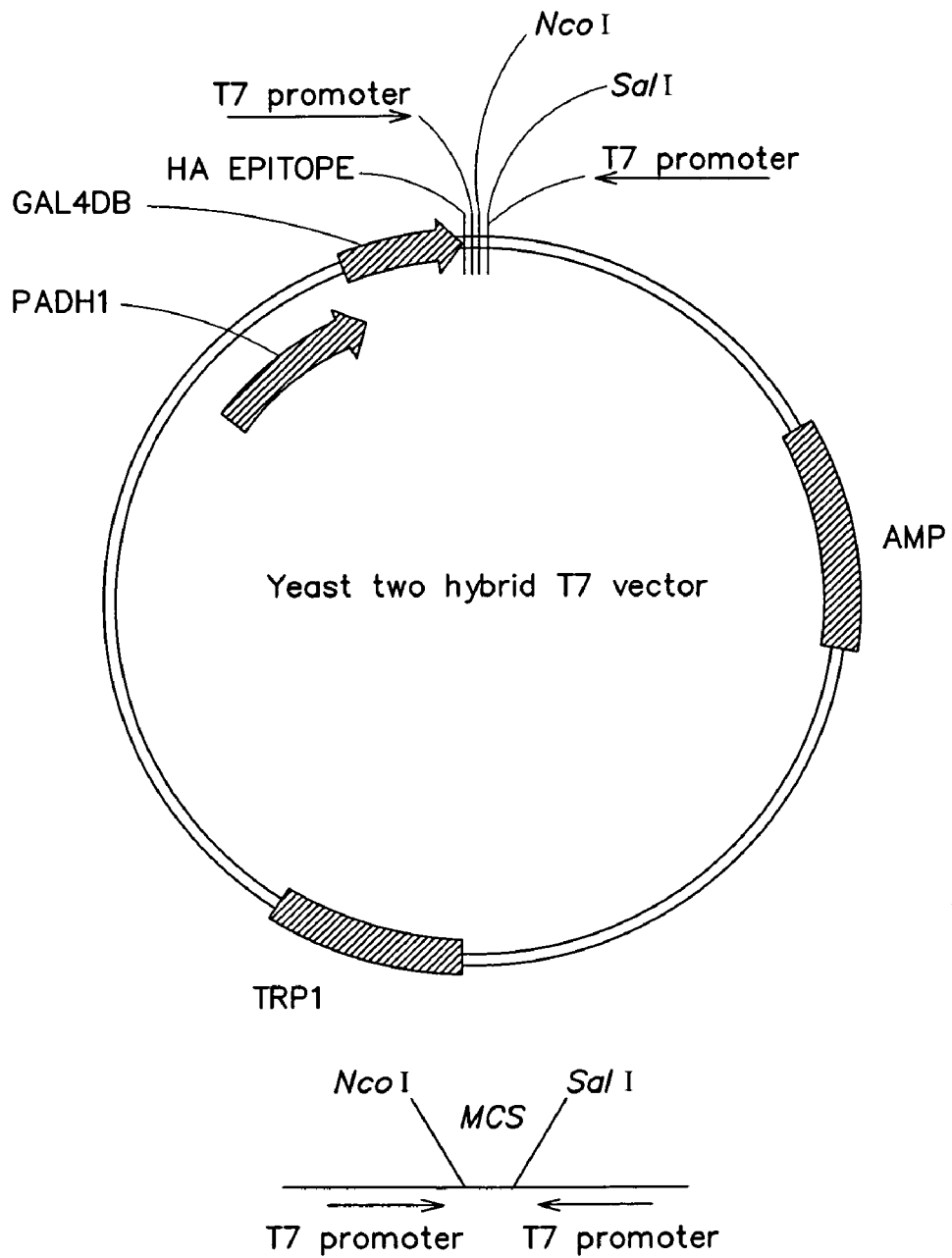
FIG. 4 is an illustration of an expression vector used in accordance with the invention.
Figure 5:
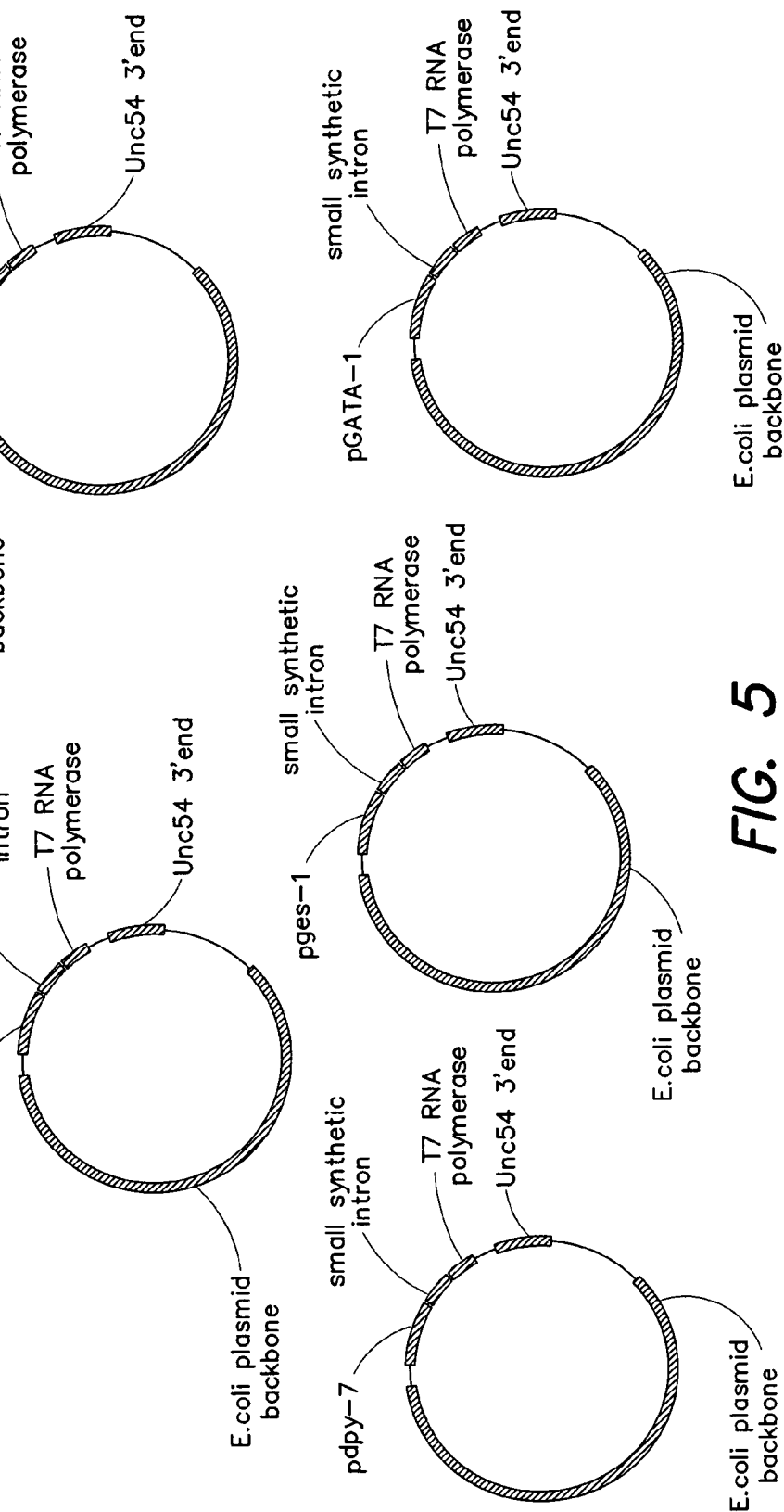
FIG. 5 is a schematic illustration of the T7 RNA polymerase expression vectors used for transforming *C. elegans*.
Figure 6:
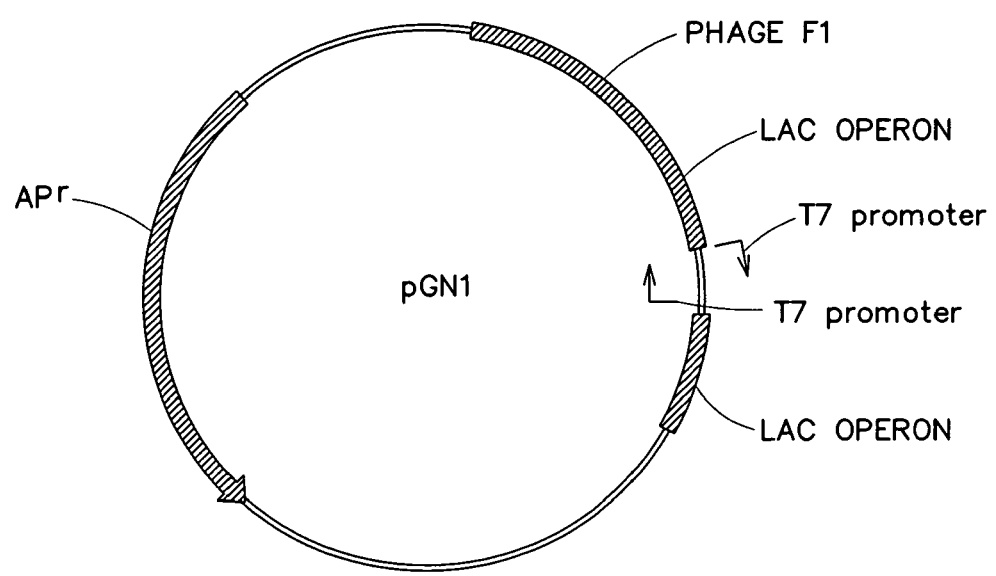
FIG. 6 is an illustration of plasmid PGN1.
Figure 7:
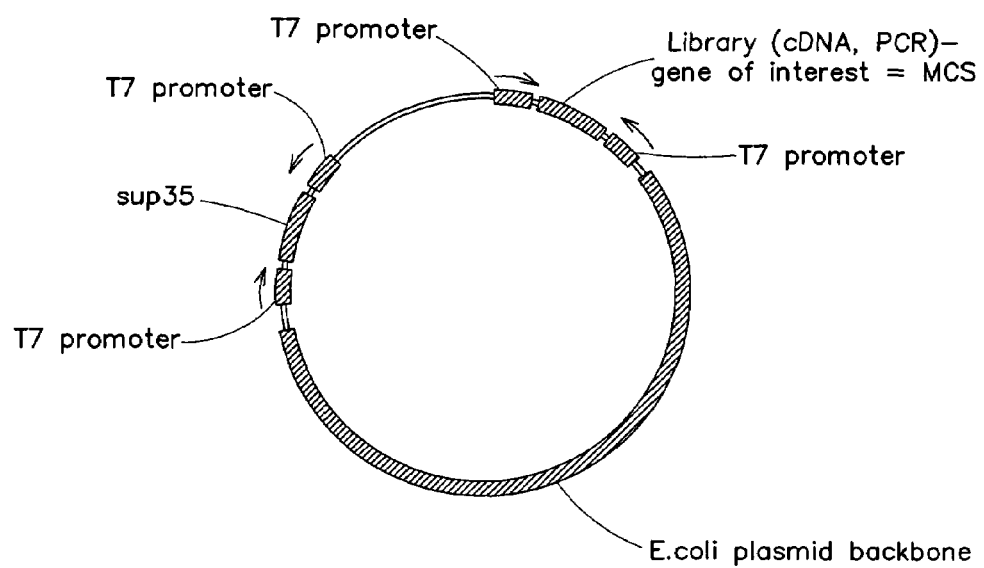
FIG. 7 is a diagrammatic representation of an enhanced vector for dsRNA inhibition encoding sup-35 dsRNA.

Construction of an Ordered and Hierarchical Pooled cDNA Library and Applications Thereof A Random Ordered and Pooled Library:

The vector is an *E. coli* vector harboring two T7 promoters, with a multiple cloning site (MCS) in between. The two promoters are orientated towards each other, and towards the MCS. In the presence of T7 RNA polymerase, expressed in *E. coli*, *C. elegans* or any other organism, RNA will be produced, starting from the two T7 promoters. As these are oriented in the opposite sense, both strands of RNA will be produced from the DNA inserted (cloned) into the MCS in between the two promoters which results in the generation of double stranded RNA (dsRNA) upon binding of the T7 RNA polymerase thereto.

A *C. elegans* cDNA library is constructed in the MCS using standard molecular biological techniques. The library is transformed into *E. coli*, and the resulting *E. coli* are grown in culture and stored in 96 multi-well plates. At this stage, plasmid DNA can be isolated and stored in 96-multi-well plates corresponding to those of the *E. coli* colonies. Approximately 100,000 colonies are scored. In this way, the library will harbor approximately 5 times the total expressed cDNA variation of *C. elegans*, which gives the opportunity for low expressed sequences to be present in the library. This will result in approximately 1041 96-well plates. The plates are hierarchical pooled as necessary. For the present pooling of the clones is arranged in a range of 10 to 100. If the hierarchical pooling is per 8 or 12 (numbers are more convenient as 96-well plates have a 8 to 12 grid), this will result in approximately 87 multi-well plates and approximately 8352 wells. If hierarchical pooling is per 96 wells, which is a full plate, this results in approximately 11 plates and approximately 1041 wells. At any stage of the hierarchical pooling, plasmid DNA can be isolated, which would be less elaborate as less plates are used, but will result in a loss of complexity although this should not be the case in the pooling per 12. The pooling of the DNA can also be carried out with the original DNA.

The experiments below describe how the hierarchical pooling should be performed, both for the DNA and for the *E. coli* library.

An Ordered Library for RNAi Technology, Harboring Every Gene of the *C. elegans* Genome, with Applications Thereof As the genome-sequencing project is coming to an end, this information can be used in the application of T7 RNA inhibition technology. Every gene of the *C. elegans* genome can be cloned using PCR technology. In preference, exons will be cloned with a minimal length of 500 bp. If the exons are too small, smaller fragments will be isolated with PCR, or even parts of introns and neighboring exons will be isolated with PCR technology so that at least a sufficient part of the translated region of the gene is cloned. For this, at least 17000 PCR reactions need to be performed. This collection of PCR products will be cloned in a T7 vector as described (two T7 promoters oriented towards each other with a multiple cloning site in between). Every PCR product is cloned independently, or can be used to generate a random library, analogous to the described cDNA library. If every PCR product is cloned individually, the resulting bacteria and plasmid DNA can be pooled in various ways. Firstly, this collection of individually cloned PCR products in the T7 RNAi vector can be pooled randomly, as described in the random library This pooling can also be done in a more rational way. For instance, the genes of the *C. elegans* genome can be analyzed using bioinformatic tools (in silico biology). Various genes of the genome will belong to a gene family, or will have homologues in the genome. These members of the gene family will be pooled, or the members, being homologues will be pooled. In this way the total number of about 17000 clones is reduced to a more useable quantity. This library can be used to screen for phenotypes in the methods according to the invention. The resulting phenotype gives a functional description to the gene or gene family or gene homologues of the *C. elegans* genome. As the library consists of a part of every gene in the genome, this method enables description of the full genome in functional-phenotypic terms. For this the double stranded RNA (dsRNA) needs to be introduced in the worm. This introduction of clones alone, or pooled clones, being random pooling or rational pooling can be achieved in several ways as described.

Example of a Vector for the Expression of Double Stranded RNAi

Any vector containing a T7 promoter may be used, and which contains a multiple cloning site (there are many commercially available). Primers containing the complementary strand, both with the appropriate ends are designed. These primers can be hybridized, and if well designed, cloned in the vector of choice. The minimal sequence for a T7 promoter is TAATACGACTCACTATAGGGCGA (SEQ ID NO: 12). Although any vector can be used for the construction of a T7 expression vector there follows an example of how to achieve this with the vector pGEM-3zf (−).

Vector pGEM-3zf(+) (PROMEGA) was digested with HindIII and SalI

Primers oGN1 and oGN2 were mixed together at a final concentration of 1 µg/30 µl boiled and cooled slowly to room temperature.

The primer was ligated into the vector using standard ligation procedures. The resulting vector is pGN1 (shown in FIG. 1) and contains two T7 promoters oriented towards each other, and harbors a multiple cloning site in between.

Sequences of oGN1 and oGN2 are:

oGN1: AGC TGT AAT ACG ACT CAC TAT AGG GCG AGA AGC TT (SEQ ID NO:13)

oGN2: TCG AAA GCT TCT CGC ATA ATA GTG AGT CGT ATT AC (SEQ ID NO:14)

Example of the Construction of a Library

RNA may be isolated from every organism that is sensitive to RNAi. In general the isolated RNA is then copied into double stranded cDNA, and subsequently prepared in suitable vectors for cloning. Several procedures exist and molecular biology kits can be purchased from various firms including promega, clontech, boehringer Mannheim, BRL, etc which enable:

isolation of RNA, eventually polyARNA can be isolated (several techniques and kits available)

first strand synthesis with AMV reverse transcriptase, random hexameric primers and/or oligo (dT) primer second strand synthesis with Rnase H, DNA PolymeraseI, flush ends with T4 DNA Polymerase addition of an adaptor with T4 DNA ligase.

eventually treatment with T4 polynucleotide Kinase cloning of the cDNA into the vector.

The resulting ligation mixture can be considered as the cDNA library. The ligation contains all cDNA of the procedure ligated into the vector of interest. To order the library, the ligation needs to be transformed into *E. coli* strains.

Application of this *E. coli* or DNA Library

T7 RNA Producing Strain:

a standard strain is BL21 (DE3): F-ompT[lon]hsds(r-m-; and *E. coli* B strain) λ (DE3). Eventually variants of BL21 (DE3) can be used, although BL21 (DE3)pLysS is used.

any other *E. coli* strain which produces the T7 RNA polymerase, which may be available needs to be constructed. This can be generated easily using a phage, which is commercially available, in this case, the λCE6 vector (provided by Promega) is used. Almost every *E. coli* strain can be transfected with this phage and will produce T7 RNA polymerase.

a RNAseIII mutant *E. coli*:

Various strains are in principle available, we chose in a first experiment to use strain AB301-105: rna-19, suc-11, bio-3, gdhA2, his95, rnc-105, relA1, spoT1, metB1. (Kinder et al. 1973 Mol. Gen. Genet 126:53), but other strains may suit better. This strain is infected with λCE6 and so a T7 producing variant will be constructed.

Wild type *C. elegans* worms can be grown on the bacteria pools. The bacteria is expressing the T7 RNA polymerase. This results in large quantities of dsRNA in the gut of the *C. elegans*, which will diffuse in the organism and results in the inhibition of expression. This library can now be used for the screening of several phenotypes. This technique has the advantage that it is a much faster to detect relevant genes in certain pathways, than the known *C. elegans* technology. Moreover, if an interesting phenotype is found, the responsible gene can be cloned easily.

Using the hierarchical pooling one can easily find in a second screen the relevant clone of the pool. The inserted DNA of this clone can then be sequenced. This experiment results in genetic and biochemical DATA in one step.

Wild type *C. elegans* strains can be combined with compounds to screen for phenotype, drug resistance and or drug sensibility. The *C. elegans* strain can be a mutant strain, screening for an enhanced phenotype, reduced phenotype, or a new phenotype. The *C. elegans* strain can be a mutant strain, and the library screen can be combined with compounds. So one can screen for drug resistance, drug sensibility, enhanced phenotype, reduced phenotype, or a new phenotype. The *E. coli* strain may be any T7 RNA polymerase expressing strain, like BL21 (DE3), for example, but the formation of double strand RNA may be enhanced by using a special *E. coli* strain that is RNAseIII negative. RNAseIII recognizes specific loops in dsRNA. Eventually, an *E. coli* strain can be used that is deleted in RNAses other than RNAseIII or an *E. coli* can be used that is deleted in one or more RNAses. The expression of the T7 RNA polymerase in most known *E. coli* strains and constructs which are available to generate T7 RNA polymerase producing *E. coli* strains, generally comprise an inducible promoter. In this way the production of the T7 RNA polymerase is regulated, and thus the production of the dsRNA. Advantageously, this feature can be used to "pulse" feed the *C. elegans* worms at specific stages of growth. The worms are grown on the non-induced *E. coli* strains. When the worm has reached the stage of interest, the T7 RNA production in the bacteria is induced. This allows the studying of the function of any gene at any point in the life cycle of the animal.

Screening the Library for Homologues of Putative Interesting Human Genes, and Assign Function to these Genes Hundreds of genes have been isolated in various projects, being genomic projects, differential expressed arrays, hybridization studies, etc. The described cDNA library can provide a way to validate and or assign function to these genes in a fast and efficient manner. First of all the worm homologue or homologues or the genes need to be identified by bioinformatic tools (in silico biology) PCR primers are developed and the cDNA fragment is isolated using PCR technology. PCR can be performed on the hierarchical pools. The positive pool or individual wells harboring the bacteria that has the appropriate cDNA is fed to C. elegans and the phenotype is scored.

PCR can be performed on cDNA isolated from C. elegans. The resulting DNA can be cloned in the T7 vector and transformed in the dsRNA producing E. coli on which the C. elegans worms are then fed. Depending on which way is faster and more reliable a choice needs to be made.

If the gene belongs to a gene family, the worm may need to be fed on a mixture of bacteria. Each of them harboring a part of the member of the gene family. E. coli strains, growth conditions, combinations with compounds can be performed as described above.

If the library rational is used, in which all the genes of C. elegans are cloned in a organized and structured way, the C. elegans homologue and eventually the other homologues, orthologues, and members of the gene family can be traced back easily in the library using a silico biology. No PCR is involved in this step, and the bacteria and or DNA can be isolated on which the worm will be grown.

EXAMPLES

The idea of the series of experiments was to test both the RNAi vector and the various E. coli strains that were constructed.

1) Construction of a Test Plasmid

Any cDNA that gives a clear phenotype in the worm when knocked-out, or used in a RNAi experiment can be used. It is known that unc-22 is a good candidate, but may other genes are possible. We opted for a sensitive system that can be used at a later stage. The system was tested with sup-35 in a pha-1 background. Exon 5 of the sup-35 was isolated by PCR and cloned in the T7 promoter vector pGN1. The resulting vector was designated pGN2. pha-1 (e2123) mutant worms cannot produce offspring at temperatures higher than 25° C. This is due to a developmental problem in embryogenesis. When sup-35 is knocked-out, or inhibited in this strain, offspring may grow at this temperature. Combination of pha-1 mutant worms and sup-35 RNAi is a good system to validate the various options.

2) Testing the RNAi Using an E. coli Strain that Produces dsRNA.

pGN2 was introduced in E. coli strain strain BL21(DE3) and T7 RNA polymerase was induced with IPTG. C. elegans worms (pha-1 (e2123)) were inoculated on this bacteria, and grown at the restricted temperature of 25° C. As this mutant is an embryonic mutant at this temperature, no offspring will be observed. If the sup-35 gene is efficiently inhibited by the dsRNA present in the E. coli, offspring will be observed.

pGN2 was introduced in E. coli strain AB301-105(DE3) and T7 RNA polymerase was induced with IPTG. C. elegans worms (pha-1 (e2123)) were inoculated on this bacteria, and grown at the restricted temperature of 25° C. As this mutant is an embryonic mutant at this temperature, no offspring will be observed. If the sup-35 gene is efficiently inhibited by the dsRNA present in the E. coli, offspring will be observed.

3) Improving the worm strain for better uptake of dsRNA.

Before plating the pha-1 C. elegans on the E. coli strain that produce the double stranded sup-35 RNA. The worm was mutagenised with EMS (Methane sulfonic Acid Ethyl). The offspring of this mutagenised worm is then plated on the bacteria. The worm that feed on this bacteria give larger offspring which has a mutation that results in an improvement of dsRNA uptake, and can be used for further experiments.

Figure 8:
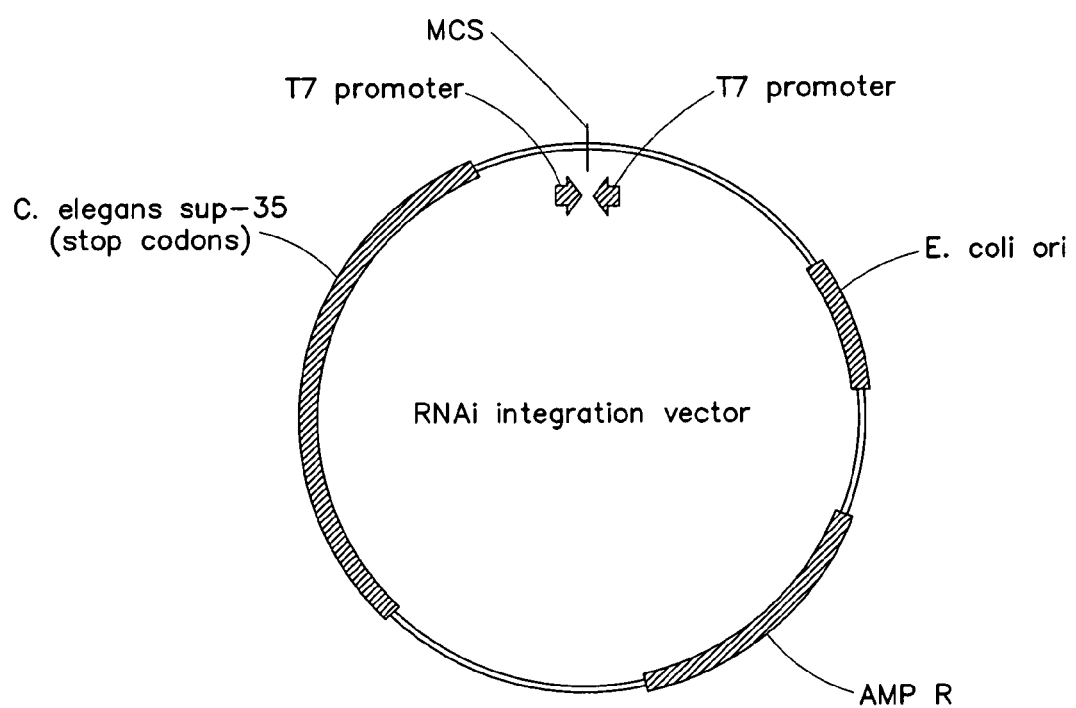
FIG. 8 is an illustration of a vector for integration into the genome of *C. elegans*.
Figure 9:
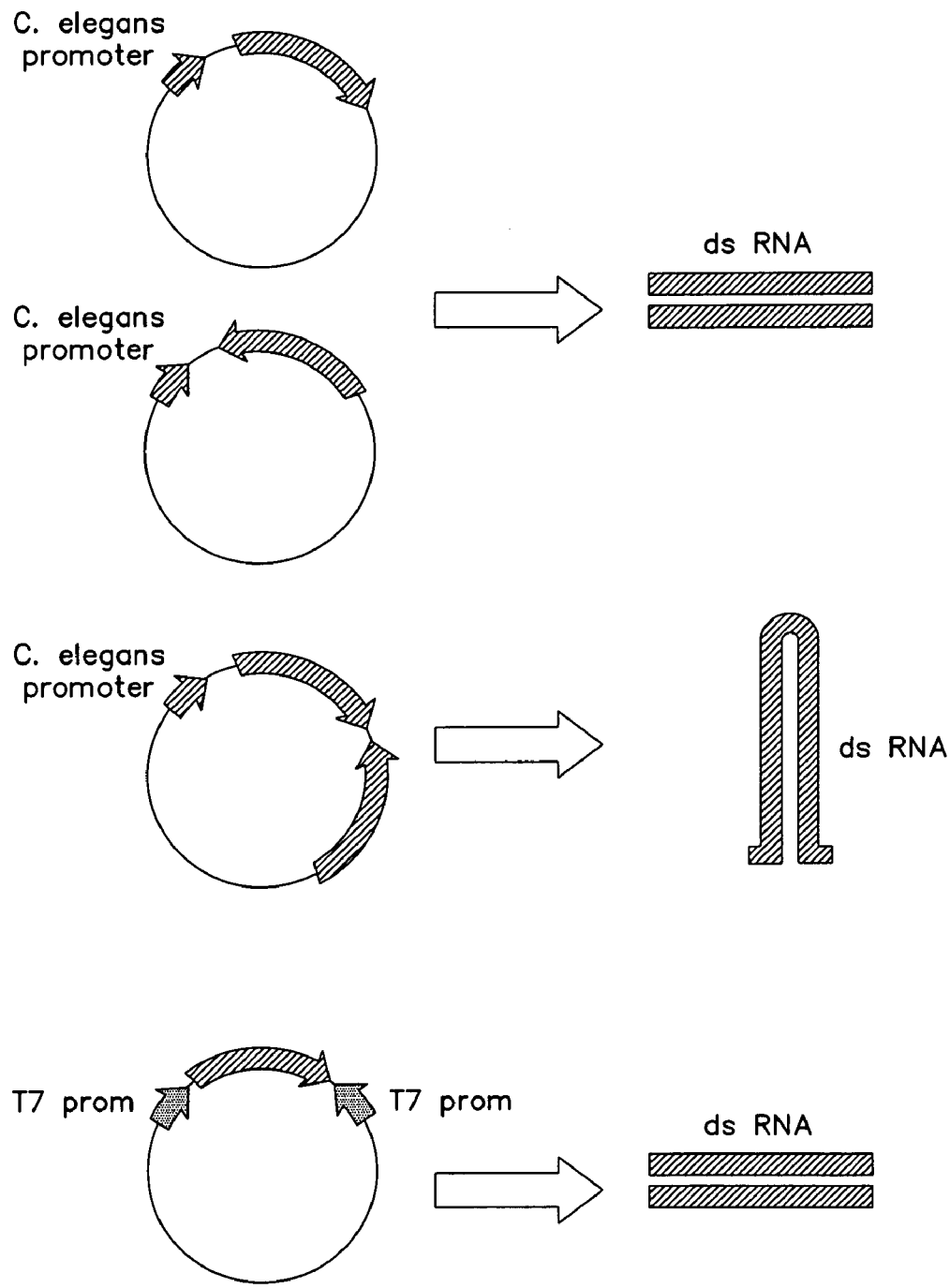
FIG. 9 is an illustration of the position of a DNA sequencers) relative to a suitable promoter to initiate expression of dsRNA from the DNA sequence(s).

Stable Integration of the dsRNA Producing Vector into the Genome of the T7 RNA Polymerase Producing Worm An E. coli vector can be constructed harboring the following features; Two T7 promoters directed towards each other, with a restriction site or a multiple cloning site in between. Furthermore, the vector may contain the C. elegans sup35 genomic DNA, engineered in such a way that it contains several stopcodons at various intervals, so that no full length protein can be expressed form the sup35 genomic DNA fragment as illustrated in FIG. 8. Any cDNA or cDNA fragment can be cloned in the multiple cloning site between the two T7 promoters. When this vector is introduced in a C. elegans strain which expresses T7 RNA polymerase, the cDNA or DNA fragment cloned between the two T7 promoters will be transcribed, generating dsRNA from the cloned fragment.

The vector is designed to be used in pha-1 (e2123) mutant worms expressing T7 RNA polymerase. The expression of the T7 RNA polymerase may be constitutive or regulated, general or tissue specific. These pha-1 (e2123) worms cannot produce offspring at temperatures higher than 25° C., which is due to a development problem in embryogenesis. When sup-35 is inhibited or knocked-out in this stain, offspring may grow at this temperature.

When the vector is introduced in the worm, the vector may integrate by homologous recombination (Campbell-like integration). It has been shown that homologous recombination occurs in C. elegans, although at low frequencies (Plasterk and Groenen, EMBO J. 11:287–290, 1992). Homologous recombination at the sup35 gene will result in a knock-out of the gene as the two resulting sup-35 genes will harbor the stopcodons. The resulting worm, and its offspring, if this recombination happens in the eggs, will have a copy of the vector integrated in the genome. This can be selected as only the worms for which the sup-35 has been knocked-out will have offspring at temperatures higher than 25° C. Furthermore, the resulting worm will stably produce double stranded RNA from the DNA fragment cloned between the two T7 promoters. This worm can now be considered as a stable transgenic worm strain with a reduction of function of the gene, from which a fragment has been cloned between the two T7 promoters.

The DNA may be delivered to the worm by several techniques, including injection, ballistic transformation, soaking in the DNA solution, feeding with bacteria. New and other methods that increase the transformation efficiencies can be considered.

The target C. elegans strain may in addition, have other mutations than the pha-1 (e2123) mutation, and may express other genes than T7 RNA polymerase.

Example B

A Yeast Two-Hybrid-RNAi Vector

A yeast two hybrid vector can be constructed harboring the two T7 promoters. The vectors can be designed to replicate both in yeast and in *E. coli*. In general cDNA libraries for the yeast two hybrid system are made in the Gal4 or LexA vectors. The library is constructed in vectors having the activation domain of one of these genes. A vector can be constructed that can still perform in the yeast two hybrid screen but which also contains two T7 promoters orientated towards each other, with a cloning site therein between. The order of the sequences in the plasmid will then be "plasmid backbone, (GAL4-T7), MCS, T7, backbone". A *C. elegans* cDNA library constructed in this vector can be used as a standard yeast two hybrid library in an experiment to isolate interacting proteins with a given protein. Once a clone is isolated, the plasmid can be introduced in an *E. coli* strain expressing the T7 RNA polymerase, and hence will produce dsRNA of the cloned fragment. The bacteria producing this dsRNA can be fed to the worm and phenotypes can be scored. As in the previous example, this validation procedure for a newly isolated yeast two hybrid clone is remarkably shorter than the standard procedure, which requires PCR and/or cloning steps, RNA experiments and/or knock-out experiments. In most cases isolated clones are sequenced first, and on the basis of the sequence, a decision is made to continue with further experiments. In the present invention every isolated clone can easily be introduced into the appropriate *E. coli* and fed to the worm. Validation is then performed by phenotype analysis.

To apply this procedure a yeast two hybrid was performed using a known gene as bait and the newly constructed library as the target. Proteins coded by the clones in the target that interact with the bait protein, will result in positive yeast clones expressing the reporter molecule such as can be observed by LacZ staining with X-gal. The plasmid coding for the target protein is isolated directly from the yeast strain and introduced in *E. coli*. The *E. coli* is T7 RNA polymerase producing *E. coli*. In this case, double stranded RNA is produced from the DNA cloned in the multiple cloning site of the vector. When this dsRNA is fed to the worm using the methods described previously, the gene has inhibited in the worm, resulting in a particular phenotype.

This yeast two hybrid vector can advantageously be used to construct an ordered and hierarchically pooled library as described in the previous example.

A yeast strain can also be constructed that conditionally produces T7 RNA polymerase. After yeast two hybrid experiments, the expression of the T7 polymerase could be induced, resulting in the production of dsRNA in the yeast cell. Consequently the yeast could be fed to the worm. Evidence is available showing that the *C. elegans* worms can feed on yeast.

Construction of a T7 RNA Polymerase Producing Strain, and Applications Thereof

A *C. elegans* strain can be constructed that expresses T7 RNA polymerase. The expression can be general and constitutive, but could also be regulated under a tissue specific promoter, an inducible promoter, or a temporal promoter or a promoter that harbors one of these characteristics or combination of characteristics. DNA can be introduced in this *C. elegans* strain. This is done either by injection, by shooting with particles, by electroporation or as aforementioned by feeding. If the DNA is a plasmid as described in the previous examples, i.e. a plasmid harboring a cloned cDNA fragment or a PCR fragment between two flanking T7 promoters, then dsRNA of this cDNA or PCR fragment is formed in the cell or whole organism resulting in down regulation of the corresponding gene. The introduced DNA can have an efficient transient down regulation. The introduced DNA can form an extrachromosomal array, which array might result in a more catalytic knock-out or reduction of function phenotype. The plasmid might also integrate into the genome of the organism, resulting in the same catalytic knock out or reduction of function phenotype, but which is stably transmittable.

Plasmid DNA harboring a cDNA or a part of a cDNA or an EST or an PCR fragment of *C. elegans* cloned between two T7 promoters as described in Examples A) and B) can be introduced in the T7 RNA polymerase worm, by standard techniques. Phenotypes can be analysed—DNA from an ordered and pooled library as in Example A) can be introduced in the T7 RNA polymerase worm, by standard techniques (injection, shooting). Phenotypes can be analysed. With the hierarchical pool, the original clone can be found easily.

The same procedure can be performed with a mutant worm expressing the T7 RNA polymerase. Screening for enhanced, reduced or new phenotypes.

The procedure can be used to enable screening of compounds. Screening with either a wild-type strain or a mutant strain for enhanced or new phenotypes.

The DNA could be introduced in the worm by new methods. One of which is the delivery of DNA by *E. coli*. In this case the hierarchical pooled library is fed to the animal. To prevent digestion of the *E. coli* DNA in the gut of the nematode, preferentially a DNAse deficient *C. elegans* will be used, such as nuc-1 (e1392). This procedure would be one of the most interesting as it would be independent of transformation efficiencies of other techniques, and generally faster and less labourious.

2) Putative enhancements of the method.

A vector is designed, so that it harbors the sup-35 cDNA or a part of this cDNA, cloned in between two T7 promoters. The rest of the vector is as described in Examples A) and B). This vector can be introduced into a pha-lts mutant *C. elegans*. A temperature selection system exists in this case and only those worms which have taken up the DNA and express the double stranded sup-35 RNA will survive at restricted temperatures. The hierarchical pooled library can be delivered by any method described above.

The vector can be used to construct a library that is introduced in a T7 RNA polymerase expressing *E. coli*. In this case we have an analogous screening as in part A) with an additional screening for worms where the dsRNA of sup-35 is active.

The DNA and or dsRNA of sup-35 could be delivered on a different plasmid. For the feeding, both DNA feeding (Example C) or dsRNA feeding Example A) and B), this means that the two plasmids could be present in one bacterium, or that the worm is fed on a mixture of bacteria, one of which harbors the sup-35 construct.

Example of the Construction of a T7 RNA Producing *C. elegans*

To produce T7 RNA polymerase in the worm, several possibilities are possible. The T7 polymerase can be expressed under various promoters, being inducible promoters, constitutive promoters, general promoters and tissue (cell) specific promoters, or combinations of those. Examples of these promoters are the heatshock promoter hsp-16, the gut promoter ges 1, the promoter from cet858, but also the promoter of dpy 7 and the promoter element GATA1. In this example the T7 RNA polymerase is expressed under the control of the hsp-16 promoter that is available in the pPD49.78 vector. The T7 RNA polymerase is isolated as a PCR product using the primers of GN3 an GN4.

The resulting PCR product is digested with NheI and NcoI, as is the vector in which we want to clone, being the Fire vector pPD49.78. The resulting vector is pGN100 illustrated in FIG. 2 oGN3: CAT GGC AGG ATG AAC ACG ATT AAC ATC GC (SEQ ID NO:15); oGN4: ATG GCC CCA TGG TTA CGG GAA CGC GAA GTC CG (SEQ ID NO:16) pGN100 is included.

The vector is introduced into the worm using standard techniques, such as micro injection, for example.

The following strains were then constructed:
Wild-type (pGN100)
nuc-1 (e1392) (pGN100)
pha-1 (e2123) (pGN100)
pha-1; nuc-1 (pGN100)

All of these strains are able to produce T7 RNA polymerase when temperature induced or alternatively by metals such as application of heavy cadmium or mercury. The procedure for temperature induction is to shift the animal to a temperature of 30–33° C. for at least one hour, then the animal can be shifted back to standard temperatures (15–25° C.).

The wild type strain producing T7 RNA polymerase can be used for the production of any RNA in the worm. More specifically, the plasmids from the described libraries can be introduced in these worms, and phenotypes can be scored.

The nuc-1 mutant worm will be used to introduce DNA via bacteria on which the worm feed. As the nuc-1 worm does not digest the DNA, the plasmid DNA can cross the gut wall. If taken up by the cells that produce the T7 RNA polymerase, dsRNA will be produced thus inhibiting the gene from which the RNA was transcribed.

The pha-1 mutant strain that produced T7 RNA polymerase can be used to enhance the procedures as described above. DNA can be introduced by shooting, micro injection or feeding. More specifically this strain can be used for the vectors that produce dsRNA from sup-35 and from the gene of interest, the latter can be a PCR product, a cDNA, or a library as described.

The pha-1; nuc-1 mutant producing T7 RNA polymerase can be used for the bacterial delivery of the DNA. DNA will preferentially be the plasmid that produce dsRNA from both sup-35 and the gene of interest. The worm strain will preferentially produce the T7 RNA polymerase in the gut. Delivery will preferentially happen by feeding the worm on bacteria harboring the plasmid.

Application of the RNAi Technology in Plants

Nematodes are responsible a large part of the damage inflicted on plants and more particularly to plants used in the agricultural industry. The RNAi procedures according to the invention can be applied to plants to prevent these parasitic nematodes from feeding longer. In a first step, a DNA fragment is isolated from the parasitic plant nematode that is critical for the animals survival or growth, or to feed or to proliferate. Any gene from which the expression is essential is suitable for this purpose.

A part of this gene, an exon or cDNA is cloned. This DNA fragment can be cloned under the influence of a tissue specific promoter preferably a root specific promoter even more preferably between two root specific promoters. The DNA of the cloned gene under the control of the root specific promoter can be introduced in the plant of interest, using plant transgenic technology. For every parasitic nematode, a different piece of DNA may be required and likewise for every plant race, a different promoter will be needed.

The root will produce RNA or dsRNA from the introduced piece of DNA when root specific promoter is utilised. As the nematode feeds on the plant, the RNA and/or dsRNA will be consumed or ingested by the nematode. The RNA and/or dsRNA can enter the cells of the nematode and perform its inhibitory action on the target DNA. Depending on the nature of the cloned DNA piece of worm, the nematode will not be able to survive, to eat, proliferate, etc in any case preventing the animal of feeding longer on the plant, and thus protecting the plant.

Construction of a T7 RNA-Polymerase Producing *C. elegans*

To produce a T7 RNA polymerase or other RNA polymerases in animals, and more particularly in nematodes and most particularly in *C. elegans*, several possibilities can be envisaged. The T7 RNA polymerase can be expressed under various promoters. These promoters may be inducible promoters, constitutive promoters, general promoters, tissue specific promoters, or combinations of those.

Example 1

Construction of a Basic Vector for Expression of T7 Polymerase in *C. elegans*

Figure 11:
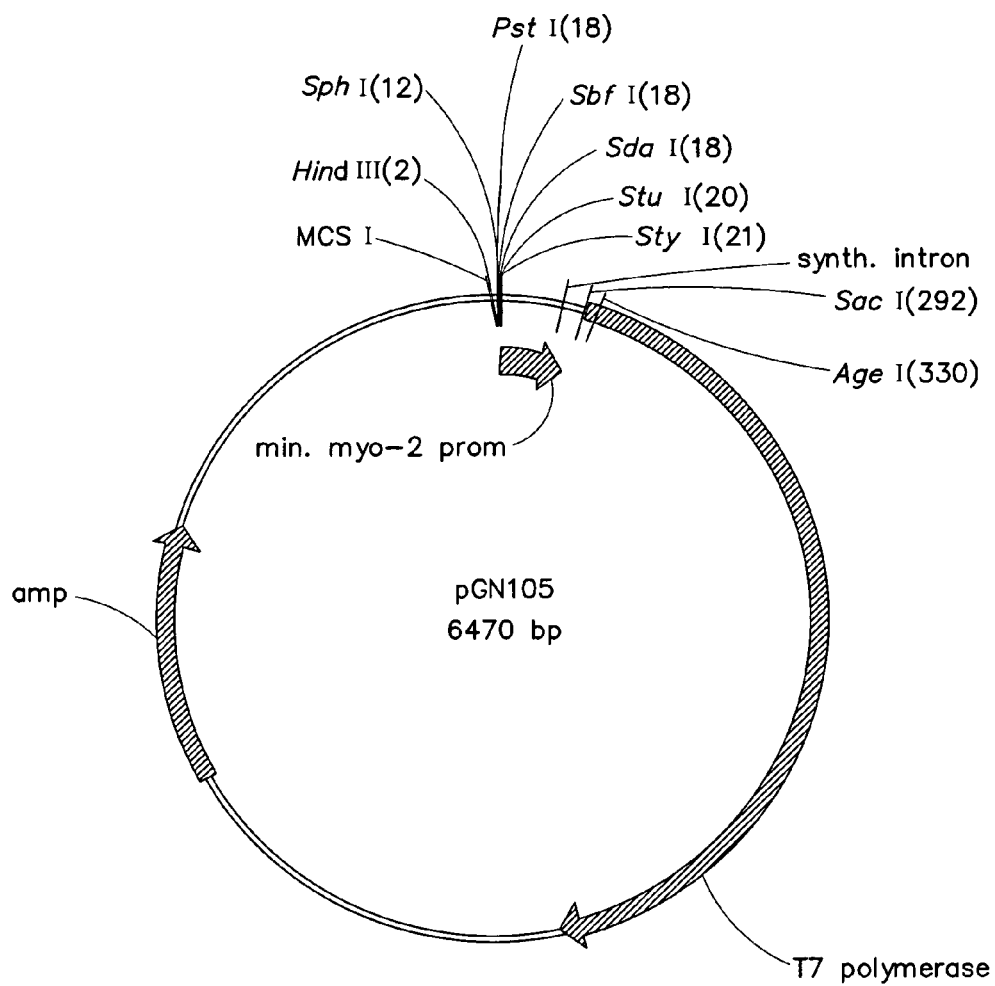
FIG. 11 is a representation of plasmid pGN105.

The T7 polymerase coding sequence was PCT amplified from λ CE6 (Novagen, Madison, USA) using the primers oGN26 (ATGGAATTCTTACGCGAACGCGAAGTCCG; SEQ ID NO:17) and oGN46 (CTCACCGGTAATGAACACGATTAACATCGC; SEQ ID NO:18), using standard procedures (PCT, A practical approach, 1993, Ed. J. McPherson, et al, IRL Press). The resulting DNA fragment encoding for the T7 RNA polymerase was digested with AgeI and EcoRI and inserted into the Fire vector pPD97.82 digested with AgeI and EcoRI. The resulting construct encodes for an open reading frame of T7 RNA polymerase in fusion with the SV40 large T antigen nuclear localization signal (NLS) with amino acid sequence MTAPKKKRKVPV (SEQ ID NO:19). This nuclear localization signal sequence is required to translocate the T7 RNA polymerase from the cytoplasm to the nucleus, where it is able to bind to its specific promoters, designated T7 promoters. Upstream of the coding sequence for the T7polymerasefusion protein is a minimal promoter (myo-2) preceded by a multiple cloning site (MCS) in which several *C. elegans* promoters can be inserted. This plasmid (pGN105 shown in FIG. 11) is a basic T7 RNA polymerase plasmid which enables the expression of T7polymerase in *C. elegans*. Derivatives of this plasmid wherein promoters are cloned into the multiple cloning site, allow for the inducible, constitutive, general and tissue specific expression of T7 RNA polymerase in *C. elegans*, as expression will be regulated by the promoter cloned in the multiple cloning site.

Although not restricted to these examples, for the following promoters it is known that they induce expression in the following tissues.

let-858 (ubiquitous expression), myo-2 (pharynx expression), myo-3 (body wall muscles), egl-15 (vulval muscles), unc-119 (pan-neuron).

Example 2

Construction of a Vector for Expression of T7 RNA Polymerase in C. elegans Muscle Tissue.

Figure 10:
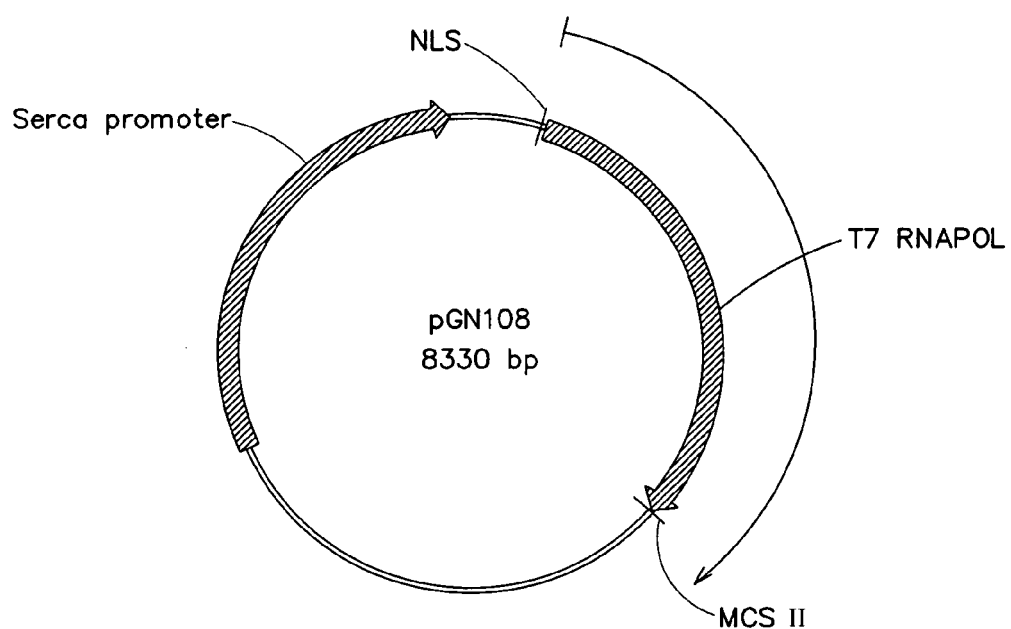
FIG. 10 is a representation of plasmid pGN108.

The T7 RNA polymerase coding sequence was PCR amplified from λ CE6 using the primers oGN43 (GCCAC-CGGTGCGAGCTCATGAACACGATTAACATCGC; SEQ ID NO:20) and oGN44 (CACTAGTGGGCCCTTACGC-GAACGCGAAGTCCG; SEQ ID NO:21) digested with AgeI/SpeI and inserted in the pGK13 vector digested with AgeI/SpeI. (This vector contains the strong SERCA promoter which drives expression in the pharynx, the vulval muscle, the tail and the body wall muscle). A nuclear localization signal (NLS) of SV40 large T antigen was inserted in front of the T7 polymerase coding sequence by insertion of two overlapping oligo's oGN45 (CCGGAT-GACTGCTCCAAAGAAGAAGCGTAAGCT; SEQ ID NO:22) and oGN46 (CTCACCGGTAATGAACACGAT-TAACATCGC; SEQ ID NO:19) into the SacI/AgeI restriction sites. The resulting construct was called pGN108 as shown in FIG. 10. Introduction of this plasmid into C. elegans results in the expression of T7 RNA polymerase in the pharynx, vulva muscle, tail and body wall muscles.

Figure 13:
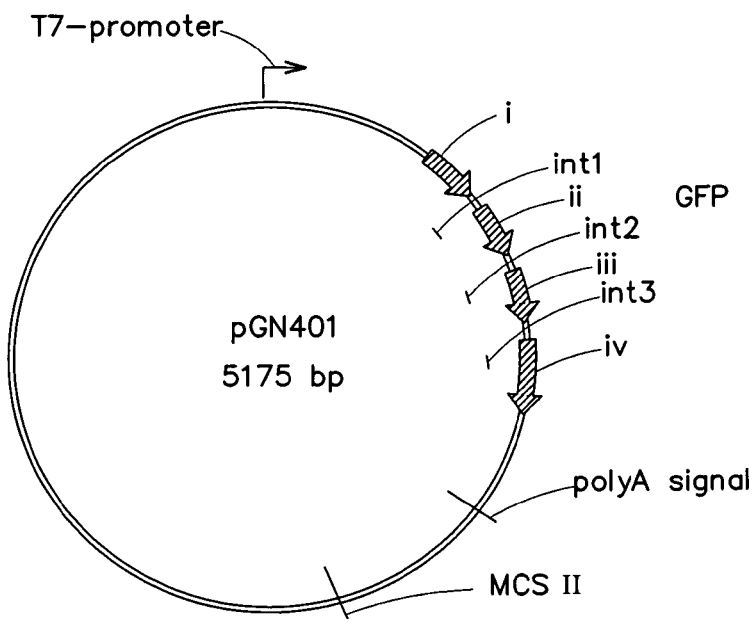
FIG. 13 is a representation of plasmid pGN401.

To test expression and functionality of T7 RNA polymerase in C. elegans under the regulation of the SERCA promoter, pGN108, which encodes the T7RNA polymerase under the control of the SERCA promoter was injected into C. elegans. A test vector was coinjected. This test vector encodes for GFP under the control of a T7 promoter (pGN401 in FIG. 13). The plasmid pGN401 was constructed by inserting two overlapping oligo's oGN41 (CCCGGGAT-TAATACGACTCACTATA; SEQ ID NO:23) and oGN42 (CCGGTATAGTGAGTCGTATTAATCCCGGGAGCT; SEQ ID NO:24) in the SacI/AgeI opened Fire vector pPD97.82. generating a T7 promoter. Furthermore a selection marker was coinjected to select for transformants (rol6, pRF4). The latter selection vector pRF4 is well known to person skilled in the art. Transgenic F1 could easy be isolated as they display the rol 6 phenotype. These transgenic C. elegans all expressed GFP in the pharynx, the vulval muscle, the tail and the body wall muscle. This data show clearly that the T7 RNA polymerase is functionally expressed under the regulation of the SERCA promoter, and that the expressed T7 RNA polymerase binds to the T7 promoter present in pGN401 and initiates transcription of the GFP gene, which is then functionally expressed, resulting in fluorescence in the muscle tissues where SERCA is inducing the expression of the T7 RNA polymerase.

Example 3

Figure 14:
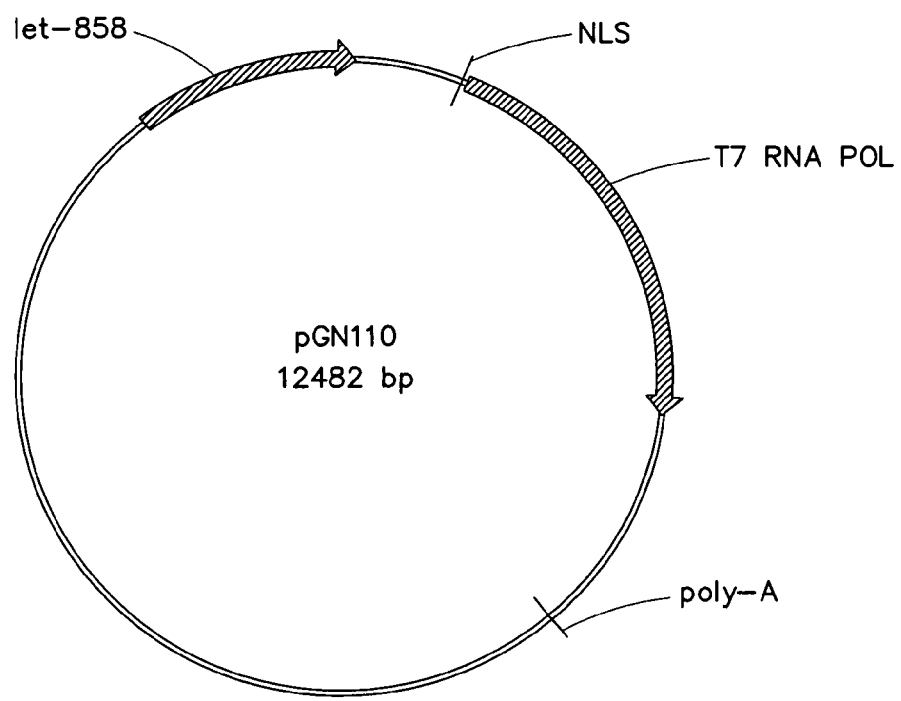
FIG. 14 is a representation of plasmid pGN110.
Figure 15:
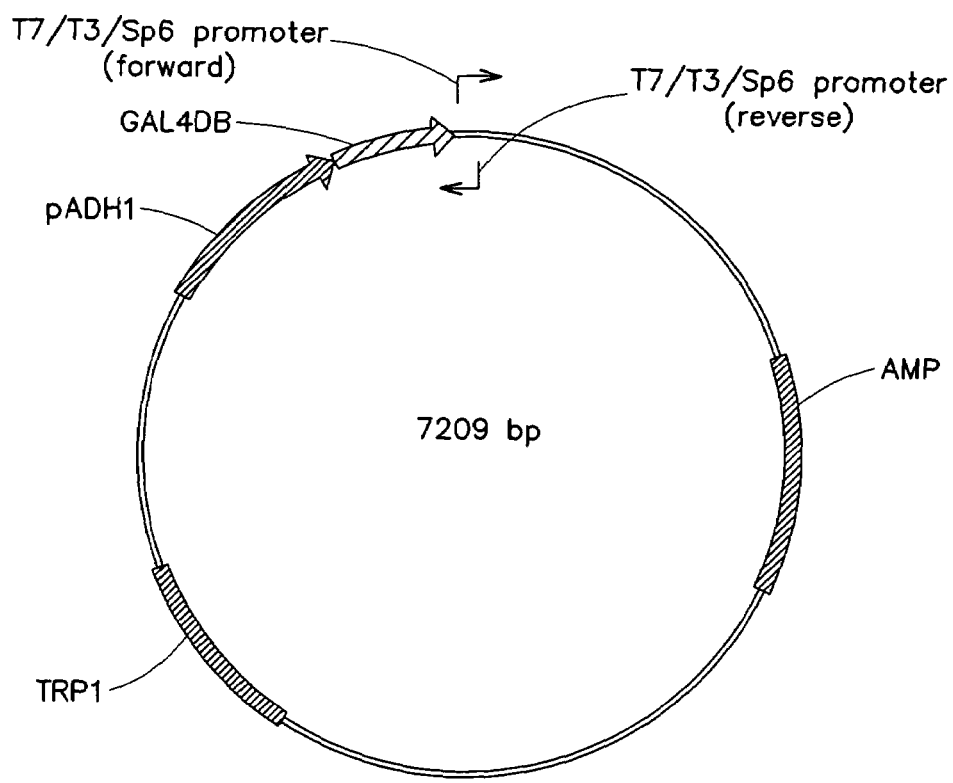
FIG. 15 is a representation of plasmid pAS2 with forward and reverse T7/T3/SP6 promoters.

Construction of a Vector for Ubiquitous Expression of T7 Polymerase in C. elegans The NLS-T7 RNA polymerase fusion gene was isolated from pGN108 with XmaI/Bsp1201 and cloned into the Fire vector pPD103.05 digested with XmaI/Bsp120I. This results in a vector wherein the T7 RNA polymerase is cloned under the regulation of the let858 promoter. This specific promoter enables the expression of T7 RNA polymerase in all tissues. The resulting plasmid was named pGN110 (FIG. 14).

Example 4

Figure 12:
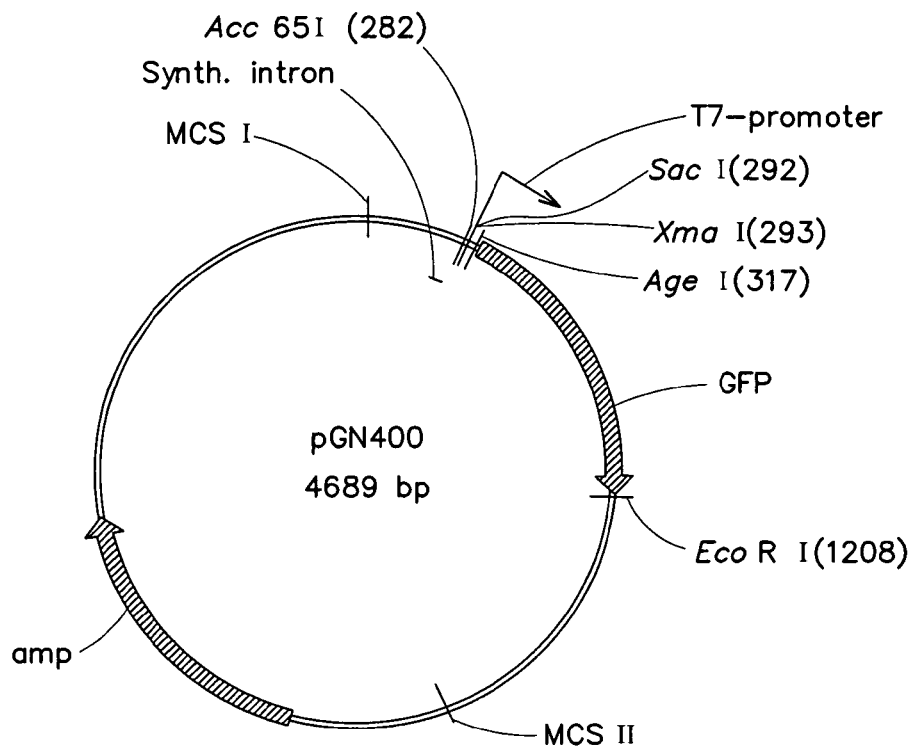
FIG. 12 is a representation of plasmid pGN400.

Construction of a Vector for T7 RNA Polymerase Mediated Expression of DNA Fragments, Genes, and cDNA's Under the Control of a T7 Promoter The Fire vector pPD97.82 was digested with SacI/AgeI and a T7 promoter sequence was generated by insertion of two overlapping oligo's oGN41 (CCCGGGATTAATAC-GACTCACTATA; SEQ ID NO:23) and oGN42 (CCGG-TATAGTGAGTCGTATTAATCCCGGGAGCT; SEQ ID NO:24) into the SacI/Age/restriction endonuclease sites. This construct (pGN400 FIG. 12) contains a GFP open reading frame cloned between SacI and EcoRI restriction endonuclease sites under the regulation of the T7 promoter. Any gene, cDNA, or DNA fragment can be cloned in this vector by deleting the GFP gene as a AgeI/SacI fragment and cloning the DNA fragment of interest into the vector. Preferentially the DNA fragment of interest can be obtained by PCR amplification, inserting the SacI/AfeI sites in the primers. The resulting DNA fragment after PCR amplification is the digested and the GFP gene in pGN400 is replaced by the amplified DNA fragment. Every vector that contains a T7 promoter could be used for the purpose of T7 RNA polymerase induced expression in C. elegans, such as the commercially available pGEM vectors and the pBluescript vectors. This is clearly shown by the pGN401 vector which expresses GFP under the regulation of the T7 promoter in a transgenic C. elegans which expresses T7 RNA polymerase.

The use of pGN400 has the advantage that the vector includes a 3"UTR fragment from unc-54 which enhances the transcription or stability of the RNA.

Generation of Permanent, Tissue Specific "Pseudo Knock-Out" RNAi C. elegans Lines At present, gene knock outs in C. elegans are obtained after random, large scale mutagenesis and PCR base sibselection. This method is bulky, very time consuming and tedious. It has been described that introducing double stranded RNA into a cell results in potent and specific interference of expression of endogenous genes. In C. elegans gene expression can be down regulated by injection of RNA into the body cavity of the worm, soaking the worm in a solution containing dsRNA or feeding E. coli that express dsRNA corresponding to the gene of interest. C. elegans cells have the ability to take in dsRNA from their extracellular environment. It has been reported that mRNA is the target of this ds RNA mediated genetic interference (Montgomery and Fire 1998). It is also suggested that the targeted RNA is degraded in the nucleus before translation can occur. Although the RNAi mediated reduction of gene expression can be passed on to the next generations, heritability is poor and the effect is rapidly lost during further offspring. This is probably due to a continued decrease of the dsRNA pool. We propose here a method to construct C. elegans lines with a permanent, inheritable, RNAi phenotype. The method encompasses the generation of transgenic C. elegans lines by introducing plasmids containing cDNA fragments of the target gene in the sense and antisense orientation under control of a worm promoter or by transcription of an inverted repeat of the cDNA from a single construct. Alternatively, ds RNA can be transcribed from a vector harboring a cDNA flanked by two T7 promoters in a C. elegans strain that expresses T7 polymerase. The result is a transgenic worm with an heritable stable "pseudo knockout" phenotype. The expression of the cDNA or the T7 polymerase can be general and constitutive but could also be regulated under a tissue specific promoter. In contrast to RNAi induced by external ds RNAi (injected, soaked or feeded) this method would enable to obtain conditional, tissue specific inhibition of gene expression.

Inhibition of Unc-22 Expression by RNA Interference Results in a "Twitching" Phenotype.

Figure 19A:
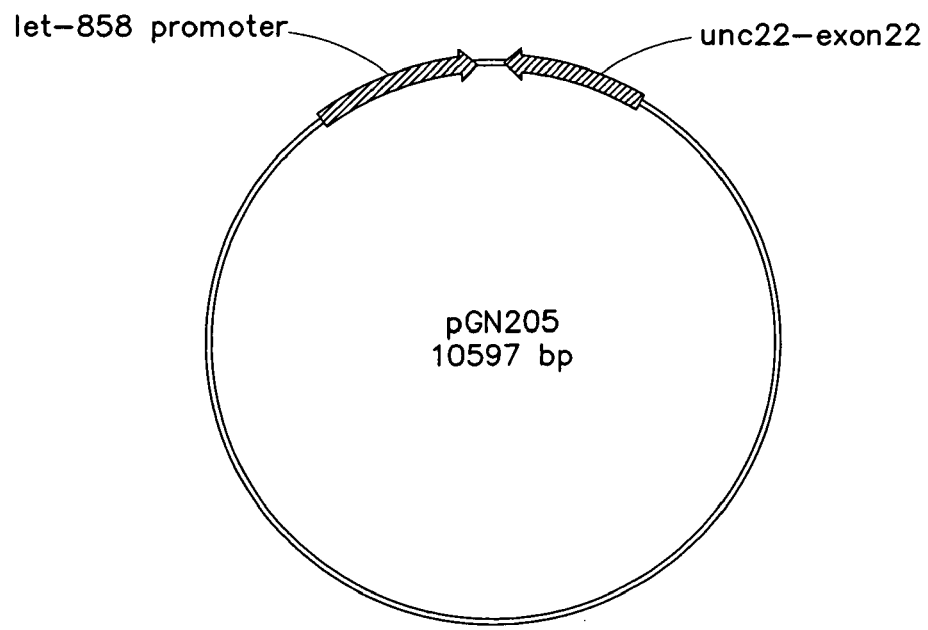
FIG. 19 (*a*) is a representation of plasmid pGN205 and (b) is a representation of plasmid pGN207.
Figure 19B:
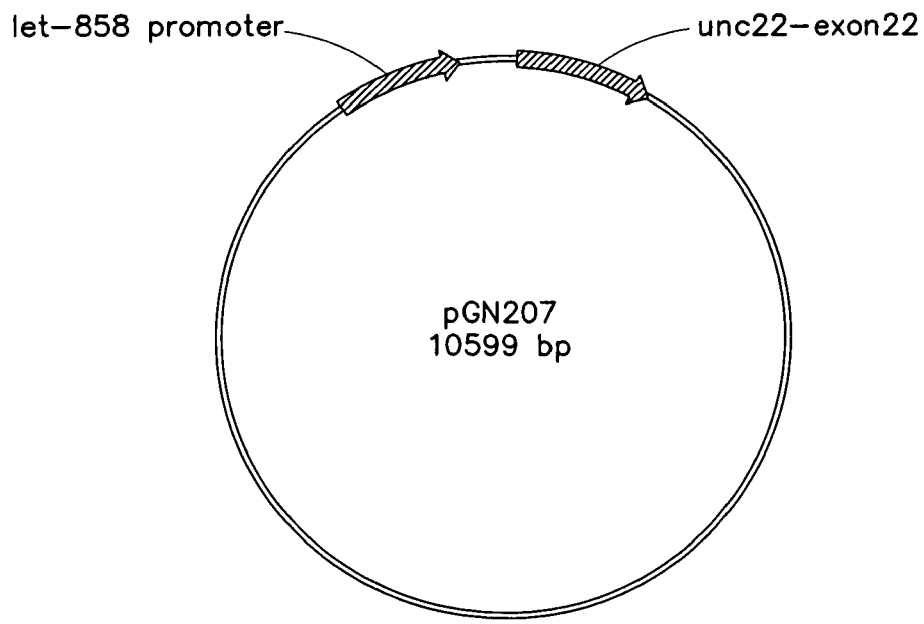

Unc 22 cDNA (exon 22) was cloned in sense and anti-sense orientation in pPD103.05. (A. Fire nr L2865) containing the let 858 promoter that is capable of expressing RNA sequences in all tissues. The resulting plasmids were named pGN205 (FIG. 19a) and pGN207 (FIG. 19 b). These constructs were introduced into C. elegans together with a selectable marker (rol-6; GFP). Transgenic F1 individuals (expressing rol-6 or GFP) showed a "twitching" phenotype indicating that RNAi could be mediated by endogenous transcription of RNA from transgenic DNA. The RNAi phenotype co-segregated with the selectable marker into further offspring. This resulted in the generation of C. elegans lines with permanent RNAi phenotype.

Generation of Stable Lines T7 RNA Polymerase Lines and Generation of Dual Transgenic Worms.

An expression system in C. elegans based on an exogenous RNA polymerase demands two plasmids. One is encoded for the RNA polymerase under the control of a specific promoter, while the other plasmid encodes for the DNA fragment to be expressed, under the regulation of the T7 promoter. In the case of semi stable RNAi also designated pseudo stable knockouts, the DNA of interest is cloned between two T7 promoters so that dsRNA can be produced.

As the T7 RNA polymerase expression system is known to be a high expression system this will result in problems to generate dually transgenic animals. If the gene to be expressed in the C. elegans nematode is toxic, this will result in lethal effects and hence in the construction of a C. elegans without highly regulated stable expression of the gene of interest. If the gene of interest is essential for the survival of the organism, RNAi with a DNA fragment from this gene will also result in lethal effects, so that pseudo-stable knockouts are not possible.

To overcome this problem the present inventors have designed a system consisting of two transgenic animals. The first animal is transgenic for the T7 RNA polymerase, This T7 RNA polymerase can be expressed in all cells or specific cells or tissues as has been shown in previous examples. The second transgenic animal is transgenic for the DNA fragment of interest. This can be a gene or cDNA linked to a T7 promoter, or if one wants to perform RNAi a DNA fragment of such gene cloned between two T7 promoters.

Both transgenic animals are viable and do not show any aberrant phenotypes. This is because the T7RNA polymerase expressed in the first transgenic organism is not toxic for the organism, even if expressed at relative high levels. In the second transgenic organism, the gene of interest is not expressed or the dsRNA is not produced as these transgenic animals do not contain the T7 RNA polymerase.

Expression of the gene or cDNA of interest or RNAi with a DNA fragment can now be obtained by mating the two transgenic animals. The offspring of these are dually transgenic and express the gene of interest or express dsRNa of the DNA fragment of interest. To generate sufficient males in such a mating, one of the transgenic animals males can be a C. elegans mutant with a phenotype favouring generation of males. An Example of such a mutant is him-S. Preferentially such a mutant will be used to make a C. elegans transgenic for T7 RNA polymerase, while the hermaphrodite harbors the DNA fragment under the regulation of the T7 promoter.

To select efficiently for the dual transgenic offspring a second transgene can be introduced in the second transgenic animal. This transgene contains a reporter gene under the regulation of the T7 promoter. The reporter gene can be GFP, luciferase, Beta galmactosidase, or beta-lactamase. an example of such a ttransgene are the vectors pGN400 and pGN401.

To obtain inducible, tissue specific expression of a transgene in C. elegans we can make male stock (i.e. him-5) carrying the T7 polymerase construct under the control of different C. elegans promoters that enable tissue specific expression such as). This males can be crossed with hermaphrodites carrying the gene of interest under the control of a T7 promoter.

Furthermore, the transgenes can be integrated into the genome of the animal. Methods to generate stable integration of a plasmid into the genome of the animal have been described (Methods in cell biology, Vol. 48, 1995, ed. by epstein and Shakes, academic press) and involve radiation of the animal. This can be done for both animals animals, but preferentially, the animals expressing the T7 RNA polymerase are subject to such traetment. This result in a collection of C. elegans nematodes that stably express T7 RNA polymerase under the control of various promoters. examples of such promoters are the myo-2 (pharynx expression), myo-3 (body wall muscles), egl-15 (vulval muscles), unc-119 (pan-neuron), SERCA (muscles), let858 (all cells) ges-1 (gut).

Construction of RNAi T7 Promoter Yeast Two Hybrid Vectors pGAD424 with Forward and Reverse T7/T3 and or Sp6

Figure 16:
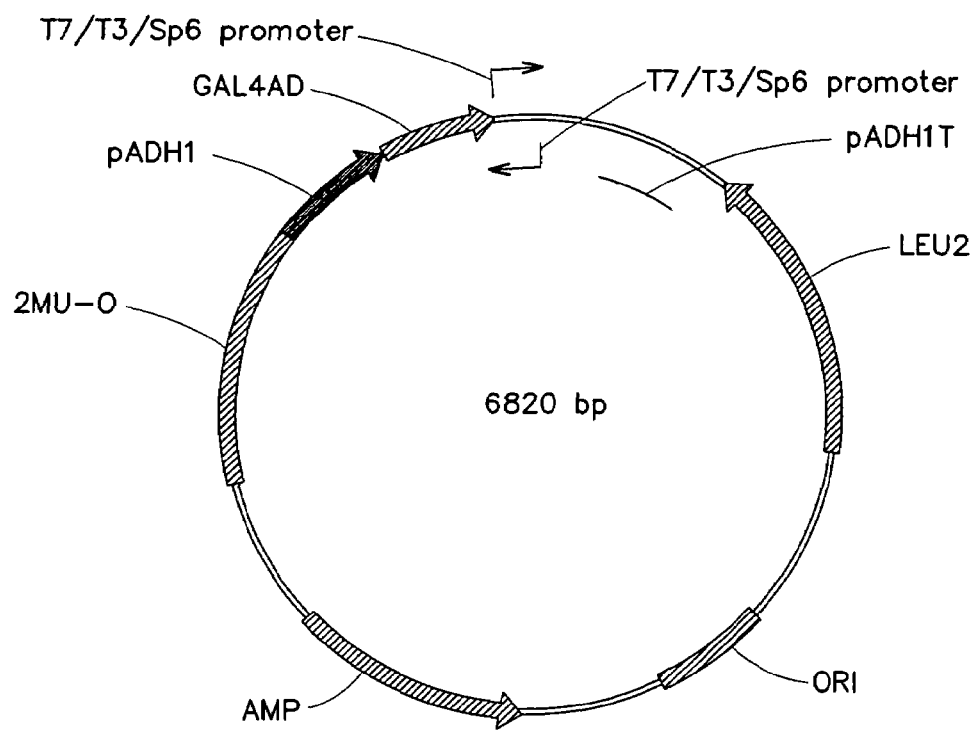
FIG. 16 is a representation of plasmid pGAD424 with forward and reverse T7/T3/SP6 promoters.
Figure 17:
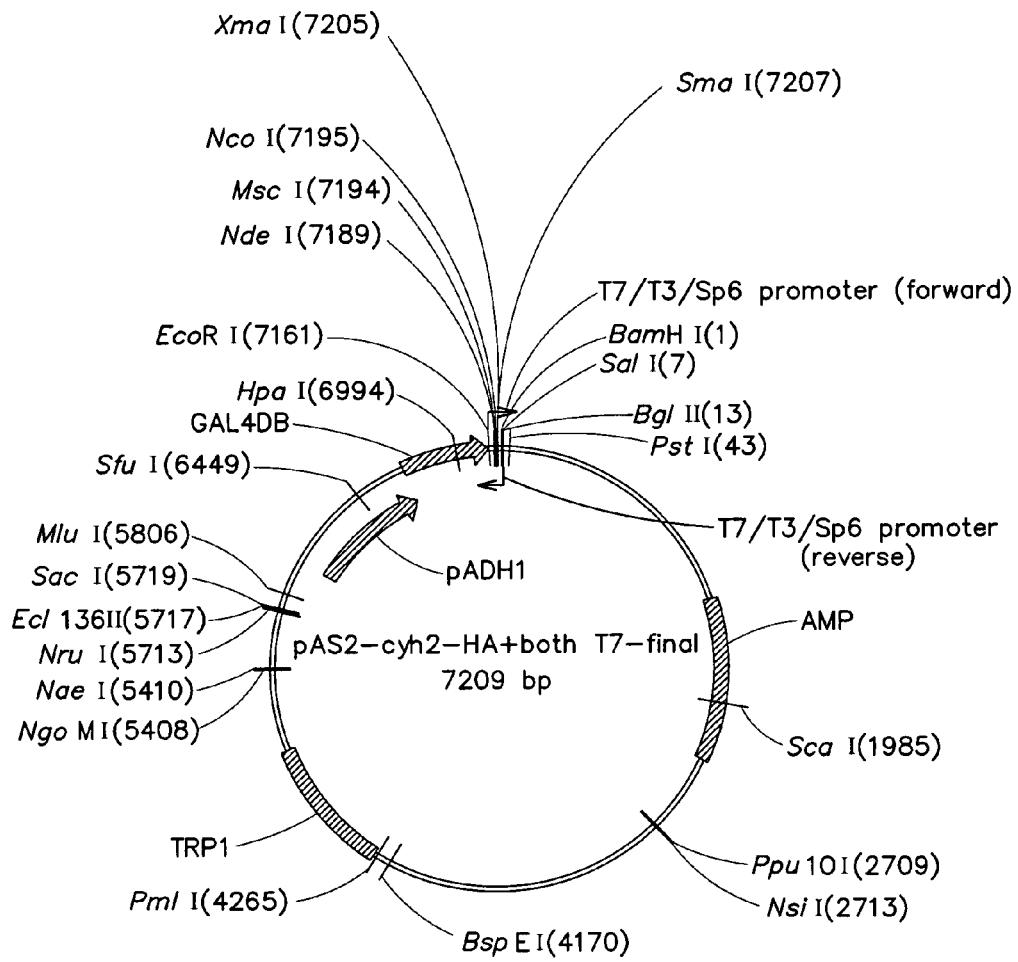
FIG. 17 is a representation of plasmid pAS2-cyh2-HA+, both T7-final.
Figure 18:
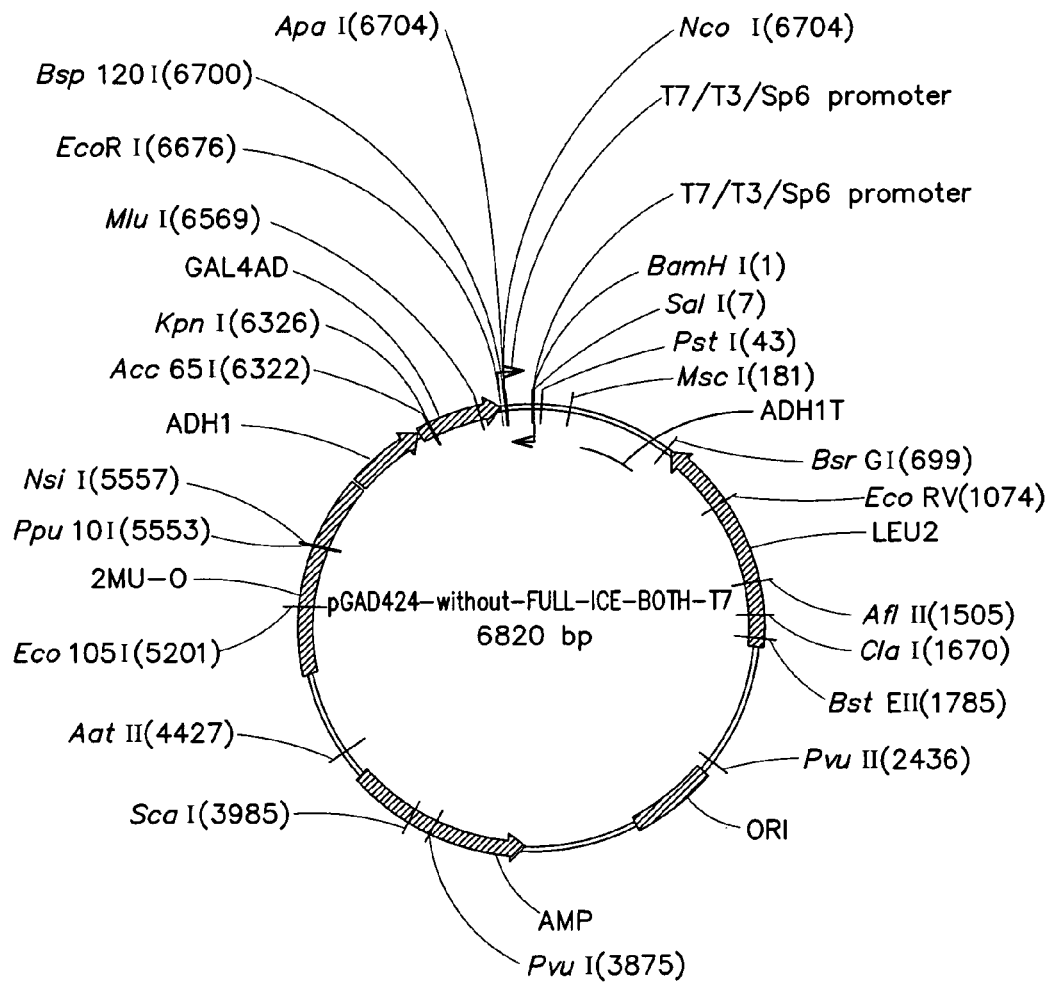
FIG. 18 is a representation of plasmid pGAD424-without-FULL-ICE-BOTH-T7.

In most two-hybrid experiments a cDNA library is cloned in plasmid pGAD424 (FIG. 16) which has been engineered with additional restriction sites in the polylinder such as a Ncol site (Clontech). This library allows for screening of binding proteins in a yeast two hybrid experiment. We constructed a new yeast two hybrid vector with the same possibilities to perform yeast two hybrid, but which contain two additional T7 promoters, so that the vector can be used for T7 RNA polymerase induced pseudo-stable knock-outs. For this we inserted a forward T7 by using a T7 linker (consisting of the following primers aattcttaatacgactcactat-agggcc (SEQ ID NO:25) and catgggccctatagtgagtcgtattaag (SEQ ID NO:26)) into the EcoRI-Ncol site of pGAD424. The resulting vector was designated pGAD424-without-FULL-ICE-both-T7. Care was taken to eliminate stop codons and using maximal polylinker compatible amino acids. We adopted the same strategy for the reverse T7 (consisting of both primers atccgtcgacagatctccctatagt-gagtcgtattactgca (SEQ ID NO:27) and gtaatacgactcactatagg-gagatctgtcgacg (SEQ ID NO:28)) with BamH1 and Pst1. To avoid loss of SalI, we included this site in the primer.

The SalI site is important as most libraries are cloned in this site, adapters are available. This makes the newly constructed vector compatible with existing vectors.

pAS2 with with Forward and Reverse T7/T3 and or Sp6

An analogous yeast two hybrid vector was constructed based on pAS2 (Clontech). By partial EcoRV digestion we were able to remove a significant part of the cyh2 gene. The right construct can be isolated and checked by a restriction digest with BglII. this restriction site is present in the EcoRV fragment of PAS2 to be eliminated. This elimates the cyh2 gene which is slightly toxic gene and involved in growth retardation. This gene is non-essential for the performing of RNAi and Yeast two hybrid experiments. After the elimination of the EcoRV fragment, The EcoRI restriction site which is located between the DNA sequence encoding for GAL4DB and HA (epitope) becomes unique for the plasmid, and can be used to subsitute HA with a T7 promoter containing linker. This ensures persistence of all restriction sites, allowing both in frame cloning and compatibility with previous vectors and pGAD424. We used the following linker (primers: aattcttaatacgactcactatagggca (SEQ ID NO:25) and tatgccctatagtgagtcgtattaag (SEQ ID NO:29)) using EcorI and Ndel cloning sites. we adopted the same strategy for the reverse T7 (primers: gatccgtcgacagatctc-cctatagtgagtcgtattactgca (SEQ ID NO:27) catgggccctatagt-gagtcgtattaag (SEQ ID NO:26) and gtaatacgactcactatagg-gagatctgtcgacg (SEQ ID NO:28)) with BamH1 and Pst1. To avoid loss of SalI we included it in the primer. The resulting vector was designated pAS2-cyh2HA+both T7-final.

Having the T7 promoter (or alternatively the T3, or SP6 promoter) in pGAD424 allows to go quickly from interacting protein to RNAi and assigning function to the isolated DNA fragment. An additional advantage is the ability to make by in vitro transcription coupled to in vitro translation (There is an ATG in frame with either GAL4 DB or GAL4AD) labeled protein which can be used for in vitro controls (e.g. pull down assays) of the actual protein—protein interaction.

The sequences of the plasmids produced and the SP6 and T3 polymerase are identified in the Sequence Listing provided below:

SEQUENCE LISTING

```
<160> NUMBER OF SEQ ID NOS: 29

<210> SEQ ID NO 1
<211> LENGTH: 3216
<212> TYPE: DNA
<213> ORGANISM: Artificial Sequence
<220> FEATURE:
<223> OTHER INFORMATION: Description of Artificial Sequence:plasmid DNA

<400> SEQUENCE: 1
gagtgcacca tatgcggtgt gaaataccgc acagatgcgt aaggagaaaa taccgcatca      60
ggcgaaattg taaacgttaa tattttgtta aaattcgcgt taaatatttg ttaaatcagc     120 tcattttta  accaataggc cgaaatcggc aaaatcccttt ataaatcaaa agaatagacc     180 gagataggt  tgagtgttgt tccagtttgg aacaagagtc cactattaaa gaacgtggac     240
tccaacgtca aagggcgaaa aaccgtctat cagggcgatg gcccactacg tgaaccatca     300
cccaaatcaa gttttttgcg gtcgaggtgc cgtaaagctc taaatcggaa ccctaaaggg     360
agcccccgat ttagagcttg acggggaaag ccggcgaacg tggcgagaaa ggaagggaag     420
aaagcgaaag gagcgggcgc tagggcgctg gcaagtgtag cggtcacgct gcgcgtaacc     480
accacacccg ccgcgcttaa tgcgccgcta cagggcgcgt ccattcgcca ttcaggctgc     540
gcaactgttg ggaagggcga tcggtgcggg cctcttcgct attacgccag ctggcgaaag     600
ggggatgtgc tgcaaggcga ttaagttggg taacgccagg gttttcccag tcacgacgtt     660
gtaaaacgac ggccagtgaa ttgtaatacg actcactata gggcgaattc gagctcggta     720
cccggggatc ctctagagtc gaaagcttct cgccctatag tgagtcgtat tacagcttga     780
gtattctata gtgtcaccta aatagcttgg cgtaatcatg gtcatagctg tttcctgtgt     840
gaaattgtta tccgctcaca attccacaca acatacgagc cggaagcata aagtgtaaag     900
cctggggtgc ctaatgagtg agctaactca cattaattgc gttgcgctca ctgcccgctt     960
tccagtcggg aaacctgtcg tgccagctgc attaatgaat cggccaacgc gcggggagag    1020
gcggtttgcg tattgggcgc tcttccgctt cctcgctcac tgactcgctg cgctcggtcg    1080
ttcggctgcg gcgagcggta tcagctcact caaaggcggt aatacggtta tccacagaat    1140
caggggataa cgcaggaaag aacatgtgag caaaaggcca gcaaaaggcc aggaaccgta    1200
aaaaggccgc gttgctggcg ttttttcgata ggctccgccc ccctgacgag catcacaaaa    1260
atcgacgctc aagtcagagg tggcgaaacc cgacaggact ataaagatac caggcgtttc    1320
cccctggaag ctccctcgtg cgctctcctg ttccgaccct gccgcttacc ggatacctgt    1380
```

-continued

```
ccgcctttct cccttcggga agcgtggcgc tttctcatag ctcacgctgt aggtatctca   1440
gttcggtgta ggtcgttcgc tccaagctgg gctgtgtgca cgaaccccc gttcagcccg    1500 accgctgcgc cttatccggt aactatcgtc ttgagtccaa cccggtaaga cacgacttat   1560
cgccactggc agcagccact ggtaacagga ttagcagagc gaggtatgta ggcggtgcta   1620
cagagttctt gaagtggtgg cctaactacg gctacactag aaggacagta tttggtatct   1680
gcgctctgct gaagccagtt accttcggaa aaagagttgg tagctcttga tccggcaaac   1740
aaaccaccgc tggtagcggt ggtttttttg tttgcaagca gcagattacg cgcagaaaaa   1800
aaggatctca agaagatcct ttgatctttt ctacggggtc tgacgctcag tggaacgaaa   1860
actcacgtta agggattttg gtcatgagat tatcaaaaag gatcttcacc tagatccttt   1920
taaattaaaa atgaagtttt aaatcaatct aaagtatata tgagtaaact ggtctgaca    1980 gttaccaatg cttaatcagt gaggcaccta tctcagcgat ctgtctattt cgttcatcca   2040
tagttgcctg actccccgtc gtgtagataa ctacgatacg ggagggctta ccatctggcc   2100
ccagtgctgc aatgataccg cgagacccac gctcaccggc tccagattta tcagcaataa   2160
accagccagc cggaagggcc gagcgcagaa gtggtcctgc aactttatcc gcctccatcc   2220
agtctattaa ttgttgccgg gaagctagag taagtagttc gccagttaat agtttgcgca   2280
acgttgttgg cattgctaca ggcatcgtgg tgtcacgctc gtcgtttggt atggcttcat   2340
tcagctccgg ttcccaacga tcaaggcgag ttacatgatc ccccatgttg tgcaaaaaag   2400
cggttagctc cttcggtcct ccgatcgttg tcagaagtaa gttggccgca gtgttatcac   2460
tcatggttat ggcagcactg cataattctc ttactgtcat gccatccgta agatgctttt   2520
ctgtgactgg tgagtactca accaagtcat tctgagaata gtgcgcccgg cgaccgagtt   2580
gctcttgccc ggcgtcaata cgggataata gtgtatgaca tagcagaact ttaaaagtgc   2640
tcatcattgg aaaacgttct cgggggcgaa aactctcaag gatcttaccg ctgttgagat   2700
ccagttcgat gtaacccact cgtgcaccca actgatcttc agcatctttt actttcacca   2760
gcgtttctgg gtgagcaaaa acaggaaggc aaaatgccgc aaaaaaggga ataagggcga   2820
cacggaaatg ttgaatactc atactcttcc tttttcaata ttattgaagc atttatcagg   2880
gttattgtct catgagcgga tacatatttg aatgtattta gaaaaataaa caaataggg    2940 ttccgcgcac atttccccga aaagtgccac ctgacgtcta agaaaccatt attatcatga   3000
cattaaccta taaaaatagg cgtatcacga ggccctttcg tctcgcgcgt ttcggtgatg   3060
acggtgaaaa cctctgacac atgcagctcc cggagacggt cacagcttgt ctgtaagcgg   3120
atgccgggag cagacaagcc cgtcagggcg cgtcagcggg tgttggcggg tgtcggggct   3180
ggcttaacta tgcggcatca gagcagattg tactga                            3216
```

<210> SEQ ID NO 2
<211> LENGTH: 6460
<212> TYPE: DNA
<213> ORGANISM: Artificial Sequence
<220> FEATURE:
<223> OTHER INFORMATION: Description of Artificial Sequence:plasmid DNA

<400> SEQUENCE: 2

```
ctagcatgaa cacgattaac atcgctaaga acgacttctc tgacatcgaa ctggctgcta     60
tcccgttcaa cactctggct gaccattacg gtgagcgttt agctcgcgaa cagttggccc    120
ttgagcatga gtcttacgag atgggtgaag cacgcttccg caagatgttt gagcgtcaac    180
ttaaagctgg tgaggttgcg gataacgctg ccgccaagcc tctcatcact accctactcc    240
```

-continued

```
ctaagatgat tgcacgcatc aacgactggt ttgaggaagt gaaagctaag cgcggcaagc    300
gcccgacagc cttccagttc ctgcaagaaa tcaagccgga agccgtagcg tacatcacca    360
ttaagaccac tctggcttgc ctaaccagtg ctgacaatac aaccgttcag gctgtagcaa    420
gcgcaatcgg tcgggccatt gaggacgagg ctcgcttcgg tcgtatccgt gaccttgaag    480
ctaagcactt caagaaaaac gttgaggaac aactcaacaa gcgcgtaggg cacgtctaca    540
agaaagcatt tatgcaagtt gtcgaggctg acatgctctc taagggtcta ctcggtggcg    600
aggcgtggtc ttcgtggcat aaggaagact ctattcatgt aggagtacgc tgcatcgaga    660
tgctcattga gtcaaccgga atggttagct acaccgcca aaatgctggc gtagtaggtc    720
aagactctga gactatcgaa ctcgcacctg aatacgctga ggctatcgca acccgtgcag    780
gtgcgctggc tggcatctct ccgatgttcc aaccttgcgt agttcctcct aagccgtgga    840
ctggcattac tggtggtggc tattgggcta acggtcgtcg tcctctggcg ctggtgcgta    900
ctcacagtaa gaaagcactg atgcgctacg aagacgttta catgcctgag gtgtacaaag    960
cgattaacat tgcgcaaaac accgcatgga aaatcaacaa gaaagtccta gcggtcgcca   1020
acgtaatcac caagtggaag cattgtccgg tcgaggacat ccctgcgatt gagcgtgaag   1080
aactcccgat gaaaccggaa gacatcgaca tgaatcctga ggctctcacc gcgtggaaac   1140
gtgctgccgc tgctgtgtac cgcaaggaca gggctcgcaa gtctcgccgt atcagccttg   1200
agttcatgct tgagcaagcc aataagtttg ctaaccataa ggccatctgg ttcccttaca   1260
acatggactg gcgcggtcgt gtttacgccg tgtcaatgtt caacccgcaa ggtaacgata   1320
tgaccaaagg actgcttacg ctggcgaaag gtaaaccaat cggtaaggaa ggttactact   1380
ggctgaaaat ccacggtgca aactgtgcgg gtgtcgataa ggttccgttc cctgagcgca   1440
tcaagttcat tgaggaaaac cacgagaaca tcatggcttg cgctaagtct ccactggaga   1500
acacttggtg ggctgagcaa gattctccgt tctgcttcct tgcgttctgc tttgagtacg   1560
ctggggtaca gcaccacggc ctgagctata actgctccct tccgctggcg tttgacgggt   1620
cttgctctgg catccagcac ttctccgcga tgctccgaga tgaggtaggt ggtcgcgcgg   1680
ttaacttgct tcctagtgag accgttcagg acatctacgg gattgttgct aagaaagtca   1740
acgagattct acaagcagac gcaatcaatg ggaccgataa cgaagtagtt accgtgaccg   1800
atgagaacac tggtgaaatc tctgagaaag tcaagctggg cactaaggca ctggctggtc   1860
aatggctggc tcacggtgtt actcgcagtg tgactaagcg ttcagtcatg acgctggctt   1920
acgggtccaa agagttcggc ttccgtcaac aagtgctgga agataccatt cagccagcta   1980
ttgattccgg caagggtccg atgttcactc agccgaatca ggctgctgga tacatggcta   2040
agctgatttg ggaatctgtg agcgtgacgg tggtagctgc ggttgaagca atgaactggc   2100
ttaagtctgc tgctaagctg ctggctgctg aggtcaaaga taagaagact ggagagattc   2160
ttcgcaagcg ttgcgctgtg cattgggtaa ctcctgatgg ttttccctgtg tggcaggaat   2220
acaagaagcc tattcagacg cgcttgaacc tgatgttcct cggtcagttc cgcttacagc   2280
ctaccattaa caccaacaaa gatagcgaga ttgatgcaca caaacaggag tctggtatcg   2340
ctcctaactt tgtacacagc caagacggta gccaccttcg taagactgta gtgtgggcac   2400
acgagaagta cggaatcgaa tcttttgcac tgattcacga ctccttcggt accattccgg   2460
ctgacgctgc gaacctgttc aaagcagtgc gcgaaactat ggttgacaca tatgagtctt   2520
gtgatgtact ggctgatttc tacgaccagt tcgctgacca gttgcacgag tctcaattgg   2580
```

-continued

```
acaaaatgcc agcacttccg gctaaaggta acttgaacct ccgtgacatc ttagagtcgg    2640
acttcgcgtt cgcgtaacca tggtattgat atctgagctc cgcatcggcc gctgtcatca    2700
gatcgccatc tcgcgcccgt gcctctgact tctaagtcca attactcttc aacatcccta    2760
catgctcttt ctccctgtgc tcccaccccc tattttgtt attatcaaaa aaacttcttc     2820
ttaatttctt tgtttttag cttcttttaa gtcacctcta acaatgaaat tgtgtagatt     2880
caaaaataga attaattcgt aataaaaagt cgaaaaaaat tgtgctccct cccccattta    2940
ataataattc tatcccaaaa tctacacaat gttctgtgta cacttcttat gtttttttta    3000
cttctgataa attttttg aaacatcata gaaaaaccg cacacaaaat accttatcat       3060
atgttacgtt tcagtttatg accgcaattt ttatttcttc gcacgtctgg gcctctcatg    3120
acgtcaaatc atgctcatcg tgaaaaagtt ttggagtatt tttggaattt ttcaatcaag    3180
tgaaagttta tgaaattaat tttcctgctt ttgcttttg ggggtttccc ctattgtttg     3240
tcaagagttt cgaggacggc gttttttcttg ctaaaatcac aagtattgat gagcacgatg   3300
caagaaagat cggaagaagg tttgggtttg aggctcagtg gaaggtgagt agaagttgat    3360
aatttgaaag tggagtagtg tctatggggt ttttgcctta aatgacagaa tacattccca    3420
atataccaaa cataactgtt tcctactagt cggccgtacg ggccctttcg tctcgcgcgt    3480
ttcggtgatg acggtgaaaa cctctgacac atgcagctcc cggagacggt cacagcttgt    3540
ctgtaagcgg atgccgggag cagacaagcc cgtcagggcg cgtcagcggg tgttggcggg    3600
tgtcggggct ggcttaacta tgcggcatca gagcagattg tactgagagt gcaccatatg    3660
cggtgtgaaa taccgcacag atgcgtaagg agaaaatacc gcatcaggcg gccttaaggg    3720
cctcgtgata cgcctatttt tataggttaa tgtcatgata ataatggttt cttagacgtc    3780
aggtggcact tttcggggaa atgtgcgcgg aacccctatt tgtttatttt tctaaataca    3840
ttcaaatatg tatccgctca tgagacaata accctgataa atgcttcaat aatattgaaa    3900
aaggaagagt atgagtattc aacatttccg tgtcgccctt attcccttt ttgcggcatt     3960 ttgccttcct gttttgctc acccagaaac gctggtgaaa gtaaaagatg ctgaagatca    4020
gttgggtgca cgagtgggtt acatcgaact ggatctcaac agcggtaaga tccttgagag    4080
ttttcgcccc gaagaacgtt ttccaatgat gagcactttt aaagttctgc tatgtggcgc    4140
ggtattatcc cgtattgacg ccgggcaaga gcaactcggt cgccgcatac actattctca    4200
gaatgacttg gttgagtact caccagtcac agaaaagcat cttacggatg gcatgacagt    4260
aagagaatta tgcagtgctg ccataaccat gagtgataac actgcggcca acttacttct    4320
gacaacgatc ggaggaccga aggagctaac cgcttttttg cacaacatgg ggatcatgt     4380 aactcgcctt gatcgttggg aaccggagct gaatgaagcc ataccaaacg acgagcgtga    4440
caccacgatg cctgtagcaa tggcaacaac gttgcgcaaa ctattaactg gcgaactact    4500
tactctagct tcccggcaac aattaataga ctggatggag gcggataaag ttgcaggacc    4560
acttctgcgc tcggcccttc cggctggctg gtttattgct gataaatctg gagccggtga    4620
gcgtgggtct cgcggtatca ttgcagcact ggggccagat ggtaagccct cccgtatcgt    4680
agttatctac acgacgggga gtcaggcaac tatggatgaa cgaaatagac agatcgctga    4740
gataggtgcc tcactgatta gcattggta actgtcagac caagtttact catatatact    4800
ttagattgat ttaaaacttc atttttaatt taaaaggatc taggtgaaga tccttttga    4860 taatctcatg accaaaatcc cttaacgtga gttttcgttc cactgagcgt cagacccgt     4920 agaaaagatc aaaggatctt cttgagatcc tttttttctg cgcgtaatct gctgcttgca    4980
```

-continued

```
aacaaaaaaa ccaccgctac cagcggtggt ttgtttgccg gatcaagagc taccaactct    5040
ttttccgaag gtaactggct tcagcagagc gcagatacca aatactgtcc ttctagtgta    5100
gccgtagtta ggccaccact tcaagaactc tgtagcaccg cctacatacc tcgctctgct    5160
aatcctgtta ccagtggctg ctgccagtgg cgataagtcg tgtcttaccg ggttggactc    5220
aagacgatag ttaccggata aggcgcagcg gtcgggctga acgggggggtt cgtgcacaca    5280 gcccagcttg gagcgaacga cctacaccga actgagatac ctacagcgtg agcattgaga    5340
aagcgccacg cttcccgaag ggagaaaggc ggacaggtat ccggtaagcg gcagggtcgg    5400
aacaggagag cgcacgaggg agcttccagg gggaaacgcc tggtatcttt atagtcctgt    5460
cgggtttcgc cacctctgac ttgagcgtcg attttttgtga tgctcgtcag ggggcggag    5520 cctatggaaa aacgccagca acgcggcctt tttacggttc ctggccttt  gctggccttt    5580 tgctcacatg ttctttcctg cgttatcccc tgattctgtg gataaccgta ttaccgcctt    5640
tgagtgagct gataccgctc gccgcagccg aacgaccgag cgcagcgagt cagtgagcga    5700
ggaagcggaa gagcgcccaa tacgcaaacc gcctctcccc gcgcgttggc cgattcatta    5760
atgcagctgg cacgacaggt ttcccgactg gaaagcgggc agtgagcgca acgcaattaa    5820
tgtgagttag ctcactcatt aggcacccca ggctttacac tttatgcttc cggctcgtat    5880
gttgtgtgga attgtgagcg gataacaatt tcacacagga aacagctatg accatgatta    5940
cgccaagctt gcatgcctgc aggtcgactc tagaggatca agagcatttg aatcagaata    6000
tggagaacgg agcatgagca ttttcgaagt tttttagatg cactagaaca aagcgtgttg    6060
gcttcctctg agcccgcttt ccttatatac ccgcattctg cagccttaca gaatgttcta    6120
gaaggtccta gatgcattcg tttgaaaata ctcccggtgg gtgcaaagag acgcagacgg    6180
aaaatgtatc tgggtctctt tattgtgtac actactttc  catgtaccga atgtgagtcg    6240
ccctcctttt gcaacaagca gctcgaatgt tctagaaaaa ggtggaaaat agtataaata    6300
ccgttgaaaa taaataccga acaacatttg ctctaattgt gaaattagaa atcttcaaac    6360
tataatcatc tcactggatc cccgggattg gccaaaggac ccaaaggtat gtttcgaatg    6420
atactaacat aacatagaac attttcagga ggacccttgg                         6460
```

<210> SEQ ID NO 3
<211> LENGTH: 8330
<212> TYPE: DNA
<213> ORGANISM: Artificial Sequence
<220> FEATURE:
<223> OTHER INFORMATION: Description of Artificial Sequence:plasmid DNA

<400> SEQUENCE: 3

```
gttgtcgtaa agagatgttt ttattttact ttacaccggg tcctctctct ctgccagcac      60
agctcagtgt tggctgtgtg ctcgggctcc tgccaccggc ggcctcatct tcttcttctt     120
cttctctcct gctctcgctt atcacttctt cattcattct tattcctttt catcatcaaa     180
ctagcatttc ttactttatt tatttttttc aattttcaat tttcagataa accaaaacta     240
cttgggttac agccgtcaac agatccccgg gattggccaa aggacccaaa ggtatgtttc     300
gaatgatact aacataacat agaacatttt caggaggacc cttgcttgga gggtaccgga     360
tgactgctcc aaagaagaag cgtaagctca tgaacacgat taacatcgct aagaacgact     420
tctctgacat cgaactggct gctatcccgt tcaacactct ggctgaccat tacggtgagc     480
gtttagctcg cgaacagttg gcccttgagc atgagtctta cgagatgggt gaagcacgct     540
```

```
tccgcaagat gtttgagcgt caacttaaag ctggtgaggt tgcggataac gctgccgcca    600
agcctctcat cactacccta ctccctaaga tgattgcacg catcaacgac tggtttgagg    660
aagtgaaagc taagcgcggc aagcgcccga cagccttcca gttcctgcaa gaaatcaagc    720
cggaagccgt agcgtacatc accattaaga ccactctggc ttgcctaacc agtgctgaca    780
atacaaccgt tcaggctgta gcaagcgcaa tcggtcgggc cattgaggac gaggctcgct    840
tcggtcgtat ccgtgacctt gaagctaagc acttcaagaa aaacgttgag gaacaactca    900
acaagcgcgt agggcacgtc tacaagaaag catttatgca agttgtcgag gctgacatgc    960
tctctaaggg tctactcggt ggcgaggcgt ggtcttcgtg gcataaggaa gactctattc   1020
atgtaggagt acgctgcatc gagatgctca ttgagtcaac cggaatggtt agcttacacc   1080
gccaaaatgc tggcgtagta ggtcaagact ctgagactat cgaactcgca cctgaatacg   1140
ctgaggctat cgcaacccgt gcaggtgcgc tggctggcat ctctccgatg ttccaacctt   1200
gcgtagttcc tcctaagccg tggactggca ttactggtgg tggctattgg gctaacggtc   1260
gtcgtcctct ggcgctggtg cgtactcaca gtaagaaagc actgatgcgc tacgaagacg   1320
tttacatgcc tgaggtgtac aaagcgatta acattgcgca aaacaccgca tggaaaatca   1380
acaagaaagt cctagcggtc gccaacgtaa tcaccaagtg gaagcattgt ccggtcgagg   1440
acatccctgc gattgagcgt gaagaactcc cgatgaaacc ggaagacatc gacatgaatc   1500
ctgaggctct caccgcgtgg aaacgtgctg ccgctgctgt gtaccgcaag acaaggctcg   1560
caagtctcgc cgtatcagcc ttgagttcat gcttgagcaa gccaataagt ttgctaacca   1620
taaggccatc tggttcccctt acaacatgga ctggcgcggt tcgtgtttac gctgtgtcaa   1680
tgttcaaccc gcaaggtaac gatatgacca aaggacgtct tacgctggcg aaaggtaaac   1740
caatcggtaa ggaaggttac tactggctga aaatccacgg tgcaaactgt gcgggtgtcg   1800
ataaggtttc gtttcctgag cgcatcaagt tcattgagga aaaccacgag aacatcatgg   1860
cttgcgctaa gtctccactg gagaacactt ggtgggctga gcaagattct ccgttctgct   1920
tccttgcgtt ctgctttgag tacgctgggg tacagcacca cggcctgagc tataactgct   1980
cccttccgct ggcgtttgac gggtcttgct ctggcatcca gcacttctcc gcgatgctcc   2040
gagatgaggt aggtggtcgc gcggttaact tgcttcctag tgaaaccgtt caggacatct   2100
acgggattgt tgctaagaaa gtcaacgaga ttctgcaagc agacgcaatc aatgggaccg   2160
ataacgaagt agttaccgtg accgatgaga acactggtga aatctctgag aaagtcaagc   2220
tgggcactaa ggcactggct ggtcaatggc tggcttacgg tgttactcgc agtgtgacta   2280
agcgttcagt catgacgctg gcttacgggt ccaaagagtt cggcttccgt caacaagtgc   2340
tggaagatac cattcagcca gctattgatt ccggcaaggg tctgatgttc actcagccga   2400
atcaggctgc tggatacatg gctaagctga tttgggaatc cgtgagcgtg acggtggtag   2460
ctgcggttga agcaatgaac tggcttaagt ctgctgctaa gctgctggct gctgaggtca   2520
aagataagaa gactggagag attcttcgca agcgttgcgc tgtgcattgg gtaactcctg   2580
atggtttccc tgtgtggcag gaatacaaga agcctattca gacgcgcttg aacctgatgt   2640
tcctcggtca gttccgctta cagcctacca ttaacaccaa caaagatagc gagattgatg   2700
cacacaaaca ggagtctggt atcgctccta actttgtaca cagccaagac ggtagccacc   2760
ttcgtaagac tgtagtgtgg gcacacgaga gtacggaat cgaatctttt gcactgattc   2820
acgactcctt cggtaccatt ccggctgacg ctgcgaacct gttcaaagca gtgcgcgaaa   2880
ctatggttga cacatatgag tcttgtgatg tactggctga tttctacgac cagttcgctg   2940
```

-continued

```
accagttgca cgagtctcaa ttggacaaaa tgccagcact tccggctaaa ggtaacttga    3000
acctccgtga catcttagag tcggacttcg cgttcgcgta agggcccact agtcggccgt    3060
acgggccctt tcgtctcgcg cgtttcggtg atgacggtga aaacctctga cacatgcagc    3120
tcccggagac ggtcacagct tgtctgtaag cggatgccgg gagcagacaa gcccgtcagg    3180
gcgcgtcagc gggtgttggc gggtgtcggg gctggcttaa ctatgcggca tcagagcaga    3240
ttgtactgag agtgcaccat atgcggtgtg aaataccgca cagatgcgta aggagaaaat    3300
accgcatcag gcgccttaa gggcctcgtg atacgcctat ttttataggt taatgtcatg    3360
ataataatgg tttcttagac gtcaggtggc acttttcggg gaaatgtgcg cggaacccct    3420
atttgtttat ttttctaaat acattcaaat atgtatccgc tcatgagaca ataaccctga    3480
taaatgcttc aataatattg aaaaaggaag agtatgagta ttcaacattt ccgtgtcgcc    3540
cttattccct tttttgcggc attttgcctt cctgtttttg ctcacccaga aacgctggtg    3600
aaagtaaaag atgctgaaga tcagttgggt gcacgagtgg gttacatcga actggatctc    3660
aacagcggta agatccttga gagttttcgc cccgaagaac gttttccaat gatgagcact    3720
tttaaagttc tgctatgtgg cgcggtatta tcccgtattg acgccgggca agagcaactc    3780
ggtcgccgca tacactattc tcagaatgac ttggttgagt actcaccagt cacagaaaag    3840
catcttacgg atggcatgac agtaagagaa ttatgcagtg ctgccataac catgagtgat    3900
aacactgcgg ccaacttact tctgacaacg atcggaggac cgaaggagct aaccgctttt    3960
ttgcacaaca tgggggatca tgtaactcgc cttgatcgtt gggaaccgga gctgaatgaa    4020
gccataccaa acgacgagcg tgacaccacg atgcctgtag caatggcaac aacgttgcgc    4080
aaactattaa ctggcgaact acttactcta gcttcccggc aacaattaat agactggatg    4140
gaggcggata aagttgcagg accacttctg cgctcggccc ttccggctgg ctggtttatt    4200
gctgataaat ctggagccgg tgagcgtggg tctcgcggta tcattgcagc actggggcca    4260
gatggtaagc cctcccgtat cgtagttatc tacacgacgg ggagtcaggc aactatggat    4320
gaacgaaata gacagatcgc tgagataggt gcctcactga ttaagcattg gtaactgtca    4380
gaccaagttt actcatatat actttagatt gatttaaaac ttcatttttta atttaaaagg    4440
atctaggtga agatcctttt tgataatctc atgaccaaaa tcccttaacg tgagttttcg    4500
ttccactgag cgtcagaccc cgtagaaaag atcaaaggat cttcttgaga tccttttttt    4560
ctgcgcgtaa tctgctgctt gcaaacaaaa aaaccaccgc taccagcggt ggtttgtttg    4620
ccggatcaag agctaccaac tcttttttccg aaggtaactg gcttcagcag agcgcagata    4680
ccaaatactg tccttctagt gtagccgtag ttaggccacc acttcaagaa ctctgtagca    4740
ccgcctacat acctcgctct gctaatcctg ttaccagtgg ctgctgccag tggcgataag    4800
tcgtgtctta ccgggttgga ctcaagacga tagttaccgg ataagcgcag cggtcgggc    4860
tgaacggggg gttcgtgcac acagcccagc ttggagcgaa cgacctacac cgaactgaga    4920
tacctacagc gtgagcattg agaaagcgcc acgcttcccg aagggagaaa ggcggacagg    4980
tatccggtaa gcggcagggt cggaacagga gagcgcacga gggagcttcc agggggaaac    5040
gcctggtatc tttatagtcc tgtcgggttt cgccacctct gacttgagcg tcgatttttg    5100
tgatgctcgt cagggggggcg gagcctatgg aaaaacgcca gcaacgcggc cttttttacgg    5160
ttcctggcct tttgctggcc ttttgctcac atgttctttc ctgcgttatc ccctgattct    5220
gtggataacc gtattaccgc ctttgagtga gctgataccg ctcgccgcag ccgaacgacc    5280
```

-continued

```
gagcgcagcg agtcagtgag cgaggaagcg gaagagcgcc caatacgcaa accgcctctc      5340
cccgcgcgtt ggccgattca ttaatgcagc tggcacgaca ggtttcccga ctggaaagcg      5400
ggcagtgagc gcaacgcaat taatgtgagt tagctcactc attaggcacc ccaggcttta      5460
cactttatgc ttccggctcg tatgttgtgt ggaattgtga gcggataaca atttcacaca      5520
ggaaacagct atgaccatga ttacgccaag ctgtaagttt aaacatgatc ttactaacta      5580
actattctca tttaaatttt cagagcttaa aaatggctga aatcactcac aacgatggat      5640
acgctaacaa cttggaaatg aaataagctt gcatgcctgc agagcaaaaa aatactgctt      5700
ttccttgcaa aattcggtgc tttcttcaaa gagaaacttt tgaagtcggc gcgagcattt      5760
ccttctttga cttctctctt tccgccaaaa agcctagcat ttttattgat aatttgatta      5820
cacacactca gagttcttcg acatgataaa gtgtttcatt ggcactcgcc ctaacagtac      5880
atgacaaggg cggattatta tcgatcgata ttgaagacaa actccaaatg tgtgctcatt      5940
ttggagcccc gtgtgggca gctgctctca atatattact agggagacga ggaggggac      6000 cttatcgaac gtcgcatgag ccattctttc ttctttatgc actctcttca ctctctcaca      6060
cattaatcga ttcatagact cccatattcc ttgatgaagg tgtgggtttt tagcttttt       6120 tcccgatttg taaaggaag aggctgacga tgttaggaaa aagagaacgg agccgaaaaa       6180
acatccgtag taagtcttcc ttttaagccg acactttta gacagcattc gccgctagtt       6240
ttgaagttta aattttaaaa aataaaaatt agtttcaatt ttttttaatt actaaatagg      6300
caaaagtttt ttcaagaact ctagaaaaac tagcttaatt catgggtact agaaaaattc      6360
ttgttttaaa tttaatattt atcttaagat gtaattacga gaagcttttt tgaaaattct      6420
caattaaaag aatttgccga tttagaataa aagtcttcag aaatgagtaa aagctcaaat      6480
tagaagtttg tttttaaagg aaaaacacga aaaagaaca ctatttatct tttcctcccc       6540
gcgtaaaatt agttgttgtg ataatagtga tccgctgtct atttgcactc ggctcttcac      6600
accgtgcttc ctctcacttg acccaacagg aaaaaaaaac atcacgtctg agacggtgaa      6660
ttgccttatc aagagcgtcg tctctttcac ccagtaacaa aaaaatttg gtttctttac       6720 tttatattta tgtaggtcac aaaaaaaag tgatgcagtt ttgtgggtcg gttgtctcca       6780
caccacctcc gcctcagca gcacacaatc atcttcgtgt gttctcgacg attccttgta       6840
tgccgcggtc gtgaatgcac cacattcgac gcgcaactac acaccacact cactttcggt      6900
ggtattacta cacgtcatcg ttgttcgtag tctcccgctc tttcgtcccc actcactcct      6960
cattattccc cttggtgtat tgattttttt taaatgtac accactcctg acgtttctac       7020
cttcttgttt tccgtccatt tagattttat ctggaaattt ttttaaaatt ttaggccaga      7080
gagttctagt tcttgttcta aaagtctagg tcagacatac attttctatt tctcatcaaa     7140 aaaaagttg ataagaaaa ctggttattc agaaagagtg tgtctcgttg aaattgattc        7200 aaaaaaaat tcccaccct cgcttgtttc tcaaatatg agatcaacgg attttttcct         7260
tctcgattca atttttttgct gcgctctgtc tgccaaagtg tgtgtgtccg agcaaaagat     7320
gagagaattt acaaacagaa atgaaaaaaa gttggccaaa taatgaagtt ttatccgaga      7380
ttgatgggaa agatattaat gttctttacg gtttggaggg gagagagaga tagattttcg      7440
catcaaactc cgcctttac atgtctttta gaatctaaaa tagattttc tcatcatttt        7500 taatagaaaa tcgagaaatt acagtaattt cgcaattttc ttgccaaaaa tacacgaaat      7560
ttgtgggtct cgccacgatc tcggtcttag tggttcattt ggtttaaaag tttataaaat      7620
ttcaaattct agtgtttaat ttccgcataa ttggacctaa aatgggtttt tgtcatcatt      7680
```

-continued

```
ttcaacaaga aatcgtgaaa atcctgttgt ttcgcaattt tcttttcaaa aatacacgaa    7740
atatatggta atttcccgaa atattgaggg tctcgccacg atttcagtca cagtggccag    7800
gatttatcac gaaaaaagtt cgcctagtct cacatttccg gaaaaccgaa tctaaattag    7860 tttttttgtca tcattttgaa caaaaaatcg agacatccct atagtttcgc aatttttcgtc   7920 gcttttctct ccaaaaatga cagtctagaa ttaaaattcg ctggaactgg gaccatgata    7980
tcttttctcc ccgttttttca ttttattttt tattacactg gattgactaa aggtcaccac    8040
caccgccagt gtgtgccata tcacacacac acacacacac aatgtcgaga ttttatgtgt    8100
tatccctgct tgatttcgtt ccgttgtctc tctctctcta ttcatctttt gagccgagaa    8160
gctccagaga atggagcaca caggatcccg gcgcgcgatg tcgtcgggag atggcgccgc    8220
ctgggaagcc gccgagagat atcagggaag atcgtctgat ttctcctcgg atgccacctc    8280
atctctcgag tttctccgcc tgttactccc tgccgaacct gatatttccc                8330
```

<210> SEQ ID NO 4
<211> LENGTH: 6470
<212> TYPE: DNA
<213> ORGANISM: Artificial Sequence
<220> FEATURE:
<223> OTHER INFORMATION: Description of Artificial Sequence:plasmid DNA

<400> SEQUENCE: 4

```
aagcttgcat gcctgcaggc cttggtcgac tctagacact tttcagctac ctagatacat     60
ggatatcccc gcctcccaat ccacccaccc agggaaaaag aagggctcgc cgaaaaatca    120
aagttatctc caggctcgcg catcccaccg agcggttgac ttctctccac cacttttcat    180
tttaaccctc ggggtacggg attggccaaa ggacccaaag gtatgtttcg aatgatacta    240
acataacata gaacatttc aggaggaccc ttgcttggag ggtaccgagc tcagaaaaaa    300
tgactgctcc aaagaagaag cgtaaggtac cggtaatgaa cacgattaac atcgctaaga    360
acgacttctc tgacatcgaa ctggctgcta tcccgttcaa cactctggct gaccattacg    420
gtgagcgttt agctcgcgaa cagttggccc ttgagcatga gtcttacgag atgggtgaag    480
cacgcttccg caagatgttt gagcgtcaac ttaaagctgg tgaggttgcg gataacgctg    540
ccgccaagcc tctcatcact accctactcc ctaagatgat gcacgcatc aacgactggt    600 ttgaggaagt gaaagctaag cgcggcaagc gcccgacagc cttccagttc ctgcaagaaa    660
tcaagccgga agccgtagcg tacatcacca ttaagaccac tctggcttgc ctaaccagtg    720
ctgacaatac aaccgttcag gctgtagcaa gcgcaatcgg tcgggccatt gaggacgagg    780
ctcgcttcgg tcgtatccgt gaccttgaag ctaagcactt caagaaaaac gttgaggaac    840
aactcaacaa gcgcgtaggg cacgtctaca agaaagcatt tatgcaagtt gtcgaggctg    900
acatgctctc taagggtcta ctcggtggcg aggcgtggtc ttcgtggcat aaggaagact    960
ctattcatgt aggagtacgc tgcatcgaga tgctcattga gtcaaccgga atggttagct   1020
tacaccgcca aaatgctggc gtagtaggtc aagactctga gactatcgaa ctcgcacctg   1080
aatacgctga ggctatcgca acccgtgcag gtgcgctggc tggcatctct ccgatgttcc   1140
aaccttgcgt agttcctcct aagccgtgga ctggcattac tggtggtggc tattgggcta   1200
acggtcgtcg tcctctggcg ctggtgcgta ctcacagtaa gaaagcactg atgcgctacg   1260
aagacgttta catgcctgag gtgtacaaag cgattaacat tgcgcaaaac accgcatgga   1320
aaatcaacaa gaaagtccta gcggtcgcca acgtaatcac caagtggaag cattgtccgg   1380
```

-continued

```
tcgaggacat ccctgcgatt gagcgtgaag aactcccgat gaaaccggaa gacatcgaca    1440
tgaatcctga ggctctcacc gcgtggaaac gtgctgccgc tgctgtgtac cgcaaggaca    1500
gggctcgcaa gtctcgccgt atcagccttg agttcatgct tgagcaagcc aataagtttg    1560
ctaaccataa ggccatctgg ttcccttaca acatggactg gcgcggtcgt gtttacgccg    1620
tgtcaatgtt caacccgcaa ggtaacgata tgaccaaagg actgcttacg ctggcgaaag    1680
gtaaaccaat cggtaaggaa ggttactact ggctgaaaat ccacggtgca aactgtgcgg    1740
gtgtcgataa ggttccgttc cctgagcgca tcaagttcat tgaggaaaac cacgagaaca    1800
tcatggcttg cgctaagtct ccactggaga cacttggtg ggctgagcaa gattctccgt    1860
tctgcttcct tgcgttctgc tttgagtacg ctggggtaca gcaccacggc ctgagctata    1920
actgctccct tccgctggcg tttgacgggt cttgctctgg catccagcac ttctccgcga    1980
tgctccgaga tgaggtaggt ggtcgcgcgg ttaacttgct tcctagtgag accgttcagg    2040
acatctacgg gattgttgct aagaaagtca acgagattct acaagcagac gcaatcaatg    2100
ggaccgataa cgaagtagtt accgtgaccg atgagaacac tggtgaaatc tctgagaaag    2160
tcaagctggg cactaaggca ctggctggtc aatggctggc tcacggtgtt actcgcagtg    2220
tgactaagcg ttcagtcatg acgctggctt acgggtccaa agagttcggc ttccgtcaac    2280
aagtgctgga agataccatt cagccagcta ttgattccgg caagggtccg atgttcactc    2340
agccgaatca ggctgctgga tacatggcta agctgatttg ggaatctgtg agcgtgacgg    2400
tggtagctgc ggttgaagca atgaactggc ttaagtctgc tgctaagctg ctggctgctg    2460
aggtcaaaga taagaagact ggagagattc ttcgcaagcg ttgcgctgtg cattgggtaa    2520
ctcctgatgg tttccctgtg tggcaggaat acaagaagcc tattcagacg cgcttgaacc    2580
tgatgttcct cggtcagttc cgcttacagc ctaccattaa caccaacaaa gatagcgaga    2640
ttgatgcaca caaacaggag tctggtatcg ctcctaactt tgtacacagc caagacggta    2700
gccaccttcg taagactgta gtgtgggcac acgagaagta cggaatcgaa tcttttgcac    2760
tgattcacga ctccttcggt accattccgg ctgacgctgc gaacctgttc aaagcagtgc    2820
gcgaaactat ggttgacaca tatgagtctt gtgatgtact ggctgatttc tacgaccagt    2880
tcgctgacca gttgcacgag tctcaattgg acaaaatgcc agcacttccg gctaaaggta    2940
acttgaacct ccgtgacatc ttagagtcgg acttcgcgtt cgcgtaagaa ttccaactga    3000
gcgccggtcg ctaccattac caacttgtct ggtgtcaaaa ataataggggg ccgctgtcat    3060 cagagtaagt ttaaactgag ttctactaac taacgagtaa tatttaaatt ttcagcatct    3120
cgcgcccgtg cctctgactt ctaagtccaa ttactcttca acatccctac atgctctttc    3180
tccctgtgct cccaccccct attttgtta ttatcaaaaa aacttcttct taatttcttt    3240 gtttttagc ttctttttaag tcacctctaa caatgaaatt gtgtagattc aaaaatagaa    3300
ttaattcgta ataaaaagtc gaaaaaaatt gtgctccctc cccccattaa taataattct    3360
atcccaaaat ctacacaatg ttctgtgtac acttcttatg tttttttttac ttctgataaa    3420 ttttttttga aacatcatag aaaaaaccgc acacaaaata ccttatcata tgttacgttt    3480
cagtttatga ccgcaatttt tatttcttcg cacgtctggg cctctcatga cgtcaaatca    3540
tgctcatcgt gaaaagttt tggagtattt ttggaatttt tcaatcaagt gaaagtttat    3600
gaaattaatt ttcctgcttt tgcttttgg gggtttcccc tattgtttgt caagagtttc    3660
gaggacggcg ttttcttgc taaaatcaca agtattgatg agcacgatgc aagaaagatc    3720
ggaagaaggt ttgggtttga ggctcagtgg aaggtgagta gaagttgata atttgaaagt    3780
```

-continued

```
ggagtagtgt ctatggggtt tttgccttaa atgacagaat acattcccaa tataccaaac    3840
ataactgttt cctactagtc ggccgtacgg gcccttcgt ctcgcgcgtt tcggtgatga    3900
cggtgaaaac ctctgacaca tgcagctccc ggagacggtc acagcttgtc tgtaagcgga    3960
tgccgggagc agacaagccc gtcagggcgc gtcagcgggt gttggcgggt gtcggggctg    4020
gcttaactat gcggcatcag agcagattgt actgagagtg caccatatgc ggtgtgaaat    4080
accgcacaga tgcgtaagga gaaaataccg catcaggcgg ccttaagggc ctcgtgatac    4140
gcctattttt ataggttaat gtcatgataa taatggtttc ttagacgtca ggtggcactt    4200
ttcggggaaa tgtgcgcgga acccctattt gtttattttt ctaaatacat tcaaatatgt    4260
atccgctcat gagacaataa ccctgataaa tgcttcaata atattgaaaa aggaagagta    4320
tgagtattca acatttccgt gtcgccctta ttcccttttt tgcggcattt tgccttcctg    4380
tttttgctca cccagaaacg ctggtgaaag taaaagatgc tgaagatcag ttgggtgcac    4440
gagtgggtta catcgaactg gatctcaaca gcggtaagat ccttgagagt tttcgccccg    4500
aagaacgttt tccaatgatg agcactttta aagttctgct atgtggcgcg gtattatccc    4560
gtattgacgc cgggcaagag caactcggtc gccgcataca ctattctcag aatgacttgg    4620
ttgagtactc accagtcaca gaaaagcatc ttacggatgg catgacagta agagaattat    4680
gcagtgctgc cataaccatg agtgataaca ctgcggccaa cttacttctg acaacgatcg    4740
gaggaccgaa ggagctaacc gcttttttgc acaacatggg ggatcatgta actcgccttg    4800
atcgttggga accggagctg aatgaagcca taccaaacga cgagcgtgac accacgatgc    4860
ctgtagcaat ggcaacaacg ttgcgcaaac tattaactgg cgaactactt actctagctt    4920
cccggcaaca attaatagac tggatggagg cggataaagt tgcaggacca cttctgcgct    4980
cggcccttcc ggctggctgg tttattgctg ataaatctgg agccggtgag cgtgggtctc    5040
gcggtatcat tgcagcactg gggccagatg gtaagccctc ccgtatcgta gttatctaca    5100
cgacggggag tcaggcaact atggatgaac gaaatagaca gatcgctgag ataggtgcct    5160
cactgattaa gcattggtaa ctgtcagacc aagtttactc atatatactt tagattgatt    5220
taaaacttca ttttaatt aaaaggatct aggtgaagat cctttttgat aatctcatga    5280
ccaaaatccc ttaacgtgag ttttcgttcc actgagcgtc agaccccgta gaaaagatca    5340
aaggatcttc ttgagatcct ttttttctgc gcgtaatctg ctgcttgcaa acaaaaaaac    5400
caccgctacc agcggtggtt tgtttgccgg atcaagagct accaactctt tttccgaagg    5460
taactggctt cagcagagcg cagataccaa atactgtcct tctagtgtag ccgtagttag    5520
gccaccactt caagaactct gtagcaccgc ctacatacct cgctctgcta atcctgttac    5580
cagtggctgc tgccagtggc gataagtcgt gtcttaccgg gttggactca agacgatagt    5640
taccggataa ggcgcagcgg tcgggctgaa cggggggttc gtgcacacag cccagcttgg    5700
agcgaacgac ctacaccgaa ctgagatacc tacagcgtga gcattgagaa agcgccacgc    5760
ttcccgaagg gagaaaggcg gacaggtatc cggtaagcgg cagggtcgga acaggagagc    5820
gcacgaggga gcttccaggg ggaaacgcct ggtatcttta tagtcctgtc gggtttcgcc    5880
acctctgact tgagcgtcga tttttgtgat gctcgtcagg gggcggagc ctatggaaaa    5940
acgccagcaa cgcggccttt ttacggttcc tggccttttg ctggccttt gctcacatgt    6000
tctttcctgc gttatcccct gattctgtgg ataaccgtat taccgccttt gagtgagctg    6060
ataccgctcg ccgcagccga acgaccgagc gcagcgagtc agtgagcgag gaagcggaag    6120
```

-continued

```
agcgcccaat acgcaaaccg cctctccccg cgcgttggcc gattcattaa tgcagctggc      6180
acgacaggtt tcccgactgg aaagcgggca gtgagcgcaa cgcaattaat gtgagttagc      6240
tcactcatta ggcaccccag gctttacact ttatgcttcc ggctcgtatg ttgtgtggaa      6300
ttgtgagcgg ataacaattt cacacaggaa acagctatga ccatgattac gccaagctgt      6360
aagtttaaac atgatcttac taactaacta ttctcattta aattttcaga gcttaaaaat      6420
ggctgaaatc actcacaacg atggatacgc taacaacttg gaaatgaaat                 6470
```

<210> SEQ ID NO 5
<211> LENGTH: 4689
<212> TYPE: DNA
<213> ORGANISM: Artificial Sequence
<220> FEATURE:
<223> OTHER INFORMATION: Description of Artificial Sequence:plasmid DNA

<400> SEQUENCE: 5

```
aagcttgcat gcctgcaggc cttggtcgac tctagacact tttcagctac ctagatacat        60
ggatatcccc gcctcccaat ccacccaccc agggaaaaag aagggctcgc gaaaaatca       120 aagttatctc caggctcgcg catcccaccg agcggttgac ttctctccac cacttttcat       180
tttaaccctc ggggtacggg attggccaaa ggacccaaag gtatgtttcg aatgatacta       240
acataacata gaacattttc aggaggaccc ttgcttggag ggtaccgagc tcccgggatt       300
aatacgactc actataccgg tagaaaaaat gagtaaagga agaactttt tcactggagt       360 tgtcccaatt cttgttgaat tagatggtga tgttaatggg cacaaatttt ctgtcagtgg       420
agagggtgaa ggtgatgcaa catacggaaa acttaccctt aaatttattt gcactactgg       480
aaaactacct gttccatggg taagtttaaa catatatata ctaactaacc ctgattattt       540
aaattttcag ccaacacttg tcactacttt ctgttatggt gttcaatgct tctcgagata       600
cccagatcat atgaaacggc atgactttt caagagtgcc atgcccgaag gttatgtaca       660
ggaaagaact atatttttca agatgacgg gaactacaag acacgtaagt ttaaacagtt       720
cggtactaac taaccataca tatttaaatt ttcaggtgct gaagtcaagt ttgaaggtga       780 taccctgtt aatagaatcg agttaaaagg tattgatttt aagaagatg gaaacattct       840 tggacacaaa ttggaataca actataactc acacaatgta tacatcatgg cagacaaaca       900
aaagaatgga atcaaagttg taagtttaaa catgatttta ctaactaact aatctgattt       960
aaattttcag aacttcaaaa ttagacacaa cattgaagat ggaagcgttc aactagcaga      1020
ccattatcaa caaaatactc caattggcga tggccctgtc cttttaccag acaaccatta      1080
cctgtccaca caatctgccc tttcgaaaga tcccaacgaa agagagacc acatggtcct      1140 tcttgagttt gtaacagctg ctgggattac acatggcatg gatgaactat acaaatagca      1200
ttcgtagaat tccaactgag cgccggtcgc taccattacc aacttgtctg gtgtcaaaaa      1260 taatagggc gcgtgtcatc agagtaagtt taaactgagt tctactaact aacgagtaat      1320
atttaaattt tcagcatctc gcgcccgtgc ctctgacttc taagtccaat tactcttcaa      1380
catccctaca tgctctttct ccctgtgctc caccccta tttttgttat tatcaaaaaa       1440
acttcttctt aattctttg ttttttagct tcttttaagt cacctctaac aatgaaattg       1500
tgtagattca aaaatagaat taattcgtaa taaaagtcg aaaaaattg tgctccctcc       1560 ccccattaat aataattcta tcccaaaatc tacacaatgt tctgtgtaca cttcttatgt       1620 ttttttact tctgataaat tttttttgaa acatcataga aaaaccgca cacaaaatac       1680 cttatcatat gttacgtttc agtttatgac cgcaattttt atttcttcgc acgtctgggc      1740
```

```
ctctcatgac gtcaaatcat gctcatcgtg aaaaagttttt ggagtatttt tggaattttt    1800
caatcaagtg aaagtttatg aaattaattt tcctgctttt gcttttgg ggtttcccct      1860
attgtttgtc aagagtttcg aggacggcgt ttttcttgct aaaatcacaa gtattgatga    1920
gcacgatgca agaaagatcg aagaaggtt tgggtttgag gctcagtgga aggtgagtag     1980
aagttgataa tttgaaagtg gagtagtgtc tatggggttt ttgccttaaa tgacagaata    2040
cattcccaat ataccaaaca taactgtttc ctactagtcg gccgtacggg cccttttcgtc   2100
tcgcgcgttt cggtgatgac ggtgaaaacc tctgacacat gcagctcccg gagacggtca   2160
cagcttgtct gtaagcggat gccgggagca gacaagcccg tcaggcgcg tcagcgggtg    2220
ttggcgggtg tcgggctgg cttaactatg cggcatcaga gcagattgta ctgagagtgc    2280
accatatgcg gtgtgaaata ccgcacagat gcgtaaggag aaaataccgc atcaggcggc   2340
cttaagggcc tcgtgatacg cctattttta taggttaatg tcatgataat aatggtttct   2400
tagacgtcag gtggcacttt tcggggaaat gtgcgcggaa ccctatttg tttatttttc    2460
taaatacatt caaatatgta tccgctcatg agacaataac cctgataaat gcttcaataa   2520
tattgaaaaa ggaagagtat gagtattcaa catttccgtg tcgcccttat tccctttttt   2580
gcggcatttt gccttcctgt ttttgctcac ccagaaacgc tggtgaaagt aaaagatgct   2640
gaagatcagt tgggtgcacg agtgggttac atcgaactgg atctcaacag cggtaagatc   2700
cttgagagtt tcgccccga agaacgtttt ccaatgatga gcacttttaa agttctgcta   2760
tgtggcgcgg tattatcccg tattgacgcc gggcaagagc aactcggtcg ccgcatacac   2820
tattctcaga tgacttggt tgagtactca ccagtcacag aaaagcatct tacggatggc   2880
atgacagtaa gagaattatg cagtgctgcc ataaccatga gtgataacac tgcggccaac   2940
ttacttctga caacgatcgg aggaccgaag gagctaaccg cttttttgca caacatgggg   3000
gatcatgtaa ctcgccttga tcgttgggaa ccggagctga atgaagccat accaaacgac   3060
gagcgtgaca ccacgatgcc tgtagcaatg gcaacaacgt tgcgcaaact attaactggc   3120
gaactactta ctctagcttc ccggcaacaa ttaatagact ggatggaggc ggataaagtt   3180
gcaggaccac ttctgcgctc ggcccttccg gctggctggt ttattgctga taaatctgga   3240
gccggtgagc gtgggtctcg cggtatcatt gcagcactgg ggccagatgg taagccctcc   3300
cgtatcgtag ttatctacac gacggggagt caggcaacta tggatgaacg aaatagacag   3360
atcgctgaga taggtgcctc actgattaag cattggtaac tgtcagacca gtttactca    3420
tatatacttt agattgattt aaaacttcat ttttaattta aaaggatcta ggtgaagatc   3480
cttttttgata atctcatgac caaaatccct aacgtgagt tttcgttcca ctgagcgtca   3540
gaccccgtag aaaagatcaa aggatcttct tgagatcctt ttttctgcg cgtaatctgc   3600
tgcttgcaaa caaaaaaacc accgctacca gcggtggttt gtttgccgga tcaagagcta   3660
ccaactcttt ttccgaaggt aactggcttc agcagagcgc agataccaaa tactgtcctt   3720
ctagtgtagc cgtagttagg ccaccacttc aagaactctg tagcaccgcc tacatacctc   3780
gctctgctaa tcctgttacc agtggctgct gccagtggcg ataagtcgtg tcttaccggg   3840
ttggactcaa gacgatagtt accggataag gcgcagcggt cgggctgaac ggggggttcg   3900
tgcacacagc ccagcttgga gcgaacgacc tacaccgaac tgagatacct acagcgtgag   3960
cattgagaaa gcgccacgct tcccgaaggg agaaaggcgg acaggtatcc ggtaagcggc   4020
agggtcggaa caggagagcg cacgagggag cttccagggg gaaacgcctg gtatctttat   4080
```

-continued

| | |
|---|---|
| agtcctgtcg ggtttcgcca cctctgactt gagcgtcgat ttttgtgatg ctcgtcaggg | 4140 |
| gggcggagcc tatggaaaaa cgccagcaac gcggcctttt tacggttcct ggccttttgc | 4200 |
| tggccttttg ctcacatgtt ctttcctgcg ttatccctg attctgtgga taaccgtatt | 4260 |
| accgcctttg agtgagctga taccgctcgc cgcagccgaa cgaccgagcg cagcgagtca | 4320 |
| gtgagcgagg aagcggaaga gcgcccaata cgcaaaccgc ctctccccgc gcgttggccg | 4380 |
| attcattaat gcagctggca cgacaggttt cccgactgga aagcgggcag tgagcgcaac | 4440 |
| gcaattaatg tgagttagct cactcattag gcaccccagg ctttacactt tatgcttccg | 4500 |
| gctcgtatgt tgtgtggaat tgtgagcgga taacaatttc acacaggaaa cagctatgac | 4560 |
| catgattacg ccaagctgta agtttaaaca tgatcttact aactaactat tctcatttaa | 4620 |
| attttcagag cttaaaaatg gctgaaatca ctcacaacga tggatacgct aacaacttgg | 4680 |
| aaatgaaat | 4689 |

<210> SEQ ID NO 6
<211> LENGTH: 5175
<212> TYPE: DNA
<213> ORGANISM: Artificial Sequence
<220> FEATURE:
<223> OTHER INFORMATION: Description of Artificial Sequence:plasmid DNA

<400> SEQUENCE: 6

| | |
|---|---|
| gatcccggcg cgcgatgtcg tcgggagatg gcgccgcctg ggaagccgcc gagagatatc | 60 |
| agggaagatc gtctgatttc tcctcggatg ccacctcatc tctcgagttt ctccgcctgt | 120 |
| tactccctgc cgaacctgat atttcccgtt gtcgtaaaga gatgttttta ttttactta | 180 |
| caccgggtcc tctctctctg ccagcacagc tcagtgttgg ctgtgtgctc gggctcctgc | 240 |
| caccggcggc ctcatcttct tcttcttctt ctctcctgct ctcgcttatc acttcttcat | 300 |
| tcattcttat tcctttcat catcaaacta gcatttctta cttatttat tttttcaat | 360 |
| tttcaatttt cagataaaac caaactactt gggttacagc cgtcaacaga tccccgggat | 420 |
| tggccaaagg acccaaaggt atgtttcgaa tgatactaac ataacataga acattttcag | 480 |
| gaggaccctt gcttggaggg taccggtaga aaaaatgagt aaaggagaag aacttttcac | 540 |
| tggagttgtc ccaattcttg ttgaattaga tggtgatgtt aatgggcaca aatttctgt | 600 |
| cagtggagag ggtgaaggtg atgcaacata cggaaaactt acccttaaat ttatttgcac | 660 |
| tactggaaaa ctacctgttc catgggtaag tttaaacata tatactaa ctaaccctga | 720 |
| ttatttaaat tttcagccaa cacttgtcac tactttctgt tatggtgttc aatgcttctc | 780 |
| gagatacccca gatcatatga aacggcatga cttttttcaag agtgccatgc ccgaaggtta | 840 |
| tgtacaggaa agaactatat ttttcaaaga tgacgggaac tacaagacac gtaagtttaa | 900 |
| acagttcggt actaactaac catacatatt taaatttca ggtgctgaag tcaagtttga | 960 |
| aggtgatacc cttgttaata gaatcgagtt aaaaggtatt gattttaaag aagatggaaa | 1020 |
| cattcttgga cacaaattgg aatacaacta taactcacac aatgtataca tcatggcaga | 1080 |
| caaacaaaag aatggaatca agttgtaag tttaaacttg gacttactaa ctaacggatt | 1140 |
| atatttaaat tttcagaact tcaaaattag acacaacatt gaagatggaa gcgttcaact | 1200 |
| agcagaccat tatcaacaaa atactccaat tggcgatggc cctgtccttt taccagacaa | 1260 |
| ccattacctg tccacacaat ctgccctttc gaaagatccc aacgaaaaga gagaccacat | 1320 |
| ggtccttctt gagtttgtaa cagctgctgg gattacacat ggcatggatg aactatacaa | 1380 |
| atagcattcg tagaattcca actgagcgcc ggtcgctacc attaccaact tgtctggtgt | 1440 |

-continued

```
caaaaataat agggccgct gtcatcagag taagttaaa ctgagttcta ctaactaacg      1500
agtaatattt aaattttcag catctcgcgc ccgtgcctct gacttctaag tccaattact      1560
cttcaacatc cctacatgct cttttctccct gtgctcccac ccctatttt tgttattatc     1620 aaaaaaactt cttcttaatt tctttgtttt ttagcttctt ttaagtcacc tctaacaatg      1680
aaattgtgta gattcaaaaa tagaattaat tcgtaataaa aagtcgaaaa aaattgtgct      1740 ccctccccc attaataata attctatccc aaaatctaca caatgttctg tgtacacttc      1800
ttatgttttt tttacttctg ataaattttt tttgaaacat catagaaaaa accgcacaca      1860 aaataccta tcatatgtta cgtttcagtt tatgaccgca atttttattt cttcgcacgt      1920
ctgggcctct catgacgtca aatcatgctc atcgtgaaaa agttttggag tatttttgga      1980
atttttcaat caagtgaaag tttatgaaat taatttcct gcttttgctt tttggggtt       2040 tcccctattg tttgtcaaga gtttcgagga cggcgttttt cttgctaaaa tcacaagtat      2100
tgatgagcac gatgcaagaa agatcggaag aaggtttggg tttgaggctc agtggaaggt      2160
gagtagaagt tgataatttg aaagtggagt agtgtctatg gggttttgc cttaaatgac       2220 agaatacatt cccaatatac caaacataac tgtttcctac tagtcggccg tacgggcccg      2280
gtacccagct tttgttccct ttagtgaggg ttaattgcgc gcttggcgta atcatggtca      2340 tagctgttc ctgtgtgaaa ttgttatccg ctcacaattc cacacaacat acgagccgga       2400
agcataaagt gtaaagcctg gggtgcctaa tgagtgagct aactcacatt aattgcgttg      2460
cgctcactgc ccgctttcca gtcgggaaac ctgtcgtgcc agctgcatta atgaatcggc      2520
caacgcgcgg ggagaggcgg tttgcgtatt gggcgctctt ccgcttcctc gctcactgac      2580
tcgctgcgct cggtcgttcg gctgcggcga gcggtatcag ctcactcaaa ggcggtaata      2640
cggttatcca cagaatcagg ggataacgca ggaaagaaca tgtgagcaaa aggccagcaa      2700
aaggccagga accgtaaaaa ggccgcgttg ctggcgtttt tccataggct ccgcccccct      2760
gacgagcatc acaaaaatcg acgctcaagt cagaggtggc gaaacccgac aggactataa      2820
agataccagg cgtttccccc tggaagctcc ctcgtgcgct ctcctgttcc gaccctgccg      2880
cttaccggat acctgtccgc ctttctccct tcgggaagcg tggcgctttc tcatagctca      2940
cgctgtaggt atctcagttc ggtgtaggtc gttcgctcca agctgggctg tgtgcacgaa      3000
ccccccgttc agcccgaccg ctgcgcctta tccggtaact atcgtcttga gtccaacccg      3060
gtaagacacg acttatcgcc actggcagca gccactggta acaggattag cagagcgagg      3120
tatgtaggcg gtgctacaga gttcttgaag tggtggccta actacggcta cactagaagg      3180
acagtatttg gtatctgcgc tctgctgaag ccagttacct tcggaaaaag agttggtagc      3240
tcttgatccg gcaaacaaac caccgctggt agcggtggtt ttttttgtttg caagcagcag      3300 attacgcgca gaaaaaaagg atctcaagaa gatcctttga tcttttctac ggggtctgac      3360
gctcagtgga acgaaaactc acgttaaggg attttggtca tgagattatc aaaaaggatc      3420
ttcacctaga tccttttaaa ttaaaaatga agttttaaat caatctaaag tatatatgag      3480
taaacttggt ctgacagtta ccaatgctta atcagtgagg cacctatctc agcgatctgt      3540
ctatttcgtt catccatagt tgcctgactc ccgtcgtgt agataactac gatacgggag       3600
ggcttaccat ctggccccag tgctgcaatg ataccgcgag acccacgctc accggctcca      3660
gatttatcag caataaacca gccagccgga agggccgagc gcagaagtgg tcctgcaact      3720
ttatccgcct ccatccagtc tattaattgt tgccgggaag ctagagtaag tagttcgcca      3780
```

-continued

| | |
|---|---|
| gttaatagtt tgcgcaacgt tgttgccatt gctacaggca tcgtggtgtc acgctcgtcg | 3840 |
| tttggtatgg cttcattcag ctccggttcc caacgatcaa ggcgagttac atgatccccc | 3900 |
| atgttgtgca aaaagcggt tagctccttc ggtcctccga tcgttgtcag aagtaagttg | 3960 |
| gccgcagtgt tatcactcat ggttatggca gcactgcata attctcttac tgtcatgcca | 4020 |
| tccgtaagat gcttttctgt gactggtgag tactcaacca agtcattctg agaatagtgt | 4080 |
| atgcggcgac cgagttgctc ttgcccggcg tcaatacggg ataataccgc gccacatagc | 4140 |
| agaactttaa aagtgctcat cattggaaaa cgttcttcgg ggcgaaaact ctcaaggatc | 4200 |
| ttaccgctgt tgagatccag ttcgatgtaa cccactcgtg cacccaactg atcttcagca | 4260 |
| tcttttactt tcaccagcgt ttctgggtga gcaaaaacag gaaggcaaaa tgccgcaaaa | 4320 |
| aagggaataa gggcgacacg gaaatgttga atactcatac tcttcctttt tcaatattat | 4380 |
| tgaagcattt atcagggtta ttgtctcatg agcggataca tatttgaatg tatttagaaa | 4440 |
| aataaacaaa taggggttcc gcgcacattt ccccgaaaag tgccacctaa attgtaagcg | 4500 |
| ttaatatttt gttaaaattc gcgttaaatt tttgttaaat cagctcattt tttaaccaat | 4560 |
| aggccgaaat cggcaaaatc ccttataaat caaaagaata gaccgagata gggttgagtg | 4620 |
| ttgttccagt ttggaacaag agtccactat taaagaacgt ggactccaac gtcaaagggc | 4680 |
| gaaaaaccgt ctatcagggc gatggcccac tacgtgaacc atcaccctaa tcaagttttt | 4740 |
| tggggtcgag gtgccgtaaa gcactaaatc ggaaccctaa agggagcccc cgatttagag | 4800 |
| cttgacgggg aaagccggcg aacgtggcga gaaaggaagg gaagaaagcg aaaggagcgg | 4860 |
| gcgctagggc gctggcaagt gtagcggtca cgctgcgcgt aaccaccaca cccgccgcgc | 4920 |
| ttaatgcgcc gctacaggg gcgtcccatt cgccattcag gctgcgcaac tgttgggaag | 4980 |
| ggcgatcggt gcgggcctct tcgctattac gccagctggc gaaaggggga tgtgctgcaa | 5040 |
| ggcgattaag ttgggtaacg ccagggtttt cccagtcacg acgttgtaaa acgacggcca | 5100 |
| gtgagcgcgc gtaatacgac tcactatagg gcgaattgga gctccaccgc ggtggcggcc | 5160 |
| gctctagaac tagtg | 5175 |

<210> SEQ ID NO 7
<211> LENGTH: 12482
<212> TYPE: DNA
<213> ORGANISM: Artificial Sequence
<220> FEATURE:
<223> OTHER INFORMATION: Description of Artificial Sequence:plasmid DNA

<400> SEQUENCE: 7

| | |
|---|---|
| gatcctccaa aatcgtcttc cgctctgaaa aacgaaagtg gacctttgac atccgaaaaa | 60 |
| atgggcgaaa aaatgaaatt gagcttttg ggtcgaaaaa aatgttttta gaatgctgag | 120 |
| aacacgttaa acacgaagat catatttatt ttgagacccg gatgctctga aaatgtctga | 180 |
| catagattta aaaagcata tatatttt tcattttcaa cgtgaaagtt ttgtgcaact | 240 |
| ttatagaatc tcctattggc acattgtttt ttatttaact gaggcagttt ttgaacacct | 300 |
| ttttgaaact ttgaatctct ttgaagtata ctgtcgaaaa gactgacttg agcgttcgaa | 360 |
| atgccagaag aaaactatat ttgaatctcg cgctaaattg agaaatgcaa ccgcgctcca | 420 |
| ctggacaatt ggaaaaaaaa tttattcgga ggcgacaacg gtattttcga aattgatttt | 480 |
| ctgtgtattt tctcattttt tataaattct tctttgattt atcgttcgtt tgtgagaaat | 540 |
| taattgtat tcaactttt ttatagtaag ataccggtgg taccgctagc cgtacgaacc | 600 |
| cgggattggc caaaggaccc aaaggtatgt ttcgaatgat actaacataa catagaacat | 660 |

```
tttcaggagg accccttgctt ggagggtacc ggatgactgc tccaaagaag aagcgtaagc    720
tcatgaacac gattaacatc gctaagaacg acttctctga catcgaactg gctgctatcc    780
cgttcaacac tctggctgac cattacggtg agcgtttagc tcgcgaacag ttggcccttg    840
agcatgagtc ttacgagatg ggtgaagcac gcttccgcaa gatgtttgag cgtcaactta    900
aagctggtga ggttgcggat aacgctgccg ccaagcctct catcactacc ctactcccta    960
agatgattgc acgcatcaac gactggtttg aggaagtgaa agctaagcgc ggcaagcgcc   1020
cgacagcctt ccagttcctg caagaaatca gccggaagc cgtagcgtac atcaccatta    1080
agaccactct ggcttgccta accagtgctg acaatacaac cgttcaggct gtagcaagcg   1140
caatcggtcg ggccattgag gacgaggctc gcttcggtcg tatccgtgac cttgaagcta   1200
agcacttcaa gaaaaacgtt gaggaacaac tcaacaagcg cgtagggcac gtctacaaga   1260
aagcatttat gcaagttgtc gaggctgaca tgctctctaa gggtctactc ggtggcgagg   1320
cgtggtcttc gtggcataag gaagactcta ttcatgtagg agtacgctgc atcgagatgc   1380
tcattgagtc aaccggaatg gttagcttac accgccaaaa tgctggcgta gtaggtcaag   1440
actctgagac tatcgaactc gcacctgaat acgctgaggc tatcgcaacc cgtgcaggtg   1500
cgctggctgg catctctccg atgttccaac cttgcgtagt tcctcctaag ccgtggactg   1560
gcattactgg tggtggctat tgggctaacg gtcgtcgtcc tctggcgctg gtgcgtactc   1620
acagtaagaa agcactgatg cgctacgaag acgtttacat gcctgaggtg tacaaagcga   1680
ttaacattgc gcaaaacacc gcatggaaaa tcaacaagaa agtcctagcg gtcgccaacg   1740
taatcaccaa gtggaagcat tgtccggtcg aggacatccc tgcgattgag cgtgaagaac   1800
tcccgatgaa accggaagac atcgacatga atcctgaggc tctcaccgcg tggaaacgtg   1860
ctgccgctgc tgtgtaccgc aagacaaggc tcgcaagtct cgccgtatca gccttgagtt   1920
catgcttgag caagccaata agtttgctaa ccataaggcc atctggttcc cttacaacat   1980
ggactggcgc ggttcgtgtt tacgctgtgt caatgttcaa cccgcaaggt aacgatatga   2040
ccaaaggacg tcttacgctg gcgaaaggta aaccaatcgg taaggaaggt tactactggc   2100
tgaaaatcca cggtgcaaac tgtgcgggtg tcgataaggt ttcgtttcct gagcgcatca   2160
agttcattga ggaaaaccac gagaacatca tggcttgcgc taagtctcca ctggagaaca   2220
cttggtgggc tgagcaagat tctccgttct gcttccttgc gttctgcttt gagtacgctg   2280
gggtacagca ccacggcctg agctataact gctcccttcc gctggcgttt gacgggtctt   2340
gctctggcat ccagcacttc tccgcgatgc tccgagatga ggtaggtggt cgcgcggtta   2400
acttgcttcc tagtgaaacc gttcaggaca tctacgggat tgttgctaag aaagtcaacg   2460
agattctgca agcagacgca atcaatggga ccgataacga agtagttacc gtgaccgatg   2520
agaacactgg tgaaatctct gagaaagtca agctgggcac taaggcactg gctggtcaat   2580
ggctggctta cggtgttact cgcagtgtga ctaagcgttc agtcatgacg ctggcttacg   2640
ggtccaaaga gttcggcttc cgtcaacaag tgctggaaga taccattcag ccagctattg   2700
attccggcaa gggtctgatg ttcactcagc cgaatcaggc tgctggatac atggctaagc   2760
tgatttggga atccgtgagc gtgacggtgg tagctgcgcg ttgaagcaatg aactggctta   2820
agtctgctgc taagctgctg gctgctgagg tcaaagataa gaagactgga gagattcttc   2880
gcaagcgttg cgctgtgcat tgggtaactc ctgatggttt ccctgtgtgg caggaataca   2940
agaagcctat tcagacgcgc ttgaacctga tgttcctcgg tcagttccgc ttacagccta   3000
```

```
ccattaacac caacaaagat agcgagattg atgcacacaa acaggagtct ggtatcgctc   3060
ctaactttgt acacagccaa gacggtagcc accttcgtaa gactgtagtg tgggcacacg   3120
agaagtacgg aatcgaatct tttgcactga ttcacgactc cttcggtacc attccggctg   3180
acgctgcgaa cctgttcaaa gcagtgcgcg aaactatggt tgacacatat gagtcttgtg   3240
atgtactggc tgatttctac gaccagttcg ctgaccagtt gcacgagtct caattggaca   3300
aaatgccagc acttccggct aaaggtaact tgaacctccg tgacatctta gagtcggact   3360
tcgcgttcgc gtaagggccc tcgtcgagtc ggtcacaatc acctgaaact ccaaaggcag   3420
ccagtgagga acgtgaagaa gaagaaaaag agtcatctga acaggtttga ttttctttct   3480
ggtcaaaaag atgaaattat tgattttcag ccagatactc ccaaaactag cagcgagaag   3540
tctgcaagtc gttcacagtc gcccagagaa tcgcgggaag tgagccaaga ggtatgtttt   3600
tcaaaaatca taactgatc ataatttta ttgtttggtg aatttaagaa aataatattc   3660
gaaaattcct ctgaattatc aagattgcag tattaatttc gagaaaatt gagatattca   3720 tagagctatt gtaaattttc ttgatttcag actgaaactt cggaaaatca agagaaaatc   3780
aaagaaaagg atgacgggga tgatcagcct ggcacaccga acagctatag aagccgggaa   3840
acttcaccag ctccaaaaag gtccaaggag accaggtttg tcaaaagctt cctgcgatta   3900
attctcattt caatttttca gagaatcaga gtctcctgaa aaatccccgg ttcgttcaag   3960
atctcccaga aggtcttcag cacgttcccc gtcacgatct cctagacggc gccgagaaag   4020
aagctcagaa agaaagcaat ccgaagagcc agcaccgcta ccagagaaaa agaagaaga   4080 gccgctggat attctacgaa caagaaccgg aggagcatat attccacccg ccaaacttcg   4140
acttatgcaa caacagatta gtgataagca aagtgaacag tatcagagaa tgaattggga   4200
aagaatgaag aaaaagattc acggattggt taacagagtc aacgcgaaga atcttgttca   4260
aattgtcaga gaacttcttc aagagaatgt gattcgttca aagtgagtga aaaatcgaa   4320 ggaaaaggaa agaattaatt taatttttca ggggacttct ctgccgtgac attattcaag   4380
ctcaggcttt ctcaccagga ttctctaacg tctatgcagc tttggcggca gttatcaact   4440
cgaaattccc tcatgtcggt gaacttcttc tccgtcgtct gattgtacag ttcaaaagaa   4500
gtttccgtag aaatgacaga ggcgtcacgg tgaacgtgat caaattcatc gcacatttga   4560
ttaatcaaca agttgctcac gaagttcttg cgctggaaat catgattctg atgcttgaag   4620
aaccaactga tgattcagtt gaagtcgcca ttgcgttcct gaaagagtgt ggagcaaagc   4680
ttctggagat tgctccagca gctcttaaca gtgtctacga ccgtcttcgt gcaattctca   4740
tggaaactga agatcggaa aatgcactgg atcgacgtat tcagtatatg attgagactg   4800
caatgcagat tcgaaaggac aaatttgcgg taaggtagaa tatataaata gtttattaga   4860
aaaaaataaa ttagaataat ttaaattcct actagccaat caggcgacct ttttgcgcat   4920
agttctatta ttgaaaaatt tggagaattt ctcatattct cgctcggaaa tctggaattc   4980
gacgagatct tctggcttct gtgcagctgc atcgctttgt gctccctttc tcgcttgtct   5040
tctgtgtaca ccaagaacct tgttgagttc atcaactgaa tctgtgactg gcttgttgct   5100
cactggatgc actagacgac tgattctcga gaatcagat tgagttgcga ttagggtgac   5160
ctagaaattg gaataatac gaacttttga aaatattcag gaggattaaa aaattattc   5220 tcgacaatcc tacaaattta cttattgcac catgttgctc caacattttt cattaaaagt   5280
taatgaaaaa atgtagaaaa tcggaaattg gcaattttca gaccattttt aagcattttc   5340
aaaaaaaaat tgcagctgaa ataaatgtca ttttcagata aatcgagcga ttttctgttg   5400
```

```
tctgacacta gttttttagtt ttaaaaaatg ttggaagaac atggtgcaat aggtaatttc    5460
atagaatttc catgtgtttt ttttcaatta accaattatc caaatcttcc aaactcacat    5520
tttgcggagc tgggctatca agaatctgct gcagttttat aagacgagca tctctgatat    5580
cactgaaaat taatttttaa tcaaaacttg aatatcaact aaacccactt attaactttc    5640
tcgatcttct gtcgttcggt acgatgacgg tgaagaagcc aattgtagta gttgatttgg    5700
ttcaagtcct ttcggtgttg tacgtcagtg tcctgcaatg ctatttagtt ataacttagg    5760
cctaagattc aatttaatga agtgattaaa tttgttctct gaacctctta agatgatctt    5820
ttggattaga aacatataag acaggtttac ctatctatta aaaacagat caaaatagat    5880 acgaccaaat cggataatcc atgcctacct ggcatctagg aacgtgttct tagaagattt    5940
cttacgtaat cgtatgaaga ataacaatt tgatcgttgg ccagcaaaaa tagggtttta     6000
agtgggatag tgttttattt agctaaccgg aaaattttat agttttttt tgcaagaaac     6060 cactgaaaac cccctaattg tatacatttt ttggagcagc ttctggtctt tttgagcaat    6120
aaaattcgat aaaacagaat ttaagtgtaa attgttcaca tttagtttct attttatcaa    6180
attttgttgc tcaaaaacat tcgaagctgc tctaaaaaaa tgcattaaaa aagggggtttt   6240 cagtggtttt tcacattaaa aaagctaatt ttaactaaaa atccatcata tttccaactt    6300
tgtcacaaca ataaaatgct ggtcaaaatg tgttcgaaaa aatgtttttt tttttaattt    6360
ttataattta aaaatagttt tcttcgctg gacacatac attttggcc gtaaattttc       6420 agttcaaatt tccatttta caaccataat cataaagcta cgtctgatct ctctcgcact     6480
tacctgcgcc tgattcgaaa gaacaaccgt agccaaaaga acaagaagaa caagcacgta    6540
gttgtggtag tggacgttca tcacgcaata ctgaccaatg tcgtggggt ctcactttcc     6600 gtactattga gagaggggag actgaagatg gcaattgagg acagtgtctt cgacgcacgc    6660
atgcatccat aagcataatc caggagggat ggagagaaaa atcttgtttc taagcccctc    6720 ccttttgtaat acatacacat atctaatacc gaagaatggc taattgaatg gacgtcagct   6780
gttgctgtag ttgccaaggc atcatcgatg aaataactga agaaagaat taaataatta    6840 ttgcaggcgt atccggcggt cattgaagac ttggacttga ttgaggagga ggatcagatc    6900
atccatacac ttaatttgga ggatgcggtt gatccggaaa atgggcttag taagtgactg    6960
accacacgcg gggggcatta atttaataaa ttgaattcca tttcagatgt gttcaaacta    7020
gatccagaat tcgaaaagaa cgaggaggtt tatgaggaga tccgtaagga aatcattgga    7080
aacgccgata tttcggatga ggatggtggc gacgagttgg atgatgaaga agagggtagt    7140
gatgtggaag aggctccgaa gaagactaca gagattattg ataatactga tcagaattga    7200
ctgctttcag aaggtattca ttttgagttt tgggccggca aatctgtaag ttgccggttg    7260
ccgaaaattt gctgaatttg ccggaaaaaa aaattccgga atttatttaa aaactttttg    7320
taaaaattaa attaaatttg caactttca gagaagtcta cctgacaatg caatcatctt     7380
tggactacca agaagctgct cacaaaattgc tgaaaatgaa gattccagac agcatgcagg   7440
tcagcgatgt tgcaaagaaa aatttttcgac caaaaaaacc aaccaatcat aaaatttaaa   7500
aaaaaactcc gttttttttct ttttttttat acgagaaaaa ccaaaaaaat gtattttgc    7560 caaattctaa aatactatcc ccgaattttt caatattttc tctttcagaa cgaactctgc    7620
gcgatgcttg tcgattgttg tgctcaacag cgtacctacg agcgattcta cggaatgctc    7680
atcgaacgtt tctgccgact tcgcctcgaa taccagcaat acttttgaaaa gctctgccag   7740
```

```
gacacgtatt ccacgattca ccgaattgac atcacaaaac tgcggaattt ggctcgcctt      7800
attgctcatt tgctctcgac ggatgctatt gactggaaga ttttggccga tatgaaaatg      7860
accgaagagg acacaacttc ttctggcaga atctatatta aatatatatt taatgaactt      7920
gtggaggcga tgggaatggt taaacttcat tcgagagtta ctgatccgtg agtttcctag      7980
agagagttgt tttcgtattc aatttccct attttcagaa ctttggctca ttgctttgtt       8040
ggattattcc cacgaactaa tccgaacagc gcacgatttt cgatcaactt cttcacaatg      8100
attggattgg gtggtttgac gttggaactt cgtgaatggc tggcaaaggg tctcaagaag      8160
aagaagggaa tgctggatca gttgaaggcc gaatcaagct cagattcatc gtcgtcttcg      8220
gattcgtcag actcgtctga ttcttcggat tctgacgatt catccgactc gtcttcagat      8280
tcctcatctt cttcagaatc agagccagaa ccaccgaaga aaagaagaa gaagaacagt       8340 gaagagagtt ccaaaagaa ggaaaagag aatattggtc gacgggatcg tggagacaag        8400
agagctgaac gtcatcgtga tcaaagtgtg gagaacaagg acaaggatcg tcgacgtcgc      8460
caggattctg acgaaaatcg tcggccagaa cgaggagatg accgcaagga tcggagtaaa      8520
gatcgtcgtc gtcaagactc ggatgatgag gatcggaaag gtcgtgaacg tcgggaagat      8580 tcagggaaa gacgtcgcgg agatcgggat cgacgtgatc gaaacaagga tcaggaggat       8640
caccgtgaag atcgccgtga ccgaagcaag gatcgtgagg atcgacgtga tcgccgtcgt      8700
catgactctg atgatgatcg taaaactcgt cgggatagaa gtgaagagcg aggaggacgt      8760
cgtcgtgaag tggaatcgga tgatcgacgc cgacgtcgtt gaattttcaa attttaaata     8820
ctgaatattt gtttttttc ctattattta tttattctct ttgtgttttt tttcttgctt      8880
tctaaaaaat taattcaatc caaatctaaa catgagcggt ttttttttctc tttccgtctc    8940 ccaattcgta ttccgctcct ctcatctgaa cacaatgtgc aagtttattt atcttctcgc     9000
tttcatttca ttaggacgtg gggggaattg gtggaagggg gaaacacaca aaaggatgat     9060
ggaaatgaaa taaggacaca caatatgcaa caacattcaa ttcagaaata tggaggaagg     9120
tttaaaagaa aacataaaaa tatatagagg aggaaggaaa actagtaaaa aataagcaaa     9180
gaaattaggc gaacgatgag aattgtcctc gcttggcaaa tgcgaatccg tatggagagg     9240
cacgtttggc gaaggcaaat gttcggtatg gagatctgta aaaattttta agttgaaatt      9300
tggtgttgct cttttacaaa atttccgat tttcgcttga aattacggtg ccaggtctcg       9360
acacgtcttc caatttttca aattcaaaag agcctttaat gggctgtagt tgctaatttc     9420
tcgtttttga aaatttttct tccgtttaat cgaaatttga tgtatttat ttatgatttt      9480 caataaattt caaagaaact ggtgaaaact cggaaaattg tgaactacag taatccaatc     9540
cttaaaggcg cacacctttt aaatgtccgc cccaatacga tattttttta agattcgcta    9600
gagcggccgc caccgcggtg gagctccaat tcgccctata gtgagtcgta ttacaattca     9660
ctggccgtcg ttttacaacg tcgtgactgg gaaaaccctg gcgttaccca acttaatcgc     9720
cttgcagcac atccccccctt cgccagctgg cgtaatagcg aagaggcccg caccgatcgc    9780
ccttcccaac agttgcgtag cctgaatggc gaatgggacg cgccctgtag cggcgcatta     9840
agcgcggcgg gtgtggtggt tacgcgcagc gtgaccgcta cacttgccag cgccctagcg     9900
cccgctcctt tcgctttctt cccttccttt ctcgccacgt tcgccggctt tccccgtcaa     9960
gctctaaatc gggggctccc tttagggttc cgatttagtg ctttacggca cctcgacccc    10020
aaaaaacttg attagggtga tggttcacgt agtgggccat cgccctgata gacggttttt   10080
cgccctttga cgttggagtc cacgttcttt aatagtggac tcttgttcca aactggaaca    10140
```

```
acactcaacc ctatctcggt ctattctttt gatttataag ggattttgcc gatttcggcc   10200
tattggttaa aaaatgagct gatttaacaa aaatttaacg cgaattttaa caaaatatta   10260
acgtttacaa tttcaggtgg cacttttcgg ggaaatgtgc gcggaacccc tatttgttta   10320
tttttctaaa tacattcaaa tatgtatccg ctcatgagac aataaccctg ataaatgctt   10380
caataatatt gaaaaggaa gagtatgagt attcaacatt tccgtgtcgc ccttattccc   10440
ttttttgcgg cattttgcct tcctgttttt gctcacccag aaacgctggt gaaagtaaaa   10500
gatgctgaag atcagttggg tgcacgagtg ggttacatcg aactggatct caacagcggt   10560
aagatccttg agagttttcg ccccgaagaa cgttttccaa tgatgagcac ttttaaagtt   10620
ctgctatgtg gcgcggtatt atcccgtatt gacgccgggc aagagcaact cggtcgccgc   10680
atacactatt ctcagaatga cttggttgag tactcaccag tcacagaaaa gcatcttacg   10740
gatggcatga cagtaagaga attatgcagt gctgccataa catgagtga taacactgcg   10800 gccaacttac ttctgacaac gatcggagga ccgaaggagc taaccgcttt ttttcacaac   10860 atggggatc atgtaactcg ccttgatcgt tgggaaccgg agctgaatga agccatacca   10920
aacgacgagc gtgacaccac gatgcctgta gcaatggcaa caacgttgcg caaactatta   10980
actggcgaac tacttactct agcttcccgg caacaattaa tagactggat ggaggcggat   11040
aaagttgcag gaccacttct gcgctcggcc cttccggctg gctggtttat tgctgataaa   11100
tctggagccg gtgagcgtgg gtctcgcggt atcattgcag cactggggcc agatggtaag   11160
ccctcccgta tcgtagttat ctacacgacg ggcagtcagg caactatgga tgaacgaaat   11220
agacagatcg ctgagatagg tgcctcactg attaagcatt ggtaactgtc agaccaagtt   11280
tactcatata ctttagat tgatttaaaa cttcatttt aatttaaaag gatctaggtg   11340
aagatccttt tgataatct catgaccaaa atcccttaac gtgagttttc gttccactga   11400
gcgtcagacc ccgtagaaaa gatcaaagga tcttcttgag atcctttttt tctgcgcgta   11460
atctgctgct tgcaaacaaa aaaccaccg ctaccagcgg tggtttgttt gccggatcaa   11520
gagctaccaa ctcttttcc gaaggtaact ggcttcagca gagcgcagat accaaatact   11580
gtccttctag tgtagccgta gttaggccac cacttcaaga actctgtagc accgcctaca   11640
tacctcgctc tgctaatcct gttaccagtg gctgctgcca gtggcgataa gtcgtgtctt   11700
accgggttgg actcaagacg atagttaccg gataaggcgc agcggtcggg ctgaacgggg   11760
ggttcgtgca cacagcccag cttggagcga acgacctaca ccgaactgag atacctacag   11820
cgtgagcatt gagaaagcgc cacgcttccc gaagggagaa aggcggacag gtatccggta   11880
agcggcaggg tcggaacagg agagcgcacg agggagcttc cagggggaa cgcctggtat   11940 ctttatagtc ctgtcgggtt tcgccacctc tgacttgagc gtcgatttt gtgatgctcg   12000 tcagggggc cgagcctatg gaaaaacgcc agcaacgcgg cctttttacg gttcctggcc   12060
ttttgctggc cttttgctca catgttcttt cctgcgttat cccctgattc tgtggataac   12120
cgtattaccg cctttgagtg agctgatacc gctcgccgca gccgaacgac cgagcgcagc   12180
gagtcagtga gcgaggaagc ggaagagcgc ccaatacgca aaccgcctct ccccgcgcgt   12240
tggccgattc attaatgcag ctggcacgac aggtttcccg actggaaagc gggcagtgag   12300
cgcaacgcaa ttaatgtgag ttacctcact cattaggcac cccaggcttt acactttatg   12360
cttccggctc ctatgttgtg tggaattgtg agcggataac aatttcacac aggaaacagc   12420
tatgaccatg attacgccaa gctcggaatt aaccctcact aaagggaaca aaagctgggg   12480
```

-continued gg											12482

<210> SEQ ID NO 8
<211> LENGTH: 7209
<212> TYPE: DNA
<213> ORGANISM: Artificial Sequence
<220> FEATURE:
<223> OTHER INFORMATION: Description of Artificial Sequence:plasmid DNA

<400> SEQUENCE: 8

| | | | | | | |
|---|---|---|---|---|---|---|
| gatccgtcga | cagatctccc | tatagtgagt | cgtattactg | cagccaagct | aattccgggc | 60 |
| gaatttctta | tgatttatga | tttttattat | taaataagtt | ataaaaaaaa | taagtgtata | 120 |
| caaattttaa | agtgactctt | aggttttaaa | acgaaaattc | ttgttcttga | gtaactcttt | 180 |
| cctgtaggtc | aggttgcttt | ctcaggtata | gcatgaggtc | gctcttattg | accacacctc | 240 |
| taccggcatg | caagcttggc | gtaatcatgg | tcatagctgt | ttcctgtgtg | aaattgttat | 300 |
| ccgctcacaa | ttccacacaa | catacgagcc | ggaagcataa | agtgtaaagc | ctggggtgcc | 360 |
| taatgagtga | ggtaactcac | attaattgcg | ttgcgctcac | tgcccgcttt | ccagtcggga | 420 |
| aacctgtcgt | gccagctgga | ttaatgaatc | ggccaacgcg | cggggagagg | cggtttgcgt | 480 |
| attgggcgct | cttccgcttc | ctcgctcact | gactcgctgc | gctcggtcgt | tcggctgcgg | 540 |
| cgagcggtat | cagctcactc | aaaggcggta | atacggttat | ccacagaatc | aggggataac | 600 |
| gcaggaaaga | acatgtgagc | aaaaggccag | caaaaggcca | ggaaccgtaa | aaaggccgcg | 660 |
| ttgctggcgt | ttttccatag | gctccgcccc | cctgacgagc | atcacaaaaa | tcgacgctca | 720 |
| agtcagaggt | ggcgaaaccc | gacaggacta | taaagatacc | aggcgtttcc | ccctggaagc | 780 |
| tccctcgtgc | gctctcctgt | tccgaccctg | ccgcttaccg | gatacctgtc | gcctttctc | 840 |
| ccttcgggaa | gcgtggcgct | ttctcatagc | tcacgctgta | ggtatctcag | ttcggtgtag | 900 |
| gtcgttcgct | ccaagctggg | ctgtgtgcac | gaaccccccg | ttcagcccga | ccgctgcgcc | 960 |
| ttatccggta | actatcgtct | tgagtccaac | ccggtaagac | acgacttatc | gccactggca | 1020 |
| gcagccactg | gtaacaggat | tagcagagcg | aggtatgtag | gcggtgctac | agagttcttg | 1080 |
| aagtggtggc | ctaactacgg | ctacactaga | aggacagtat | ttggtatctg | cgctctgctg | 1140 |
| aagccagtta | ccttcggaaa | aagagttggt | agctcttgat | ccggcaaaca | aaccaccgct | 1200 |
| ggtagcggtg | gtttttttgt | ttgcaagcag | cagattacgc | gcagaaaaaa | aggatctcaa | 1260 |
| gaagatcctt | tgatcttttc | tacggggtct | gacgctcagt | ggaacgaaaa | ctcacgttaa | 1320 |
| gggattttgg | tcatgagatt | atcaaaaagg | atcttcacct | agatcctttt | aaattaaaaa | 1380 |
| tgaagtttta | aatcaatcta | agtatatat | gagtaaactt | ggtctgacag | ttaccaatgc | 1440 |
| ttaatcagtg | aggcacctat | ctcagcgatc | tgtctatttc | gttcatccat | agttgcctga | 1500 |
| ctccccgtcg | tgtagataac | tacgatacgg | gagggcttac | catctggccc | cagtgctgca | 1560 |
| atgataccgc | gagacccacg | ctcaccggct | ccagatttat | cagcaataaa | ccagccagcc | 1620 |
| ggaagggccg | agcgcagaag | tggtcctgca | actttatccg | cctccatcca | gtctattaat | 1680 |
| tgttgccggg | aagctagagt | aagtagttcg | ccagttaata | gtttgcgcaa | cgttgttgcc | 1740 |
| attgctacag | gcatcgtggt | gtcacgctcg | tcgtttggta | tggcttcatt | cagctccggt | 1800 |
| tcccaacgat | caaggcgagt | tacatgatcc | cccatgttgt | gcaaaaaagc | ggttagctcc | 1860 |
| ttcggtcctc | cgatcgttgt | cagaagtaag | ttggccgcag | tgttatcact | catggttatg | 1920 |
| gcagcactgc | ataattctct | tactgtcatg | ccatccgtaa | gatgcttttc | tgtgactggt | 1980 |
| gagtactcaa | ccaagtcatt | ctgagaatag | tgtatgcggc | gaccgagttg | ctcttgcccg | 2040 |

-continued

```
gcgtcaatac gggataatac cgcgccacat agcagaactt taaaagtgct catcattgga    2100
aaacgttctt cggggcgaaa actctcaagg atcttaccgc tgttgagatc cagttcgatg    2160
taacccactc gtgcacccaa ctgatcttca gcatctttta cttccaccag cgtttctggg    2220
tgagcaaaaa caggaaggca aaatgccgca aaaagggaa taagggcgac acggaaatgt     2280
tgaatactca tactcttcct ttttcaatat tattgaagca tttatcaggg ttattgtctc    2340
atgagcggat acatatttga atgtatttag aaaataaac aataggggt tccgcgcaca      2400 tttcccccgaa aagtgccacc tgaacgaagc atctgtgctt cattttgtag aacaaaaatg   2460
caacgcgaga gcgctaattt ttcaaacaaa gaatctgagc tgcattttta cagaacagaa    2520
atgcaacgcg aaagcgctat tttaccaacg aagaatctgt gcttcatttt tgtaaaacaa    2580
aaatgcaacg cgagagcgct aattttttcaa acaaagaatc tgagctgcat ttttacagaa    2640
cagaaatgca acgcgagagc gctatttttac caacaaagaa tctatacttc ttttttgttc   2700
tacaaaaatg catcccgaga gcgctatttt tctaacaaag catcttagat tactttttt    2760 ctcctttgtg cgctctataa tgcagtctct tgataacttt ttgcactgta ggtccgttaa    2820
ggttagaaga aggctacttt ggtgtctatt ttctcttcca taaaaaagc ctgactccac     2880 ttcccgcgtt tactgattac tagcgaagct gcgggtgcat ttttttcaaga taaaggcatc   2940 cccgattata ttctataccg atgtggattg cgcatacttt gtgaacagaa agtgatagcg    3000
ttgatgattc ttcattggtc agaaaattat gaacggtttc ttctattttg tctctatata    3060
ctacgtatag gaaatgttta catttttcgta ttgttttcga ttcactctat gaatagttct    3120
tactacaatt ttttgtcta aagagtaata ctagagataa acataaaaaa tgtagaggtc     3180
gagtttagat gcaagttcaa ggagcgaaag gtggatgggt aggttatata gggatatagc    3240
acagagatat atagcaaaga gatacttttg agcaatgttt gtggaagcgg tattcgcaat    3300 atttttagtag ctcgttacag tccggtgcgt ttttggtttt ttgaaagtgc gtcttcagag   3360
cgcttttggt tttcaaaagc gctctgaagt tcctatactt tctagagaat aggaacttcg    3420
gaataggaac ttcaaagcgt ttccgaaaac gagcgcttcc gaaaatgcaa cgcgagctgc    3480
gcacatacag ctcactgttc acgtcgcacc tatatctgcg tgttgcctgt atatatatat    3540
acatgagaag aacggcatag tgcgtgttta tgcttaaatg cgtacttata tgcgtctatt    3600
tatgtaggat gaaaggtagt ctagtacctc ctgtgatatt atcccattcc atgcggggta    3660
tcgtatgctt ccttcagcac tacccttag ctgttctata tgctgccact cctcaattgg     3720
attagtctca tccttcaatg ctatcatttc ctttgatatt ggatcatatt aagaaaccat    3780
tattatcatg acattaacct ataaaaatag gcgtatcacg aggccctttc gtctcgcgcg    3840
tttcggtgat gacggtgaaa acctctgaca catgcagctc ccggagacgg tcacagcttg    3900
tctgtaagcg gatgccggga gcagacaagc ccgtcagggc gcgtcagcgg tgttggcgg     3960 gtgtcgggc tggcttaact atgcggcatc agagcagatt gtactgagag tgcaccatag     4020
atcaacgaca ttactatata tataatatag gaagcattta atagacagca tcgtaatata    4080 tgtgtactt gcagttatga cgccagatgg cagtagtgga agatattctt tattgaaaaa     4140
tagcttgtca ccttacgtac aatcttgatc cggagctttt cttttttgc cgattaagaa      4200 ttaattcggt cgaaaaaaga aaggagagg gccaagaggg agggcattgg tgactattga     4260
gcacgtgagt atacgtgatt aagcacacaa aggcagcttg gagtatgtct gttattaatt    4320
tcacaggtag ttctggtcca ttggtgaaag tttgcggctt gcagagcaca gaggccgcag    4380
```

```
aatgtgctct agattccgat gctgacttgc tgggtattat atgtgtgccc aatagaaaga    4440
gaacaattga cccggttatt gcaaggaaaa tttcaagtct tgtaaaagca tataaaaata    4500
gttcaggcac tccgaaatac ttggttggcg tgtttcgtaa tcaacctaag gaggatgttt    4560
tggctctggt caatgattac ggcattgata tcgtccaact gcatggagat gagtcgtggc    4620
aagaatacca agagttcctc ggtttgccag ttattaaaag actcgtattt ccaaaagact    4680
gcaacatact actcagtgca gcttcacaga aacctcattc gtttattccc ttgtttgatt    4740
cagaagcagg tgggacaggt gaacttttgg attggaactc gatttctgac tgggttggaa    4800
ggcaagagag ccccgaaagc ttacatttta tgttagctgg tggactgacg ccagaaaatg    4860
ttggtgatgc gcttagatta aatggcgtta ttggtgttga tgtaagcgga ggtgtggaga    4920
caaatggtgt aaaagactct aacaaaatag caaatttcgt caaaaatgct aagaaatagg    4980
ttattactga gtagtattta tttaagtatt gtttgtgcac ttgccgatct atgcggtgtg    5040
aaataccgca cagatgcgta aggagaaaat accgcatcag gaaattgtaa acgttaatat    5100
tttgttaaaa ttcgcgttaa attttttgtta aatcagctca ttttttaacc aataggccga    5160
aatcggcaaa atcccttata aatcaaaaga atagaccgag atagggttga gtgttgttcc    5220
agtttggaac aagagtccac tattaaagaa cgtggactcc aacgtcaaag ggcgaaaaac    5280
cgtctatcag ggcgatggcc cactacgtga accatcaccc taatcaagtt ttttggggtc    5340
gaggtgccgt aaagcactaa atcggaaccc taaagggagc ccccgattta gagcttgacg    5400
gggaaagccg cgaacgtgg cgagaaagga agggaagaaa gcgaaaggag cgggcgctag    5460
ggcgctggca agtgtagcgg tcacgctgcg cgtaaccacc acacccgccg cgcttaatgc    5520
gccgctacag ggcgcgtcgc gccattcgcc attcaggctg cgcaactgtt gggaagggcg    5580
atcggtgcgg gcctcttcgc tattacgcca gctggcgaaa gggggatgtg ctgcaaggcg    5640
attaagttgg gtaacgccag ggttttccca gtcacgacgt tgtaaaacga cggccagtcg    5700 tccaagctt cgcgagctcg agatcccgag ctttgcaaat taaagccttc gagcgtccca    5760
aaaccttctc aagcaaggtt ttcagtataa tgttacatgc gtacacgcgt ctgtacagaa    5820 aaaaagaaa aatttgaaat ataaataacg ttcttaatac taacataact ataaaaaaat    5880
aaatagggac ctagacttca ggttgtctaa ctccttcctt ttcggttaga gcggatgtgg    5940
ggggagggcg tgaatgtaag cgtgacataa ctaattacat gatatccttt tgttgtttcc    6000
gggtgtacaa tatggacttc ctcttttctg gcaaccaaac ccatacatcg ggattcctat    6060
aataccttcg ttggtctccc taacatgtag gtggcggagg ggagatatac aatagaacag    6120
ataccagaca agacataatg ggctaaacaa gactacacca attacactgc ctcattgatg    6180
gtggtacata acgaactaat actgtagccc tagacttgat agccatcatc atatcgaagt    6240
ttcactaccc ttttttccatt tgccatctat tgaagtaata ataggcgcat gcaacttctt    6300 ttctttttt ttcttttctc tctccccgt tgttgtctca ccatatccgc aatgacaaaa    6360
aaaatgatgg aagacactaa aggaaaaaat taacgacaaa gacagcacca acagatgtcg    6420
ttgttccaga gctgatgagg ggtatcttcg aacacacgaa acttttttcct tccttcattc    6480 acgcacacta ctctctaatg agcaacggta tacggccttc cttccagtta cttgaatttg    6540
aaataaaaaa agtttgccgc tttgctatca agtataaata gacctgcaat tattaatctt    6600
ttgtttcctc gtcattgttc tcgttccctt tcttccttgt ttcttttttct gcacaatatt    6660 tcaagctata ccaagcatac aatcaactcc aagcttgaag caagcctcct gaaagatgaa    6720
gctactgtct tctatcgaac aagcatgcga tatttgccga cttaaaaagc tcaagtgctc    6780
```

```
caaagaaaaa ccgaagtgcg ccaagtgtct gaagaacaac tgggagtgtc gctactctcc      6840
caaaaccaaa aggtctccgc tgactagggc acatctgaca gaagtggaat caaggctaga      6900
aagactggaa cagctatttc tactgatttt tcctcgagaa gaccttgaca tgattttgaa      6960
aatggattct ttacaggata taaaagcatt gttaacagga ttatttgtac aagataatgt      7020
gaataaagat gccgtcacag atagattggc ttcagtggag actgtatatgc ctctaacatt      7080 gagacagcat agaataagtg cgacatcatc atcggaagag agtagtaaca aaggtcaaag      7140
acagttgact gtatcgccgg aattcttaat acgactcact agggcata tggccatgga      7200 ggccccggg                                                              7209
```

<210> SEQ ID NO 9
<211> LENGTH: 6820
<212> TYPE: DNA
<213> ORGANISM: Artificial Sequence
<220> FEATURE:
<223> OTHER INFORMATION: Description of Artificial Sequence:plasmid DNA

<400> SEQUENCE: 9

```
gatccgtcga cagatctccc tatagtgagt cgtattactg cagagatcta tgaatcgtag        60
atactgaaaa accccgcaag ttcacttcaa ctgtgcatcg tgcaccatct caatttcttt       120
catttataca tcgttttgcc ttcttttatg taactatact cctctaagtt tcaatcttgg       180
ccatgtaacc tctgatctat agaattttt aaatgactag aattaatgcc catcttttt        240 ttggacctaa attcttcatg aaaatatatt acgagggctt attcagaagc tttggacttc       300
ttcgccagag gtttggtcaa gtctccaatc aaggttgtcg gcttgtctac cttgccagaa       360
atttacgaaa agatggaaaa gggtcaaatc gttggtagat acgttgttga cacttctaaa       420
taagcgaatt tcttatgatt tatgattttt attattaaat aagttataaa aaaataagt        480 gtatacaaat tttaaagtga ctcttaggtt ttaaaacgaa aattcttgtt cttgagtaac       540
tctttcctgt aggtcaggtt gctttctcag gtatagcatg aggtcgctct tattgaccac       600
acctctaccg gcatgcccga aattccccta ccctatgaac atattccatt ttgtaatttc       660
gtgtcgtttc tattatgaat ttcatttata agtttatgt acaaatatca taaaaaaga       720 gaatcttttt aagcaaggat tttcttaact tcttcggcga cagcatcacc gacttcggtg       780
gtactgttgg aaccacctaa atcaccagtt ctgatacctg catccaaaac cttttttaact      840 gcatcttcaa tggccttacc ttcttcaggc aagttcaatg acaatttcaa catcattgca       900
gcagacaaga tagtggcgat agggtcaacc ttattctttg gcaaatctgg agcagaaccg       960
tggcatggtt cgtacaaacc aaatgcggtg ttcttgtctg gcaaagaggc caaggacgca      1020
gatggcaaca acccaagga acctgggata acggaggctt catcggagat gatatcacca      1080
aacatgttgc tggtgattat aataccattt aggtgggttg ggttcttaac taggatcatg      1140
gcggcagaat caatcaattg atgttgaacc ttcaatgtag gaaattcgtt cttgatggtt      1200
tcctccacag ttttttctcca taatcttgaa gaggccaaaa cattagcttt atccaaggac      1260
caaataggca atggtggctc atgttgtagg gccatgaaag cggccattct tgtgattctt      1320
tgcacttctg gaacggtgta ttgttcacta tcccaagcga caccatcacc atcgtcttcc      1380
tttctcttac caaagtaaat acctcccact aattctctga caacaacgaa gtcagtacct      1440
ttagcaaatt gtggcttgat tggagataag tctaaaagag agtcggatgc aaagttacat      1500
ggtcttaagt tggcgtacaa ttgaagttct ttacggattt ttagtaaacc ttgttcaggt      1560
```

```
ctaacactac ctgtacccca tttaggacca cccacagcac ctaacaaaac ggcatcaacc      1620
ttcttggagg cttccagcgc ctcatctgga agtgggacac ctgtagcatc gatagcagca      1680
ccaccaatta aatgattttc gaaatcgaac ttgacattgg aacgaacatc agaaatagct      1740
ttaagaacct taatggcttc ggctgtgatt tcttgaccaa cgtggtcacc tggcaaaacg      1800
acgatcttct tagggggcaga cattagaatg gtatatcctt gaaatatata tatatattgc     1860
tgaaatgtaa aaggtaagaa aagttagaaa gtaagacgat tgctaaccac ctattggaaa     1920
aaacaatagg tccttaaata atattgtcaa cttcaagtat tgtgatgcaa gcatttagtc     1980
atgaacgctt ctctattcta tatgaaaagc cggttccggc ctctcacctt tcctttttct     2040
cccaattttt cagttgaaaa aggtatatgc gtcaggcgac ctctgaaatt aacaaaaaat     2100
ttccagtcat cgaatttgat tctgtgcgat agcgccctg tgtgttctcg ttatgttgag      2160
gaaaaaaata atggttgcta agagattcga actcttgcat cttacgatac ctgagtattc      2220
ccacagttgg ggatctcgac tctagctaga ggatcaattc gtaatcatgg tcatagctgt      2280
ttcctgtgtg aaattgttat ccgctcacaa ttccacacaa catacgagcc ggaagcataa     2340
agtgtaaagc ctggggtgcc taatgagtga ggtaactcac attaattgcg ttgcgctcac      2400
tgcccgcttt ccagtcggga aacctgtcgt gccagctgga ttaatgaatc ggccaacgcg     2460
cggggagagg cggtttgcgt attgggcgct cttccgcttc ctcgctcact gactcgctgc      2520
gctcggtcgt tcggctgcgg cgagcggtat cagctcactc aaaggcggta atacggttat      2580
ccacagaatc aggggataac gcaggaaaga acatgtgagc aaaaggccag caaaaggcca      2640
ggaaccgtaa aaaggccgcg ttgctggcgt ttttccatag gctccgcccc cctgacgagc     2700
atcacaaaaa tcgacgctca agtcagaggt ggcgaaaccc gacaggacta taaagatacc     2760
aggcgtttcc ccctggaagc tccctcgtgc gctctcctgt tccgaccctg ccgcttaccg     2820
gatacctgtc cgcctttctc ccttcgggaa gcgtggcgct ttctcatagc tcacgctgta     2880
ggtatctcag ttcggtgtag gtcgttcgct ccaagctggg ctgtgtgcac gaacccccg      2940 ttcagcccga ccgctgcgcc ttatccggta actatcgtct tgagtccaac ccggtaagac     3000
acgacttatc gccactggca gcagccactg gtaacaggat tagcagagcg aggtatgtag     3060
gcggtgctac agagttcttg aagtggtggc ctaactacgg ctacactaga aggacagtat     3120
ttggtatctg cgctctgctg aagccagtta ccttcggaaa aagagttggt agctcttgat     3180
ccggcaaaca aaccaccgct ggtagcggtg gtttttttgt ttgcaagcag cagattacgc     3240
gcagaaaaaa aggatctcaa gaagatcctt tgatcttttc tacggggtct gacgctcagt     3300
ggaacgaaaa ctcacgttaa gggattttgg tcatgagatt atcaaaaagg atcttcacct     3360
agatcctttt aaattaaaaa tgaagtttta aatcaatcta agtatatat gagtaaactt      3420 ggtctgacag ttaccaatgc ttaatcagtg aggcacctat ctcagcgatc tgtctatttc      3480
gttcatccat agttgcctga ctccccgtcg tgtagataac tacgatacgg gagggcttac     3540
catctggccc cagtgctgca atgataccgc gagacccacg ctcaccggct ccagatttat     3600
cagcaataaa ccagccagcc ggaagggccg agcgcagaag tggtcctgca actttatccg     3660
cctccatcca gtctattaat tgttgccggg aagctagagt aagtagttcg ccagttaata     3720
gtttgcgcaa cgttgttgcc attgctacag gcatcgtggt gtcacgctcg tcgtttggta     3780
tggcttcatt cagctccggt tcccaacgat caaggcgagt tacatgatcc cccatgttgt     3840
gcaaaaaagc ggttagctcc ttcggtcctc cgatcgttgt cagaagtaag ttggccgcag     3900
tgttatcact catggttatg gcagcactgc ataattctct tactgtcatg ccatccgtaa     3960
```

```
gatgcttttc tgtgactggt gagtactcaa ccaagtcatt ctgagaatag tgtatgcggc    4020
gaccgagttg ctcttgcccg cgtcaatac gggataatac cgcgccacat agcagaactt    4080
taaaagtgct catcattgga aaacgttctt cggggcgaaa actctcaagg atcttaccgc    4140
tgttgagatc cagttcgatg taacccactc gtgcacccaa ctgatcttca gcatctttta    4200
ctttcaccag cgtttctggg tgagcaaaaa caggaaggca aaatgccgca aaaagggaa    4260 taagggcgac acggaaatgt tgaatactca tactcttcct ttttcaatat tattgaagca    4320
tttatcaggg ttattgtctc atgagcggat acatatttga atgtatttag aaaaataaac    4380 aaatagggt tccgcgcaca tttccccgaa aagtgccacc tgacgtctaa gaaaccatta    4440
ttatcatgac attaacctat aaaaataggc gtatcacgag gcccttccgt ctcgcgcgtt    4500
tcggtgatga cggtgaaaac ctctgacaca tgcagctccc ggagacggtc acagcttgtc    4560
tgtaagcgga tgccgggagc agacaagccc gtcagggcgc gtcagcgggt gttggcgggt    4620 gtcgggctg gcttaactat gcggcatcag agcagattgt actgagagtg caccataacg    4680
catttaagca taaacacgca ctatgccgtt cttctcatgt atatatatat acaggcaaca    4740
cgcagatata ggtgcgacgt gaacagtgag ctgtatgtgc gcagctcgcg ttgcattttc    4800
ggaagcgctc gttttcggaa acgctttgaa gttcctattc cgaagttcct attctctagc    4860
tagaaagtat aggaacttca gagcgctttt gaaaaccaaa agcgctctga agacgcactt    4920
tcaaaaaacc aaaaacgcac cggactgtaa cgagctacta aaatattgcg aataccgctt    4980
ccacaaacat tgctcaaaag tatctctttg ctatatatct ctgtgctata tccctatata    5040
acctacccat ccacctttcg ctccttgaac ttgcatctaa actcgacctc tacatttttt    5100
atgtttatct ctagtattac tctttagaca aaaaattgt agtaagaact attcatagag    5160
tgaatcgaaa acaatacgaa aatgtaaaca tttcctatac gtagtatata gagacaaaat    5220
agaagaaacc gttcataatt ttctgaccaa tgaagaatca tcaacgctat cactttctgt    5280
tcacaaagta tgcgcaatcc acatcggtat agaatataat cggggatgcc tttatcttga    5340
aaaaatgcac ccgcagcttc gctagtaatc agtaaacgcg ggaagtggag tcaggctttt    5400
tttatggaag agaaaataga caccaaagta gccttcttct aaccttaacg gacctacagt    5460
gcaaaaagtt atcaagagac tgcattatag agcgcacaaa ggagaaaaaa agtaatctaa    5520
gatgctttgt tagaaaaata gcgctctcgg gatgcatttt tgtagaacaa aaagaagta    5580 tagattcttc gttggtaaaa tagcgctctc gcgttgcatt tctgttctgt aaaaatgcag    5640
ctcagattct ttgtttgaaa aattagcgct ctcgcgttgc attttttgttt tacaaaaatg    5700 aagcacagat tcttcgttgg taaaatagcg ctttcgcgtt gcatttctgt tctgtaaaaa    5760
tgcagctcag attctttgtt tgaaaaatta gcgctctcgc gttgcatttt tgttctacaa    5820
aatgaagcac agatgcttcg ttgcttgcat gcaacttctt ttcttttttt ttcttttctc    5880 tctccccgt tgttgtctca ccatatccgc aatgacaaaa aaatgatgg aagacactaa    5940 aggaaaaaat taacgacaaa gacagcacca acagatgtcg ttgttccaga gctgatgagg    6000
ggtatcttcg aacacacgaa acttttcct tccttcattc acgcacacta ctctctaatg    6060
agcaacggta tacggccttc cttccagtta cttgaatttg aaataaaaaa agtttgccgc    6120
tttgctatca agtataaata gacctgcaat tattaatctt ttgtttcctc gtcattgttc    6180
tcgttccctt tcttccttgt ttctttttct gcacaatatt tcaagctata ccaagcatac    6240
aatcaactcc aagcttgca aagatggata agcggaatt aattcccgag cctccaaaaa    6300
```

| | | | | |
|---|---|---|---|---|
| agaagagaaa | ggtcgaattg | ggtaccgccg | ccaattttaa | tcaaagtggg aatattgctg | 6360 |
| atagctcatt | gtccttcact | ttcactaaca | gtagcaacgg | tccgaacctc ataacaactc | 6420 |
| aaacaaattc | tcaagcgctt | tcacaaccaa | ttgcctcctc | taacgttcat gataacttca | 6480 |
| tgaataatga | aatcacggct | agtaaaattg | atgatggtaa | taattcaaaa ccactgtcac | 6540 |
| ctggttggac | ggaccaaact | gcgtataacg | cgtttggaat | cactacaggg atgtttaata | 6600 |
| ccactacaat | ggatgatgta | tataactatc | tattcgatga | tgaagatacc ccaccaaacc | 6660 |
| caaaaaaga | gatcgaattc | ttaatacgac | tcactatagg | gcccatggac gaagaatcca | 6720 |
| gttcattctt | atgtacctat | gctgagaatc | gtgccaataa | gaagccaata cttccttaga | 6780 |
| tgatgcaata | aatattaaaa | taaaacaaaa | cagaaggctg | | 6820 |

<210> SEQ ID NO 10
<211> LENGTH: 10597
<212> TYPE: DNA
<213> ORGANISM: Artificial Sequence
<220> FEATURE:
<223> OTHER INFORMATION: Description of Artificial Sequence:plasmid DNA

<400> SEQUENCE: 10

| | | | | |
|---|---|---|---|---|
| ccggtggtac | cgggcccccc | ctcgaggtcg | acggtatcga | taagctttcg tcattgaaaa | 60 |
| gaaggataag | aatggacgat | gggaagaagc | tctcgttgtt | ccaggagatc agaaaacagc | 120 |
| aactgttcca | aatcttaagg | agggagaaga | atatcaattc | agaatttctg ctcgtaacaa | 180 |
| ggctggaact | ggagatcctt | ctgatccttc | tgatcgtgtt | gttgcgaagc caagaaacct | 240 |
| tgctccaaga | attcatcgtg | aagatctttc | tgatacaact | gtcaaggtcg agccactct | 300 |
| caagttcatt | gttcatattg | atggtgagcc | agcaccagat | gtaacatggt cattcaatgg | 360 |
| aaaaggaatc | ggagagagca | aggctcaaat | tgaaaatgag | ccatacatct cgagatttgc | 420 |
| tttgccaaag | gcacttcgta | agcaaagtgg | aaaatatacc | atcactgcaa ccaacattaa | 480 |
| tggaactgac | agtgtcacta | tcaatatcaa | ggtaaaaagc | aagccaacga accaaagggg | 540 |
| accaatcgag | gtaactgatg | tcttcgaaga | tcgtgcaact | cttgactgga accaccaga | 600 |
| ggatgacgga | ggagagccaa | ttgagttcta | tgaaattgaa | aagatgaaca ccaaggacgg | 660 |
| aatctgggtt | ccatgtggac | gtagtggaga | tacccacttc | acagtcgatt cactcaacaa | 720 |
| gggagatcat | tacaagttcc | gtgtcaaggc | tgtcaacagc | gaaggacctt ctgatccatt | 780 |
| ggaaactgaa | accgatattt | tggctaaaaa | tccatttgat | cgtccagata gaccaggtcg | 840 |
| tccagagcca | actgattggg | attctgatca | tgttgatctc | aagtgggatc cactagttct | 900 |
| agaagcgctg | ctaaggggc | cctcgtcgag | tcggtcacaa | tcacctgaaa ctccaaaggc | 960 |
| agccagtgag | gaacgtgaag | aagaagaaaa | agagtcatct | gaacaggttt gattttcttt | 1020 |
| ctggtcaaaa | agatgaaatt | attgattttc | agccagatac | tcccaaaact agcagcgaga | 1080 |
| agtctgcaag | tcgttcacag | tcgcccagag | aatcgcggga | agtgagccaa gaggtatgtt | 1140 |
| tttcaaaaat | caataactga | tcataatttt | tattgtttgg | tgaatttaag aaaataatat | 1200 |
| tcgaaaattc | ctctgaatta | tcaagattgc | agtattaatt | tcgagaaaaa ttgagatatt | 1260 |
| catagagcta | ttgtaaattt | tcttgatttc | agactgaaac | ttcggaaaat caagagaaaa | 1320 |
| tcaaagaaaa | ggatgacggg | gatgatcagc | tggcacacc | gaacagctat agaagccggg | 1380 |
| aaacttcacc | agctccaaaa | aggtccaagg | agaccaggtt | tgtcaaaagc ttcctgcgat | 1440 |
| taattctcat | ttcaattttt | cagagaatca | gagtctcctg | aaaaatcccc ggttcgttca | 1500 |
| agatctccca | gaaggtcttc | agcacgttcc | ccgtcacgat | ctcctagacg gcgccgagaa | 1560 |

```
agaagctcag aaagaaagca atccgaagag ccagcaccgc taccagagaa aaagaagaaa  1620
gagccgctgg atattctacg aacaagaacc ggaggagcat atattccacc cgccaaactt  1680
cgacttatgc aacaacagat tagtgataag caaagtgaac agtatcagag aatgaattgg  1740
gaaagaatga agaaaaagat tcacggattg gttaacagag tcaacgcgaa gaatcttgtt  1800
caaattgtca gagaacttct tcaagagaat gtgattcgtt caaagtgagt gagaaaatcg  1860
aaggaaaagg aaagaattaa tttaattttt cagggggactt ctctgccgtg acattattca  1920
agctcaggct ttctcaccag gattctctaa cgtctatgca gctttggcgg cagttatcaa  1980
ctcgaaattc cctcatgtcg gtgaacttct tctccgtcgt ctgattgtac agttcaaaag  2040
aagtttccgt agaaatgaca gaggcgtcac ggtgaacgtg atcaaattca tcgcacattt  2100
gattaatcaa caagttgctc acgaagttct tgcgctggaa atcatgattc tgatgcttga  2160
agaaccaact gatgattcag ttgaagtcgc cattgcgttc ctgaaagagt gtggagcaaa  2220
gcttctggag attgctccag cagctcttaa cagtgtctac gaccgtcttc gtgcaattct  2280
catgaaaact gaaagatcgg aaaatgcact ggatcgacgt attcagtata tgattgagac  2340
tgcaatgcag attcgaaagg acaaatttgc ggtaaggtag aatatataaa tagtttatta  2400
gaaaaaaata aattagaata atttaaattc ctactagcca atcaggcgac cttttttgcgc  2460
atagttctat tattgaaaaa tttggagaat ttctcatatt ctcgctcgga aatctggaat  2520
tcgacgagat cttctggctt ctgtgcagct gcatcgcttt gtgctccctt tctcgcttgt  2580
cttctgtgta caccaagaac cttgttgagt tcatcaactg aatctgtgac tggcttgttg  2640
ctcactggat gcactagacg actgattctc gagaaatcag attgagttgc gattagggtg  2700
acctagaaat tgggaataat acgaactttt gaaaatattc aggaggatta aaaaaattat  2760
tctcgacaat cctacaaatt tacttattgc accatgttgc tccaacattt ttcattaaaa  2820
gttaatgaaa aaatgtagaa aatcggaaat tggcaatttt cagaccattt ttaagcattt  2880
tcaaaaaaaa attgcagctg aaataaatgt cattttcaga taaatcgagc gattttctgt  2940
tgtctgacac tagtttttag ttttaaaaaa tgttggaaga acatggtgca ataggtaatt  3000
tcatagaatt tccatgtgtt ttttttcaat taaccaatta tccaaatctt ccaaactcac  3060
attttgcgga gctgggctat caagaatctg ctgcagtttt ataagacgag catctctgat  3120
atcactgaaa attaattttt aatcaaaact tgaatatcaa ctaaacccac ttattaactt  3180
tctcgatctt ctgtcgttcg gtacgatgac ggtgaagaag ccaattgtag tagttgattt  3240
ggttcaagtc ctttcggtgt tgtacgtcag tgtcctgcaa tgctatttag ttataactta  3300
ggcctaagat tcaatttaat gaagtgatta aatttgttct ctgaacctct taagatgatc  3360
ttttggatta gaaacatata agacaggttt acctatctat taaaaaacag atcaaaatag  3420
atacgaccaa atcggataat ccatgcctac ctggcatcta ggaacgtgtt cttagaagat  3480
ttcttacgta atcgtatgaa gaaataacaa tttgatcgtt ggccagcaaa aataagggtttt  3540
taagtgggat agtgttttta ttagctaacc ggaaaatttt atagtttttt tttgcaagaa  3600
accactgaaa acccctaat tgtatacatt ttttggagca gcttctggtc tttttgagca  3660
ataaaattcg ataaaacaga atttaagtgt aaattgttca catttagttt ctattttatc  3720
aaattttgtt gctcaaaaac attcgaagct gctctaaaaa aatgcattaa aaaagggggtt  3780
ttcagtggtt tttcacatta aaaaagctaa ttttaactaa aaatccatca tatttccaac  3840
tttgtcacaa caataaaatg ctggtcaaaa tgtgttcgaa aaaatgtttt tttttttaat  3900
```

```
tttatataatt taaaaatagt tttctttcgc tgggacacat acattttggg gcgtaaattt    3960
tcagttcaaa ttttccatttt tacaaccata atcataaagc tacgtctgat ctctctcgca    4020
cttacctgcg cctgattcga aagaacaacc gtagccaaaa gaacaagaag aacaagcacg    4080
tagttgtggt agtggacgtt catcacgcaa tactgaccaa tggtcgtggg gtctcacttt    4140
ccgtactatt gagagagggg agactgaaga tggcaattga ggacagtgtc ttcgacgcac    4200
gcatgcatcc ataagcataa tccaggaggg atggagagaa aaatcttgtt tctaagcccc    4260 tcccttttgta atacatacac atatctaata ccgaagaatg gctaattgaa tggacgtcag    4320
ctgttgctgt agttgccaag gcatcatcga tgaaataact gaaagaaaga attaaataat    4380
tattgcaggc gtatccggcg gtcattgaag acttggactt gattgaggag gaggatcaga    4440
tcatccatac acttaatttg gaggatgcgg ttgatccgga aaatgggctt agtaagtgac    4500
tgaccacacg cgggggggcat taatttaata aattgaattc catttcagat gtgttcaaac    4560
tagatccaga attcgaaaag aacgaggagg tttatgagga gatccgtaag gaaatcattg    4620
gaaacgccga tatttcggat gaggatggtg gcgacgagtt ggatgatgaa gaagagggta    4680
gtgatgtgga agaggctccg aagaagacta cagagattat tgataatact gatcagaatt    4740
gactgctttc agaaggtatt cattttgagt tttgggccgg caaatctgta agttgccggt    4800
tgccgaaaat ttgctgaatt tgccggaaaa aaaaattccg gaatttattt aaaaacttt    4860 tgtaaaaatt aaattaaatt tgcaactttt cagagaagtc tacctgacaa tgcaatcatc    4920
tttggactac caagaagctg ctcacaaatt gctgaaaatg aagattccag acagcatgca    4980
ggtcagcgat gttgcaaaga aaaattttcg accaaaaaaa ccaaccaatc ataaaattta    5040
aaaaaaaact ccgttttttt cttttttttt atacgagaaa aaccaaaaaa atgtatttt    5100 gccaaattct aaaatactat ccccgaaatt ttcaatattt tctctttcag aacgaactct    5160
gcgcgatgct tgtcgattgt tgtgctcaac agcgtaccta cgagcgattc tacgaatgc    5220 tcatcgaacg tttctgccga cttcgcctcg aataccagca atactttgaa aagctctgcc    5280
aggacacgta ttccacgatt caccgaattg acatcacaaa actgcggaat ttggctcgcc    5340
ttattgctca tttgctctcg acggatgcta ttgactggaa gattttggcc gatatgaaaa    5400
tgaccgaaga ggacacaact tcttctggca gaatctatat taaatatata tttaatgaac    5460
ttgtggaggc gatgggaatg gttaaacttc attcgagagt tactgatccg tgagtttcct    5520
agagagagtt gttttcgtat tcaatttttcc ctattttcag aactttggct cattgctttg    5580
ttggattatt cccacgaact aatccgaaca gcgcacgatt ttcgatcaac ttcttcacaa    5640
tgattggatt gggtggtttg acgttggaac ttcgtgaatg gctggcaaag ggtctcaaga    5700
agaagaaggg aatgctggat cagttgaagg ccgaatcaag ctcagattca tcgtcgtctt    5760
cggattcgtc agactcgtct gattcttcgg attctgacga ttcatccgac tcgtcttcag    5820
attcctcatc ttcttcagaa tcagagccag aaccaccgaa gaaaagaag aagaagaaca    5880 gtgaagagag ttccaaaaag aaggaaaaag agaatattgg tcgacgggat cgtggagaca    5940
agagagctga acgtcatcgt gatcaaagtg tggagaacaa ggacaaggat cgtcgacgtc    6000
gccaggattc tgacgaaaat cgtcggccag aacgaggaga tgaccgcaag gatcggagta    6060
aagatcgtcg tcgtcaagac tcggatgatg aggatcggaa aggtcgtgaa cgtcgggaag    6120
attcagggga aagacgtcgc ggagatcggg atcgacgtga tcgaaacaag gatcaggagg    6180
atcaccgtga agatcgccgt gaccgaagca aggatcgtga ggatcgacgt gatcgccgtc    6240
gtcatgactc tgatgatgat cgtaaaactc gtcgggatag aagtgaagag cgaggaggac    6300
```

```
gtcgtcgtga agtggaatcg gatgatcgac gccgacgtcg ttgaattttc aaattttaaa    6360
tactgaatat ttgtttttt tcctattatt tatttattct ctttgtgttt tttttcttgc     6420
tttctaaaaa attaattcaa tccaaatcta aacatgagcg gttttttttc tctttccgtc    6480
tcccaattcg tattccgctc ctctcatctg aacacaatgt gcaagtttat ttatcttctc    6540
gctttcattt cattaggacg tgggggaat tggtggaagg gggaaacaca caaaggatg      6600 atggaaatga ataaggaca cacaatatgc aacaacattc aattcagaaa tatggaggaa     6660
ggtttaaaag aaaacataaa aatatataga ggaggaagga aaactagtaa aaaataagca    6720
aagaaattag gcgaacgatg agaattgtcc tcgcttggca aatgcgaatc cgtatggaga    6780
ggcacgtttg gcgaaggcaa atgttcggta tggagatctg taaaaatttt taagttgaaa    6840
tttggtgttg ctcttttaca aaattttccg attttcgctt gaaattacgg tgccaggtct    6900
cgacacgtct tccaattttt caaattcaaa agagcctta atgggctgta gttgctaatt     6960
tctcgttttt gaaaattttt cttccgttta atcgaaattt gatgtatttt atttatgatt    7020
ttcaataaat ttcaaagaaa ctggtgaaaa ctcggaaaat tgtgaactac agtaatccaa    7080
tccttaaagg cgcacacctt ttaaatgtcc gccccaatac gatattttt taagattcgc     7140 tagagcggcc gccaccgcgg tggagctcca attcgcccta tagtgagtcg tattacaatt    7200
cactggccgt cgttttacaa cgtcgtgact gggaaaaccc tggcgttacc caacttaatc    7260
gccttgcagc acatccccc ttcgccagct ggcgtaatag cgaagaggcc cgcaccgatc     7320
gcccttccca acagttgcgt agcctgaatg gcgaatggga cgcgccctgt agcggcgcat    7380
taagcgcggc gggtgtggtg gttacgcgca gcgtgaccgc tacacttgcc agcgccctag    7440
cgcccgctcc tttcgctttc ttcccttcct ttctcgccac gttcgccggc tttccccgtc    7500
aagctctaaa tcggggctc cctttagggt tccgatttag tgctttacgg cacctcgacc    7560
ccaaaaaact tgattagggt gatggttcac gtagtgggcc atcgccctga tagacggttt    7620
ttcgcccttt gacgttggag tccacgttct ttaatagtgg actcttgttc caaactggaa    7680
caacactcaa ccctatctcg gtctattctt ttgatttata agggattttg ccgatttcgg    7740
cctattggtt aaaaatgag ctgatttaac aaaaatttaa cgcgaatttt aacaaaatat     7800
taacgtttac aatttcaggt ggcacttttc ggggaaatgt gcgcggaacc cctatttgtt    7860
tatttttcta aatacattca aatatgtatc cgctcatgag acaataaccc tgataaatgc    7920
ttcaataata ttgaaaaagg aagagtatga gtattcaaca tttccgtgtc gcccttattc    7980
ccttttttgc ggcattttgc cttcctgttt ttgctcaccc agaaacgctg gtgaaagtaa    8040
aagatgctga agatcagttg ggtgcacgag tgggttacat cgaactggat ctcaacagcg    8100
gtaagatcct tgagagtttt cgccccgaag aacgttttcc aatgatgagc acttttaaag    8160
ttctgctatg tggcgcggta ttatcccgta ttgacgccgg gcaagagcaa ctcggtcgcc    8220
gcatacacta ttctcagaat gacttggttg agtactcacc agtcacagaa aagcatctta    8280
cggatggcat gacagtaaga gaattatgca gtgctgccat aagcatgagt gataacactg    8340
cggccaactt acttctgaca acgatcggag gaccgaagga gctaaccgct ttttttcaca    8400
acatggggga tcatgtaact cgccttgatc gttgggaacc ggagctgaat gaagccatac    8460
caaacgacga gcgtgacacc acgatgcctg tagcaatggc aacaacgttg cgcaaactat    8520
taactggcga actacttact ctagcttccc ggcaacaatt aatagactgg atggaggcgg    8580
ataaagttgc aggaccactt ctgcgctcgg cccttccggc tggctggttt attgctgata    8640
```

```
aatctggagc cggtgagcgt gggtctcgcg gtatcattgc agcactgggg ccagatggta    8700
agccctcccg tatcgtagtt atctacacga cgggcagtca ggcaactatg gatgaacgaa    8760
atagacagat cgctgagata ggtgcctcac tgattaagca ttggtaactg tcagaccaag    8820
tttactcata tatactttag attgatttaa aacttcattt ttaatttaaa aggatctagg    8880
tgaagatcct ttttgataat ctcatgacca aaatccctta acgtgagttt cgttccact    8940 gagcgtcaga ccccgtagaa aagatcaaag gatcttcttg agatcctttt tttctgcgcg    9000
taatctgctg cttgcaaaca aaaaaaccac cgctaccagc ggtggtttgt ttgccggatc    9060
aagagctacc aactctttt ccgaaggtaa ctggcttcag cagagcgcag ataccaaata    9120
ctgtccttct agtgtagccg tagttaggcc accacttcaa gaactctgta gcaccgccta    9180
catacctcgc tctgctaatc ctgttaccag tggctgctgc cagtggcgat aagtcgtgtc    9240
ttaccgggtt ggactcaaga cgatagttac cggataaggc gcagcggtcg ggctgaacgg    9300
ggggttcgtg cacacagccc agcttggagc gaacgaccta caccgaactg agatacctac    9360
agcgtgagca ttgagaaagc gccacgcttc ccgaagggag aaaggcggac aggtatccgg    9420
taagcggcag ggtcggaaca ggagagcgca cgagggagct tccagggggg aacgcctggt    9480
atctttatag tcctgtcggg tttcgccacc tctgacttga gcgtcgattt ttgtgatgct    9540
cgtcaggggg gccgagccta tggaaaaacg ccagcaacgc ggccttttta cggttcctgg    9600
ccttttgctg gccttttgct cacatgttct ttcctgcgtt atcccctgat tctgtggata    9660
accgtattac cgcctttgag tgagctgata ccgctcgccg cagccgaacg accgagcgca    9720
gcgagtcagt gagcgaggaa gcggaagagc gcccaatacg caaaccgcct ctccccgcgc    9780
gttggccgat tcattaatgc agctggcacg acaggtttcc cgactggaaa gcgggcagtg    9840
agcgcaacgc aattaatgtg agttacctca ctcattaggc accccaggct ttacacttta    9900
tgcttccggc tcctatgttg tgtggaattg tgagcggata acaatttcac acaggaaaca    9960
gctatgacca tgattacgcc aagctcggaa ttaaccctca ctaaagggaa caaaagctgg    10020 ggggatcct ccaaaatcgt cttccgctct gaaaaacgaa agtggacctt tgacatccga    10080
aaaaatgggc gaaaaaatga aattgagctt tttgggtcga aaaaaatgtt tttagaatgc    10140
tgagaacacg ttaaacacga agatcatatt tattttgaga cccggatgct ctgaaaatgt    10200
ctgacataga tttaaaaaag catatatata tttttcattt tcaacgtgaa agttttgtgc    10260
aactttatag aatctcctat tggcacattg tttttttatt tt aactgaggca gtttttgaac    10320 accttttga aactttgaat ctctttgaag tatactgtcg aaaagactga cttgagcgtt    10380
cgaaatgcca gaagaaaact atatttgaat ctcgcgctaa attgagaaat gcaaccgcgc    10440
tccactggac aattggaaaa aaatttatt cggaggcgac aacggtattt tcgaaattga    10500
ttttctgtgt atttttctcat tttttataaa ttcttctttg atttatcgtt cgtttgtgag    10560
aaatttaatt gtattcaaac tttttttatag taagata                           10597
```

<210> SEQ ID NO 11
<211> LENGTH: 10599
<212> TYPE: DNA
<213> ORGANISM: Artificial Sequence
<220> FEATURE:
<223> OTHER INFORMATION: Description of Artificial Sequence:plasmid DNA

<400> SEQUENCE: 11

```
ccggtggtac cgctagccgt acgaacccgg gttctagaac tagtggatcc cacttgagat    60
caacatgatc agaatcccaa tcagttggct ctggacgacc tggtctatct ggacgatcaa    120
```

-continued

```
atggattttt agccaaaata tcggtttcag tttccaatgg atcagaaggt ccttcgctgt      180
tgacagcctt gacacggaac ttgtaatgat ctcccttgtt gagtgaatcg actgtgaagt      240
gggtatctcc actacgtcca catggaaccc agattccgtc cttggtgttc atcttttcaa      300
tttcatagaa ctcaattggc tctcctccgt catcctctgg tggtttccag tcaagagttg      360
cacgatcttc gaagacatca gttacctcga ttggtccctt tggtttcgtt ggcttgcttt      420
ttaccttgat attgatagtg acactgtcag ttccattaat gttggttgca gtgatggtat      480
attttccact tgcttacga agtgcctttg caaagcaaa tctcgagatg tatggctcat      540
tttcaatttg agccttgctc tctccgattc cttttccatt gaatgaccat gttacatctg      600
gtgctggctc accatcaata tgaacaatga acttgagagt ggctccgacc ttgacagttg      660
tatcagaaag atcttcacga tgaattcttg gagcaaggtt tcttggcttc gcaacaacac      720
gatcagaagg atcagaagga tctccagttc cagccttgtt acgagcagaa attctgaatt      780
gatattcttc tccctcctta agatttggaa cagttgctgt tttctgatct cctggaacaa      840
cgagagcttc ttcccatcgt ccattcttat ccttcttttc aatgacgaaa gcttatcgat      900
accgtcgacc tcgaggggg gccctcgtcg agtcggtcac aatcacctga aactccaaag      960
gcagccagtg aggaacgtga agaagaagaa aaagagtcat ctgaacaggt ttgattttct      1020
ttctggtcaa aaagatgaaa ttattgattt tcagccagat actcccaaaa ctagcagcga      1080
gaagtctgca agtcgttcac agtcgcccag agaatcgcgg gaagtgagcc aagaggtatg      1140
tttttcaaaa atcaataact gatcataatt tttattgttt ggtgaattta agaaaataat      1200
attcgaaaat tcctctgaat tatcaagatt gcagtattaa tttcgagaaa aattgagata      1260 tcatagagc tattgtaaat tttcttgatt tcagactgaa acttcggaaa atcaagagaa      1320
aatcaaagaa aaggatgacg gggatgatca gcctggcaca ccgaacagct atagaagccg      1380
ggaaacttca ccagctccaa aaaggtccaa ggagaccagg tttgtcaaaa gcttcctgcg      1440
attaattctc atttcaattt ttcagagaat cagagtctcc tgaaaaatcc ccggttcgtt      1500
caagatctcc cagaaggtct tcagcacgtt ccccgtcacg atctcctaga cggcgccgag      1560
aaagaagctc agaaagaaag caatccgaag agccagcacc gctaccagag aaaaagaaga      1620
aagagccgct ggatattcta cgaacaagaa ccggaggagc atatattcca cccgccaaac      1680
ttcgacttat gcaacaacag attagtgata agcaaagtga acagtatcag agaatgaatt      1740
gggaaagaat gaagaaaaag attcacggat tggttaacag agtcaacgcg aagaatcttg      1800
ttcaaattgt cagagaactt cttcaagaga atgtgattcg ttcaaagtga gtgagaaaat      1860
cgaaggaaaa ggaaagaatt aatttaattt ttcaggggac ttctctgccg tgacattatt      1920
caagctcagg ctttctcacc aggattctct aacgtctatg cagctttggc ggcagttatc      1980
aactcgaaat tccctcatgt cggtgaactt cttctccgtc gtctgattgt acagttcaaa      2040
agaagtttcc gtagaaatga cagaggcgtc acggtgaacg tgatcaaatt catcgcacat      2100
ttgattaatc aacaagttgc tcacgaagtt cttgcgctgg aaatcatgat tctgatgctt      2160
gaagaaccaa ctgatgattc agttgaagtc gccattgcgt tcctgaaaga gtgtggagca      2220
aagcttctgg agattgctcc agcagctctt aacagtgtct acgaccgtct tcgtgcaatt      2280
ctcatggaaa ctgaaagatc ggaaaatgca ctggatcgac gtattcagta tatgattgag      2340
actgcaatgc agattcgaaa ggacaaattt gcggtaaggt agaatatata aatagtttat      2400
tagaaaaaaa taaattagaa taatttaaat tcctactagc caatcaggcg acctttttgc      2460
```

-continued

```
gcatagttct attattgaaa aatttggaga atttctcata ttctcgctcg gaaatctgga    2520
attcgacgag atcttctggc ttctgtgcag ctgcatcgct ttgtgctccc tttctcgctt    2580
gtcttctgtg tacaccaaga accttgttga gttcatcaac tgaatctgtg actggcttgt    2640
tgctcactgg atgcactaga cgactgattc tcgagaaatc agattgagtt gcgattaggg    2700
tgacctagaa attgggaata atacgaactt tgaaaatat tcaggaggat taaaaaaatt     2760
attctcgaca atcctacaaa tttacttatt gcaccatgtt gctccaacat ttttcattaa    2820
aagttaatga aaaaatgtag aaaatcggaa attggcaatt ttcagaccat ttttaagcat    2880
tttcaaaaaa aaattgcagc tgaaataaat gtcattttca gataaatcga gcgattttct    2940
gttgtctgac actagttttt agttttaaaa aatgttggaa gaacatggtg caataggtaa    3000
tttcatagaa tttccatgtg ttttttttca attaaccaat tatccaaatc ttccaaactc    3060
acattttgcg gagctgggct atcaagaatc tgctgcagtt ttataagacg agcatctctg    3120
atatcactga aaattaattt ttaatcaaaa cttgaatatc aactaaaccc acttattaac    3180
tttctcgatc ttctgtcgtt cggtacgatg acggtgaaga agccaattgt agtagttgat    3240
ttggttcaag tccttttcggt gttgtacgtc agtgtcctgc aatgctattt agttataact   3300
taggcctaag attcaattta atgaagtgat taaatttgtt ctctgaacct cttaagatga    3360
tcttttggat tagaaacata taagacaggt ttacctatct attaaaaaac agatcaaaat    3420
agatacgacc aaatcggata atccatgcct acctggcatc taggaacgtg ttcttagaag    3480
atttcttacg taatcgtatg aagaaataac aatttgatcg ttggccagca aaaatagggt    3540
tttaagtggg atagtgtttt tattagctaa ccggaaaatt ttatagtttt tttttgcaag    3600
aaaccactga aaaccccta attgtataca ttttttggag cagcttctgg tcttttgag     3660 caataaaatt cgataaaaca gaatttaagt gtaaattgtt cacatttagt ttctatttta    3720
tcaaattttg ttgctcaaaa acattcgaag ctgctctaaa aaaatgcatt aaaaaagggg    3780
ttttcagtgg ttttttcacat taaaaaagct aatttaact aaaaatccat catatttcca    3840
actttgtcac aacaataaaa tgctggtcaa aatgtgttcg aaaaaatgtt tttttttta    3900 attttttataa tttaaaaata gttttctttc gctgggacac atacattttt gggcgtaaat   3960
tttcagttca aatttccatt tttacaacca taatcataaa gctacgtctg atctctctcg    4020
cacttacctg cgcctgattc gaaagaacaa ccgtagccaa aagaacaaga agaacaagca    4080
cgtagttgtg gtagtggacg ttcatcacgc aatactgacc aatggtcgtg gggtctcact    4140
ttccgtacta ttgagagagg ggagactgaa gatggcaatt gaggacagtg tcttcgacgc    4200
acgcatgcat ccataagcat aatccaggag ggatggagag aaaaatcttg tttctaagcc    4260 cctcccttg taatacatac acatatctaa taccgaagaa tggctaattg aatggacgtc     4320
agctgttgct gtagttgcca aggcatcatc gatgaaataa ctgaaagaaa gaattaaata    4380
attattgcag gcgtatccgg cggtcattga agacttggac ttgattgagg aggaggatca    4440
gatcatccat acacttaatt tggaggatgc ggttgatccg gaaaatgggc ttagtaagtg    4500
actgaccaca cgcggggggc attaatttaa taaattgaat tccatttcag atgtgttcaa    4560
actagatcca gaattcgaaa agaacgagga ggtttatgag gagatccgta aggaaatcat    4620
tggaaacgcc gatatttcgg atgaggatgg tggcgacgag ttggatgatg aagaagaggg    4680
tagtgatgtg gaagaggctc cgaagaagac tacagagatt attgataata ctgatcagaa    4740
ttgactgctt tcagaaggta ttcattttga gttttgggcc ggcaaatctg taagttgccg    4800
gttgccgaaa atttgctgaa tttgccggaa aaaaaaattc cggaatttat ttaaaaactt    4860
```

-continued

```
tttgtaaaaa ttaaattaaa tttgcaactt ttcagagaag tctacctgac aatgcaatca    4920
tctttggact accaagaagc tgctcacaaa ttgctgaaaa tgaagattcc agacagcatg    4980
caggtcagcg atgttgcaaa gaaaattttt cgaccaaaaa aaccaaccaa tcataaaatt    5040
taaaaaaaaa ctccgttttt ttctttttt ttatacgaga aaaaccaaaa aaatgtattt     5100
ttgccaaatt ctaaaatact atccccgaaa ttttcaatat tttctctttc agaacgaact    5160
ctgcgcgatg cttgtcgatt gttgtgctca acagcgtacc tacgagcgat tctacggaat    5220
gctcatcgaa cgtttctgcc gacttcgcct cgaataccag caatactttg aaaagctctg    5280
ccaggacacg tattccacga ttcaccgaat tgacatcaca aaactgcgga atttggctcg    5340
ccttattgct catttgctct cgacggatgc tattgactgg aagattttgg ccgatatgaa    5400
aatgaccgaa gaggacacaa cttcttctgg cagaatctat attaaatata tatttaatga    5460
acttgtggag gcgatgggaa tggttaaact tcattcgaga gttactgatc cgtgagtttc    5520
ctagagagag ttgttttcgt attcaatttt ccctatttc agaactttgg ctcattgctt     5580
tgttggatta ttcccacgaa ctaatccgaa cagcgcacga ttttcgatca acttcttcac    5640
aatgattgga ttgggtggtt tgacgttgga acttcgtgaa tggctggcaa agggtctcaa    5700
gaagaagaag ggaatgctgg atcagttgaa ggccgaatca agctcagatt catcgtcgtc    5760
ttcggattcg tcagactcgt ctgattcttc ggattctgac gattcatccg actcgtcttc    5820
agattcctca tcttcttcag aatcagagcc agaaccaccg aagaaaaaga agaagaa       5880 cagtgaagag agttccaaaa agaaggaaaa agagaatatt ggtcgacggg atcgtggaga    5940
caagagagct gaacgtcatc gtgatcaaag tgtggagaac aaggacaagg atcgtcgacg    6000
tcgccaggat tctgacgaaa atcgtcggcc agaacgagga gatgaccgca aggatcggag    6060
taaagatcgt cgtcgtcaag actcggatga tgaggatcgg aaaggtcgtg aacgtcggga    6120
agattcaggg gaaagacgtc gcggagatcg ggatcgacgt gatcgaaaca aggatcagga    6180
ggatcaccgt gaagatcgcc gtgaccgaag caaggatcgt gaggatcgac gtgatcgccg    6240
tcgtcatgac tctgatgatg atcgtaaaac tcgtcgggat agaagtgaag agcgaggagg    6300
acgtcgtcgt gaagtggaat cggatgatcg acgccgacgt cgttgaattt tcaaattta    6360 aatactgaat atttgttttt tttcctatta tttatttatt ctctttgtgt ttttttctt    6420 gctttctaaa aaattaattc aatccaaatc taaacatgag cggttttttt tctctttccg    6480
tctcccaatt cgtattccgc tcctctcatc tgaacacaat gtgcaagttt atttatcttc    6540
tcgctttcat ttcattagga cgtgggggga attggtggaa ggggaaaaca cacaaaagga    6600
tgatggaaat gaaataagga cacacaatat gcaacaacat tcaattcaga aatatggagg    6660
aaggtttaaa agaaaacata aaatatata gaggaggaag gaaaactagt aaaaaataag     6720
caaagaaatt aggcgaacga tgagaattgt cctcgcttgg caaatgcgaa tccgtatgga    6780
gaggcacgtt tggcgaaggc aaatgttcgg tatggagatc tgtaaaaatt tttaagttga    6840
aatttggtgt tgctcttta caaaattttc cgattttcgc ttgaaattac ggtgccaggt    6900
ctcgacacgt cttccaattt ttcaaattca aaagagcctt taatgggctg tagttgctaa    6960
tttctcgttt tgaaaattt ttcttccgtt taatcgaaat ttgatgtatt ttatttatga    7020
ttttcaataa atttcaaaga aactggtgaa aactcggaaa attgtgaact acagtaatcc    7080
aatccttaaa ggcgcacacc ttttaaatgt ccgccccaat acgatatttt ttaagattc    7140 gctagagcgg ccgccaccgc ggtggagctc caattcgccc tatagtgagt cgtattacaa    7200
```

```
ttcactggcc gtcgttttac aacgtcgtga ctgggaaaac cctggcgtta cccaacttaa   7260
tcgccttgca gcacatcccc ccttcgccag ctggcgtaat agcgaagagg cccgcaccga   7320
tcgcccttcc caacagttgc gtagcctgaa tggcgaatgg gacgcgccct gtagcggcgc   7380
attaagcgcg gcgggtgtgg tggttacgcg cagcgtgacc gctacacttg ccagcgccct   7440
agcgcccgct cctttcgctt tcttcccttc ctttctcgcc acgttcgccg gctttccccg   7500
tcaagctcta atcggggggc tccctttagg gttccgattt agtgctttac ggcacctcga   7560
ccccaaaaaa cttgattagg gtgatggttc acgtagtggg ccatcgccct gatagacggt   7620
ttttcgccct ttgacgttgg agtccacgtt ctttaatagt ggactcttgt tccaaactgg   7680
aacaacactc aaccctatct cggtctattc ttttgattta tagggatttt tgccgatttc   7740
ggcctattgg ttaaaaaatg agctgattta acaaaaattt aacgcgaatt ttaacaaaat   7800
attaacgttt acaatttcag gtggcacttt tcggggaaat gtgcgcggaa cccctatttg   7860
tttatttttc taaatacatt caaatatgta tccgctcatg agacaataac cctgataaat   7920
gcttcaataa tattgaaaaa ggaagagtat gagtattcaa catttccgtg tcgcccttat   7980
tcccttttt gcggcattt gccttcctgt ttttgctcac ccagaaacgc tggtgaaagt   8040
aaaagatgct gaagatcagt tgggtgcacg agtgggttac atcgaactgg atctcaacag   8100
cggtaagatc cttgagagtt ttcgccccga agaacgtttt ccaatgatga gcacttttaa   8160
agttctgcta tgtggcgcgg tattatcccg tattgacgcc gggcaagagc aactcggtcg   8220
ccgcatacac tattctcaga atgacttggt tgagtactca ccagtcacag aaaagcatct   8280
tacggatggc atgacagtaa gagaattatg cagtgctgcc ataagcatga gtgataacac   8340
tgcggccaac ttacttctga caacgatcgg aggaccgaag gagctaaccg cttttttca   8400
caacatgggg gatcatgtaa ctcgccttga tcgttgggaa ccggagctga atgaagccat   8460
accaaacgac gagcgtgaca ccacgatgcc tgtagcaatg gcaacaacgt tgcgcaaact   8520
attaactggc gaactactta ctctagcttc ccggcaacaa ttaatagact ggatggaggc   8580
ggataaagtt gcaggaccac ttctgcgctc ggcccttccg gctggctggt ttattgctga   8640
taaatctgga gccggtgagc gtgggtctcg cggtatcatt gcagcactgg ggccagatgg   8700
taagccctcc cgtatcgtag ttatctacac gacgggcagt caggcaacta tggatgaacg   8760
aaatagacag atcgctgaga taggtgcctc actgattaag cattggtaac tgtcagacca   8820
agtttactca tatatacttt agattgattt aaaacttcat ttttaattta aaaggatcta   8880
ggtgaagatc cttttgata atctcatgac caaaatccct taacgtgagt tttcgttcca   8940
ctgagcgtca gaccccgtag aaaagatcaa aggatcttct tgagatcctt ttttctgcg   9000
cgtaatctgc tgcttgcaaa caaaaaaacc accgctacca gcggtggttt gtttgccgga   9060
tcaagagcta ccaactcttt ttccgaaggt aactggcttc agcagagcgc agataccaaa   9120
tactgtcctt ctagtgtagc cgtagttagg ccaccacttg aagaactctg tagcaccgcc   9180
tacatacctc gctctgctaa tcctgttacc agtggctgct gccagtggcg ataagtcgtg   9240
tcttaccggg ttggactcaa gacgatagtt accggataag gcgcagcggt cgggctgaac   9300
ggggggttcg tgcacacagc ccagcttgga gcgaacgacc tacaccgaac tgagatacct   9360
acagcgtgag cattgagaaa gcgccacgct tcccgaaggg agaaaggcgg acaggtatcc   9420
ggtaagcggc agggtcggaa caggagagcg cacgagggag cttccagggg gaacgcctg   9480
gtatctttat agtcctgtcg ggtttcgcca cctctgactt gagcgtcgat ttttgtgatg   9540
ctcgtcaggg gggcggagcc tatggaaaaa cgccagcaac gcggcctttt tacggttcct   9600
```

```
ggccttttgc tggccttttg ctcacatgtt ctttcctgcg ttatcccctg attctgtgga      9660
taaccgtatt accgcctttg agtgagctga taccgctcgc cgcagccgaa cgaccgagcg      9720
cagcgagtca gtgagcgagg aagcggaaga gcgcccaata cgcaaaccgc ctctccccgc      9780
gcgttggccg attcattaat gcagctggca cgacaggttt cccgactgga aagcgggcag      9840
tgagcgcaac gcaattaatg tgagttacct cactcattag gcaccccagg ctttacactt      9900
tatgcttccg gctcctatgt tgtgtggaat tgtgagcgga taacaatttc acacaggaaa      9960
cagctatgac catgattacg ccaagctcgg aattaaccct cactaaaggg aacaaaagct     10020
gggggggatc ctccaaaatc gtcttccgct ctgaaaaacg aaagtggacc tttgacatcc     10080
gaaaaaatgg gcgaaaaaat gaattgagc tttttgggtc gaaaaaaatg tttttagaat      10140
gctgagaaca cgttaaacac gaagatcata tttattttga gacccggatg ctctgaaaat     10200
gtctgacata gatttaaaaa agcatatata tatttttcat tttcaacgtg aaagttttgt     10260
gcaactttat agaatctcct attggcacat tgttttttat ttaactgagg cagttttga      10320 acacctttt gaaactttga atctctttga agtatactgt cgaaaagact gacttgagcg     10380
ttcgaaatgc cagaagaaaa ctatatttga atctcgcgct aaattgagaa atgcaaccgc     10440
gctccactgg acaattggaa aaaaaattta ttcggaggcg acaacggtat tttcgaaatt     10500
gattttctgt gtattttctc attttttata aattcttctt tgatttatcg ttcgtttgtg     10560
agaaatttaa ttgtattcaa actttttat agtaagata                            10599
```

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: T7 promoter
      DNA

<400> SEQUENCE: 12

```
taatacgact cactataggg cga                                                23
```

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 13

```
agctgtaata cgactcacta tagggcgaga agctt                                   35
```

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 14

```
tcgaaagctt ctcgcataat agtgagtcgt attac                                   35
```

<210> SEQ ID NO 15
<211> LENGTH: 29
<212> TYPE: DNA
<213> ORGANISM: Artificial Sequence -continued

```
<220> FEATURE:
<223> OTHER INFORMATION: Description of Artificial Sequence:
      oligonucleotide DNA

<400> SEQUENCE: 15
catggcagga tgaacacgat taacatcgc                                    29

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 16
atggccccat ggttacggga acgcgaagtc cg                                32

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 17
atggaattct tacgcgaacg cgaagtccg                                    29

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 18
ctcaccggta atgaacacga ttaacatcgc                                   30

<210> SEQ ID NO 19
<211> LENGTH: 12
<212> TYPE: PRT
<213> ORGANISM: Simian virus 40

<400> SEQUENCE: 19

Met Thr Ala Pro Lys Lys Lys Arg Lys Val Pro Val
 1               5                  10

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 20
gccaccggtg cgagctcatg aacacgatta acatcgc                           37

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence:
      oligonucleotide DNA
```

```
<400> SEQUENCE: 21
cactagtggg cccttacgcg aacgcgaagt ccg                              33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 22
ccggatgact gctccaaaga agaagcgtaa gct                              33

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 23
cccgggatta atacgactca ctata                                       25

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 24
ccggtatagt gagtcgtatt aatcccggga gct                              33

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 25
aattcttaat acgactcact atagggcc                                    28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 26
catgggccct atagtgagtc gtattaag                                    28

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence:
      oligonucleotide DNA
```

```
<400> SEQUENCE: 27
gatccgtcga cagatctccc tatagtgagt agtattactg ca                    42

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 28
gtaatacgac tcactatagg gagatctgtc gacg                             34

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:
      oligonucleotide DNA

<400> SEQUENCE: 29
tatgccctat agtgagtcgt attaag                                      26
```

What is claimed is:

1. A method of identifying DNA responsible for conferring a phenotype of a *C. elegans* cell or *C. elegans* organism, which method comprises
   a) constructing a cDNA or genomic library of the DNA of said *C. elegans* cell or *C. elegans* organism in a vector in an orientation relative to a promoter(s) that initiates transcription of said cDNA or DNA to double stranded (ds) RNA upon binding of a transcription factor to said promoter(s),
   b) introducing said library and/or dsRNA into a plurality of said *C. elegans* cells or *C. elegans* organisms, and
   c) identifying a phenotype of said plurality of *C. elegans* cells or *C. elegans* organisms comprising a member of said library and/or dsRNA and identifying the DNA or cDNA from said library responsible for conferring said phenotype.

2. The method of claim 1, wherein the step of introducing said library and/or dsRNA comprises feeding micro-organisms comprising said library and/or dsRNA to said *C. elegans* organisms.

3. The method of claim 2, wherein said micro-organisms are adapted to express said transcription factor.

4. The method of claim 2, wherein the micro-organisms are bacteria or yeast.

5. The method of claim 4, wherein the bacteria are *E. coli*.

6. The method of claim 2, wherein the library is transformed in the micro-organisms.

7. A method according to claim 1 wherein said library is organised into hierarchical pools prior to step b).

8. A method of assigning function to a known DNA sequence which method comprises
   a) identifying a homologue(s) of said known DNA sequence in a *C. elegans* cell or *C. elegans* organism,
   b) isolating the relevant DNA homologue(s) or a fragment thereof from said *C. elegans* cell or *C. elegans* organism,
   c) cloning said homologue or fragment thereof into a vector in an orientation relative to a promoter(s) that initiates transcription of dsRNA from said DNA homologue or fragment upon binding of a transcription factor to said promoter(s),
   d) transforming micro-organisms with said vector,
   e) feeding said micro-organisms to said *C. elegans* organisms, and
   f) identifying the phenotype of said or *C. elegans* organisms compared to wild type.

9. The method of claim 8, wherein the micro-organisms are bacteria or yeast.

10. The method of claim 9, wherein the bacteria are *E. coli*.

11. A method according to any of claim 1, 8 or 2 wherein said DNA library, homologue or fragment is cloned in a sense and an antisense direction relative to said promoter.

12. A method according to any of claim 1, 8 or 2 wherein said DNA library, homologue or fragment is cloned between two promoters capable of producing dsRNA from said DNA library, homologue or fragment upon binding of said transcription factor to said promoters.

13. A method according to any of claim 1, 8 or 2 wherein said *C. elegans* cell or *C. elegans* organism is adapted to express said transcription factor.

14. A method according to any of claim 1, 8 or 2 wherein said transcription factor is encoded by a further vector independent of the vector including said DNA library, DNA homologue or fragment and which sequence encoding said transcription factor is operably linked to a promoter.

15. A method according to any of claim 1, 8 or 2 wherein said *C. elegans* cell is contained in an organism or an embryo thereof.

16. A method according to any of claim 1, 8 or 2 wherein said promoters are T7 promoters.

17. A method according to any of claim 1, 8 or 2 wherein said transcription factor is inducible.

18. A method according to any of claim 1, 8 or 2 further comprising contacting said *C. elegans* cell or *C. elegans* organism with a compound for screening for a phenotype.

19. A method according to claim 18 wherein said phenotype is resistance or sensitivity to said compound when compared to the wild type *C. elegans* cell or *C. elegans* organism.

20. A method according to any of claim 1, 8 or 2 wherein said DNA library, homologue or fragment is constructed in a suitable vector which comprises a sequence of nucleotides encoding said transcription factor operably linked to a promoter.

21. A method according to claim 20 wherein said transcription factor comprises any of T7, T3 or SP6 polymerase.

22. A method according to claim 20 wherein said promoter comprises any of let 858, SERCA, UL6, myo 2 or myo 3.

23. A method according to claim 20, wherein said vector comprises a selectable marker.

24. A method according to claim 23 wherein said selectable marker comprises a nucleotide sequence capable of inhibiting or preventing expression of a gene in said *C. elegans* cell or *C. elegans* organism and which gene is responsible for conferring a second phenotype.

25. A method according to claim 24 wherein said nucleotide sequence comprises a sequence which is a part of or identical to said gene conferring said second phenotype, and which nucleotide sequence is itself oriented relative to a promoter(s) that initiates transcription of double stranded RNA upon binding of a transcription factor to said promoter(s).

26. A method according to claim 24 wherein said nucleotide sequence is a part of or identical to said gene conferring said second phenotype, and which nucleotide sequence permits integration of said vector by homologous recombination in the genome of said *C. elegans* cell or *C. elegans* organism wherein said nucleotide sequence does not express said gene sequence.

27. A method according to claim 26 wherein said nucleotide sequence comprises stop codons sufficient to prevent translation of said nucleotide sequence following its integration into said genome.

28. A method according to claim 24 wherein said known gene sequence comprises a sup 35 gene or a fragment thereof which is selectable by identifying offspring growing at a temperature above 25° C. following introduction of said vector in the genome of a pha I et123ts mutant *C. elegans* worm.

29. A method of validating clones identified in yeast two hybrid vector experiments which method comprises
   a) providing a construct including the DNA encoding the protein identified in the two hybrid vector experiment, which construct is such that said DNA is orientated relative to a promoter(s) that initiates transcription of said DNA to double stranded RNA upon binding of a transcription factor to said promoter(s),
   b) transforming a *C. elegans* cell or *C. elegans* organism comprising said transcription factor with said construct, and
   c) identifying a phenotypic change in said *C. elegans* cell or *C. elegans* organism when compared to a wild type.

30. A method according to claim 29 wherein said DNA sequence is provided between two promoters capable of initiating transcription of the DNA sequence to dsRNA upon binding of the transcription factor to said promoters.

31. A method according to claim 29 wherein said DNA is provided in a sense and an antisense orientation relative to said promoter such that binding of the transcription factor to said promoter initiates transcription of dsRNA from said DNA.

32. A method according to claim 29 wherein said transcription factor is inducible in said *C. elegans* cell.

33. A method according to claim 29 wherein said promoter is a phage polymerase promoter and said transcription factor is a RNA polymerase.

34. A method according to claim 33 wherein said polymerase is any of T7 RNA polymerase, T3 RNA polymerase or SP6 RNA polymerase.

35. A method according to claim 34 wherein said promoters comprise any of T7, T3 or SP6 promoter.

36. A method according to claim 29 wherein said construct is such that it may be used in yeast two hybrid experiments.

37. A method according to claim 29 wherein said cell is part of an organism or an embryo thereof.

* * * * *

UNITED STATES PATENT AND TRADEMARK OFFICE
CERTIFICATE OF CORRECTION

PATENT NO.       : 7,005,423 B1
APPLICATION NO.  : 09/347311
DATED            : February 28, 2006
INVENTOR(S)      : Geert Plaetinck et al.

Page 1 of 1

It is certified that error appears in the above-identified patent and that said Letters Patent is hereby corrected as shown below:

On the title page: please add the Foreign Application Priority Data as follows:

(30)   Foreign Application Priority Data

July 3, 1998  GB  9814536.0
Dec. 9, 1998  GB  9827152.1

Signed and Sealed this

Twelfth Day of December, 2006

JON W. DUDAS
*Director of the United States Patent and Trademark Office*